US011529402B2

(12) United States Patent
Hanahan et al.

(10) Patent No.: US 11,529,402 B2
(45) Date of Patent: Dec. 20, 2022

(54) RECOMBINANT VACCINIA VIRUS AND METHODS OF USE THEREOF

(71) Applicant: Ignite Immunotherapy, Inc., New York, NY (US)

(72) Inventors: Douglas Hanahan, Saint-Sulpice (CH); David H. Kirn, Mill Valley, CA (US); Liliana Maruri Avidal, Oakland, CA (US); Michael D. Eisenbraun, San Diego, CA (US); Joseph J. Binder, San Diego, CA (US); Clare Lees, Del Mar, CA (US)

(73) Assignee: Ignite Immunotherapy, Inc., New York, NY (US)

( * ) Notice: Subject to any disclaimer, the term of this patent is extended or adjusted under 35 U.S.C. 154(b) by 124 days.

(21) Appl. No.: 16/738,535

(22) Filed: Jan. 9, 2020

(65) Prior Publication Data

US 2020/0222520 A1 Jul. 16, 2020

Related U.S. Application Data

(60) Provisional application No. 62/886,727, filed on Aug. 14, 2019, provisional application No. 62/854,121, filed on May 29, 2019, provisional application No. 62/792,287, filed on Jan. 14, 2019.

(51) Int. Cl.

| | |
|---|---|
| *A61K 39/00* | (2006.01) |
| *A61P 31/00* | (2006.01) |
| *A61P 35/00* | (2006.01) |
| *A61K 39/395* | (2006.01) |
| *C07K 16/28* | (2006.01) |
| *A61K 45/06* | (2006.01) |

(52) U.S. Cl.

CPC ................. *A61K 39/001119* (2018.08); *A61K 39/39558* (2013.01); *A61P 31/00* (2018.01); *A61P 35/00* (2018.01); *C07K 16/2827* (2013.01); *A61K 45/06* (2013.01); *A61K 2039/5152* (2013.01)

(58) Field of Classification Search

CPC .... A61K 31/16; A61K 38/177; A61K 9/0019; A61K 39/001119; C12Q 1/6886

See application file for complete search history.

(56) References Cited

U.S. PATENT DOCUMENTS

| | | | | |
|---|---|---|---|---|
| 8,980,246 | B2 * | 3/2015 | Kirn | A61K 35/768 424/93.2 |
| 9,226,977 | B2 * | 1/2016 | Kirn | A61N 5/10 |
| 9,266,938 | B2 | 2/2016 | Ast et al. | |
| 9,447,159 | B2 | 9/2016 | Ast et al. | |
| 9,526,797 | B2 | 12/2016 | Gerdes et al. | |
| 9,919,062 | B2 * | 3/2018 | Kirn | A61K 38/208 |
| 2016/0235793 | A1 * | 8/2016 | Thorne | C12N 7/00 |
| 2019/0062395 | A1 | 2/2019 | Merchant et al. | |

FOREIGN PATENT DOCUMENTS

| | | | |
|---|---|---|---|
| WO | WO-2012107417 A1 * | 8/2012 | A61K 47/6849 |
| WO | 2018/234862 | 12/2018 | |

OTHER PUBLICATIONS

Rao et al., Interleukin-2 mutants with enhanced a-receptor subunit binding affinity, Protein Eng., 2003, vol. 16(12):1081-1087 (Year: 2003).*

Buchli et al., Structural and Biologic Properties of a Human Aspartic Acid-126 Interleukin-2 Analog, Arch. Biochem. Biophys., 1993, vol. 307(2):411-415 (Year: 1993).*

J2R/Thymidine Kinase, https://www.uniprot.org/uniprot/A0A2I2MCC6, retrieved on Dec. 13, 2021 (Year: 2021).*

U.S. Appl. No. 16/786,134, filed Feb. 10, 2020.

Acres, B., et al., "Directed cytokine expression in tumour cells in vivo using recombinant vaccinia virus", Therapeutic Immunology, 1994, pp. 17-23, vol. 1.

Chen, H., et al., "Regulating Cytokine Function Enhances Safety and Activity of Genetic Cancer Therapies", Molecular Therapy, 2013, pp. 167-174, vol. 21, No. 1.

Ghasemi, R., et al., "Selective targeting of IL-2 to NKG2D bearing cells for improved immunotherapy", Nature Communications, 2016, pp. 1-15, 7:12878 | DOI: 10.1038.

Havunen, R., et al., "Abscopal Effect in Non-injected Tumors Achieved with Cytokine-Armed Oncolytic Adenovirus", Molecular Therapy: Oncolytics, 2018, pp. 109-121, vol. 11.

Jensen, B., et al., "Co-Expression of Tumor Antigen and Interleukin-2 From an Adenoviral Vector Augments the Efficiency of Therapeutic Tumor Vaccination", Molecular Therapy, 2014, pp. 2107-2117, vol. 22, No. 12.

Klein, C., et al., "Cergutuzumab amunaleukin (CEA-IL2v), a CEA-targeted IL-2 variant-based immunocytokine for combination cancer immunotherapy: Overcoming limitations of aldesleukin and conventional IL-2- based immunocytokines", Oncommunology, 2017, e1277306, pp. 1-15.

Liu, Z., et al., "Modifying the cancer-immune set point using vaccinia virus expressing re-designed interleukin-2", Nature Communications, 2018, DOI: 10.1038/s41467-018-06954-z, 9:4682.

Guo, Z., et al., "Vaccinia virus-mediated cancer immunotherapy: cancer vaccines and oncolytics", Journal for ImmunoTherapy of Cancer, 2019, pp. 1-21, vol. 7, No. 6.

International Search Report, PCT/IB2020/050159, dated Mar. 20, 2020.

* cited by examiner

*Primary Examiner* — Peter J Reddig
*Assistant Examiner* — Cheng Lu
(74) *Attorney, Agent, or Firm* — Austin W. Zhang

(57) ABSTRACT

The present disclosure provides a replication-competent, recombinant oncolytic vaccinia virus; and compositions comprising the replication-competent, recombinant oncolytic vaccinia virus. The present disclosure also provides use of the vaccinia virus or composition for inducing oncolysis in an individual having a tumor.

9 Claims, 49 Drawing Sheets

Specification includes a Sequence Listing.

FIG. 1

Human IL-2 (mature form)

APTSSSTKKT QLQLEHLLLD LQMILNGINN YKNPKLTRML TFKFYMPKKA
TELKHLQCLE EELKPLEEVL NLAQSKNFHL RPRDLISNIN VIVLELKGSE
TTFMCEYADE TATIVEFLNR WITFCQSIIS TLT
(SEQ ID NO:1)

Human IL-2 with signal peptide (bolded and underlined) (precursor form)

MYRMQLLSCI ALSLALVTNS APTSSSTKKT QLQLEHLLLD LQMILNGINN
YKNPKLTRML TFKFYMPKKA TELKHLQCLE EELKPLEEVL NLAQSKNFHL
RPRDLISNIN VIVLELKGSE TTFMCEYADE TATIVEFLNR WITFCQSIIS
TLT
(SEQ ID NO:21)

FIG. 2

Mouse IL-2 (mature form)

APTSSSTSSS TAEAQQQQQQ QQQQQQHLEQ LLMDLQELLS RMENYRNLKL PRMLTFKFYL
PKQATELKDL QCLEDELGPL RHVLDLTQSK SFQLEDAENF ISNIRVTVVK LKGSDNTFEC
QFDDESATVV DFLRRWIAFC QSIISTSPQ
(SEQ ID NO:23)

Mouse IL-2 with signal peptide (bold and underlined) (precursor form)

MYSMQLASCV TLTLVLLVNS APTSSSTSSS TAEAQQQQQQ QQQQQQHLEQ
LLMDLQELLS RMENYRNLKL PRMLTFKFYL PKQATELKDL QCLEDELGPL
RHVLDLTQSK SFQLEDAENF ISNIRVTVVK LKGSDNTFEC QFDDESATVV
DFLRRWIAFC QSIISTSPQ
(SEQ ID NO:24)

FIG. 4 (Table 1)

| | **ANCOVA results (p values for designated comparisons)** | | | | | |
|---|---|---|---|---|---|---|
| Post-tumor cell implant time point | Cop.Luc-GFP A34-K151E vs. Vehicle Tx | Cop.mGM-CSF A34-K151E vs. Vehicle Tx | Cop.mIL-2v A34-K151E vs. Vehicle Tx | Cop.Luc-GFP A34-K151E vs. Cop.mGM-CSF A34-K151E | Cop.mIL-2v A34-K151E vs. Cop.Luc-GFP A34-K151E | Cop.mIL-2v A34-K151E vs. Cop.mGM-CSF A34-K151E |
| Day 7 | 0.307 | 0.414 | 0.593 | 0.755 | 0.456 | 0.652 |
| Day 13 | 0.116 | 0.058 | **0.013** | 0.743 | 0.323 | 0.492 |
| Day 18 | 0.192 | **0.025** | **<0.001** | 0.302 | **0.021** | 0.177 |
| Day 21 | 0.234 | **0.019** | **<0.001** | 0.194 | **0.020** | 0.268 |

| Group | Median survival |
|---|---|
| 1 | Day 35 |
| 2 | Day 35 |
| 3 | Day 39 |
| 4 | *undefined* |

FIG. 9A
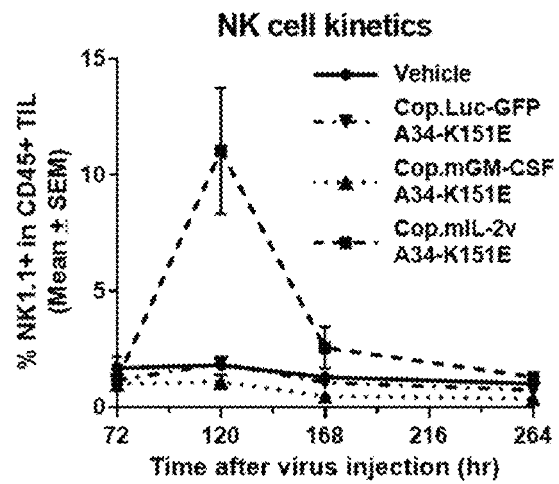
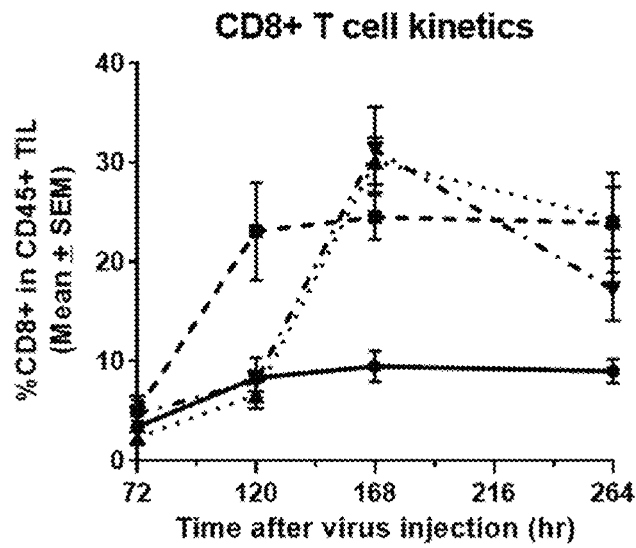
FIG. 9B
FIG. 9C
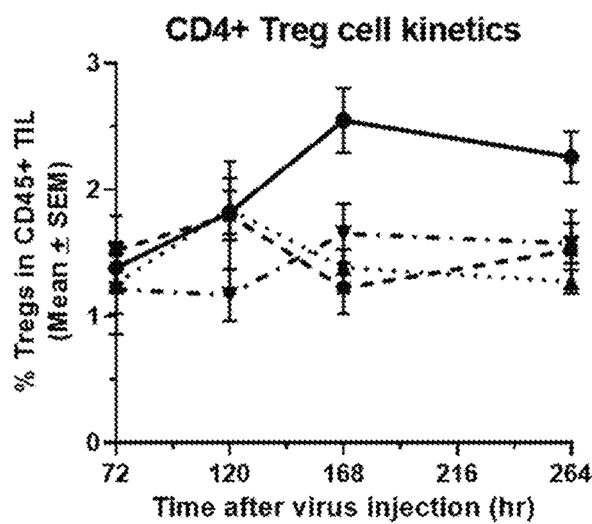

FIG. 9D
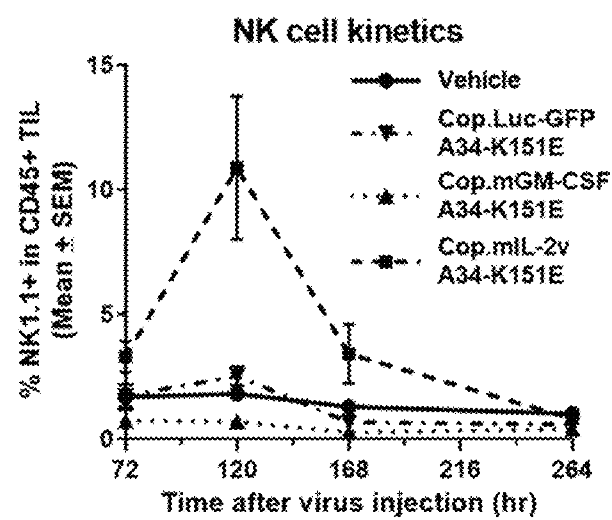
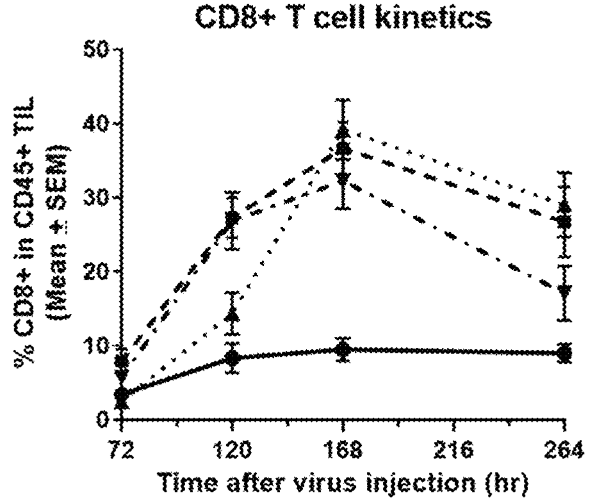
FIG. 9E
FIG. 9F
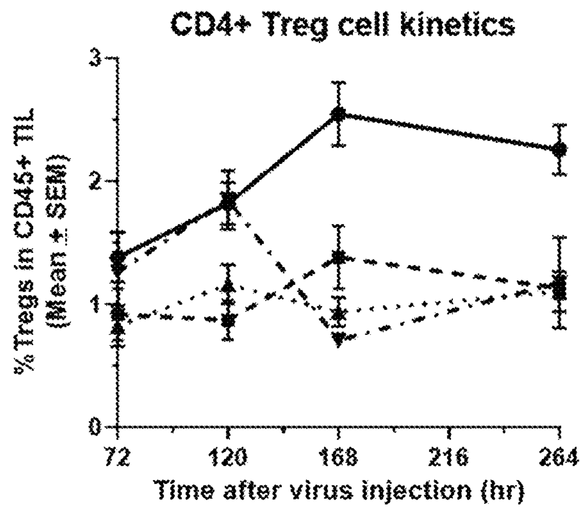

FIG. 10H
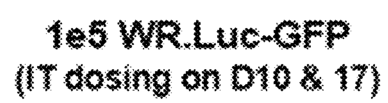
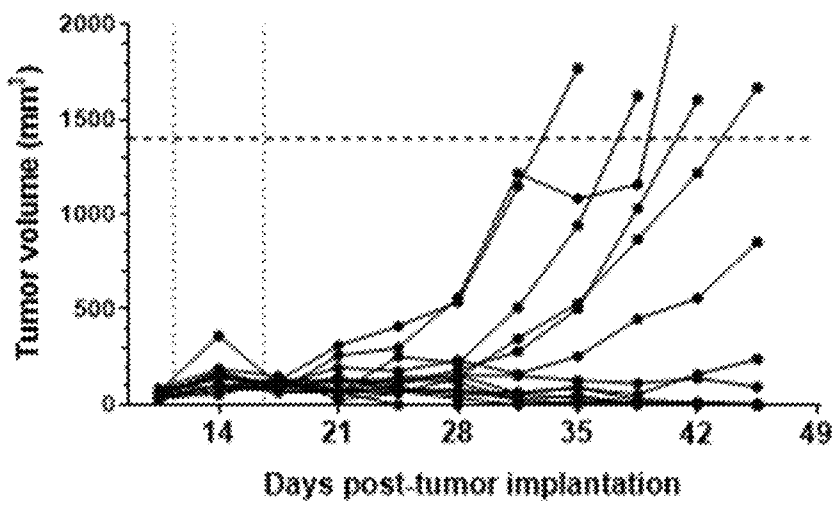
FIG. 10I
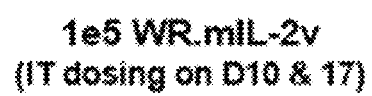
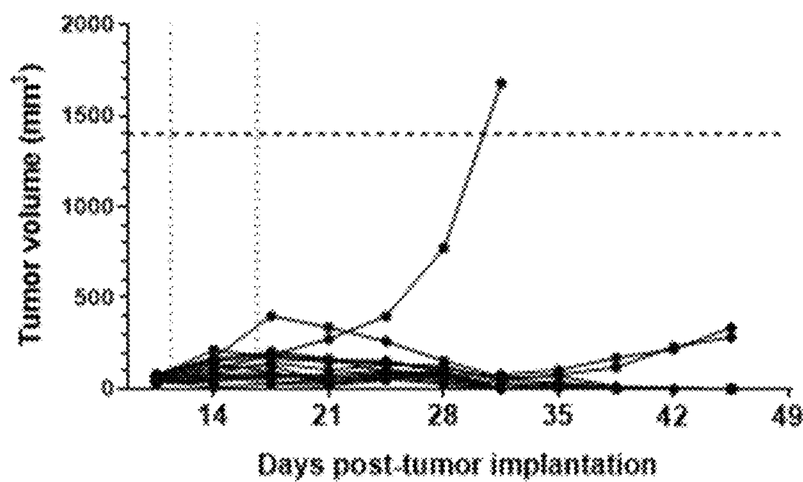

FIG. 11 (Table 2)

| | **ANCOVA results (p values for designated comparisons)** | | | | | | | | |
|---|---|---|---|---|---|---|---|---|---|
| Post-tumor cell implant time point | Cop.Luc-GFP vs. Vehicle Tx | Cop.Luc-GFP.A34-K151E vs. Vehicle Tx | Cop.**mIL-2v**.A34-K151E vs. Vehicle Tx | Cop.**mIL-2v**.A34-K151E vs. Vehicle Tx | WR.Luc-GFP vs. Vehicle Tx | WR.**mIL-2v** vs. Vehicle Tx | Cop.**mIL-2v** vs. Cop.Luc-GFP | Cop.**mIL-2v**.A34-K151E vs. Cop.Luc-GFP.A34-K151E | WR.**mIL-2v** vs. WR.Luc-GFP |
| Day 9 | 0.398 | 0.219 | 0.336 | 0.237 | 0.309 | 0.452 | 0.860 | 0.956 | 0.694 |
| Day 14 | **0.003** | **<0.001** | **<0.001** | **<0.001** | **0.004** | **<0.001** | 0.181 | 0.443 | 0.119 |
| Day 18 | **<0.001** | **<0.001** | **<0.001** | **<0.001** | **<0.001** | **<0.001** | 0.216 | 0.254 | 0.762 |
| Day 21 | **<0.001** | **<0.001** | **<0.001** | **<0.001** | **<0.001** | **<0.001** | 0.046 | **0.017** | 0.223 |
| Day 24 | **<0.001** | **0.011** | **<0.001** | **<0.001** | **<0.001** | **<0.001** | 0.279 | **0.014** | 0.805 |

FIG. 17 (Table 4)

| | **ANCOVA results (p values for designated comparisons)** | | | | | |
|---|---|---|---|---|---|---|
| Post-tumor cell implant time point | WR.Luc-GFP A34-K151E vs. Vehicle Tx | WR.mIL2v vs. Vehicle Tx | WR.mIL2v A34-K151E vs. Vehicle Tx | WR.Luc-GFP A34-K151E vs. WR.mIL2v | WR.Luc-GFP A34-K151E vs. WR.mIL2v A34-K151E | WR.mIL2v vs. WR.mIL2v A34-K151E |
| Day 17 | 0.457 | 0.911 | 0.714 | 0.146 | 0.501 | 0.430 |
| Day 20 | 0.055 | 0.215 | 0.085 | 0.415 | 0.822 | 0.555 |
| Day 24 | **<0.001** | **<0.001** | **<0.001** | 0.086 | **0.035** | 0.667 |
| Day 27 | **<0.001** | **<0.001** | **<0.001** | **<0.001** | **<0.001** | 0.125 |
| Day 31 | 0.063 | **<0.001** | **<0.001** | **<0.001** | **<0.001** | 0.570 |
| Day 34 | 0.310 | **<0.001** | **<0.001** | **<0.001** | **<0.001** | 0.178 |
| Day 38 | 0.706 | **<0.001** | **<0.001** | **<0.001** | **<0.001** | 0.216 |

| Group | Median survival |
|---|---|
| 1 | Day 34 |
| 2 | Day 34 |
| 3 | undefined* |
| 4 | undefined* |

* p<0.0001 vs. G1 or G2

FIG. 21 (Table 5)

| | ANCOVA results (p values for designated comparisons) | | | | | |
|---|---|---|---|---|---|---|
| Post-tumor cell implant time point | D11 only Tx WR.Luc-GFP A34-K151E vs. D11 only Tx WR.mIL2v | D11 only Tx WR.Luc-GFP A34-K151E vs. D11 only Tx WR.mIL2v A34-K151E | D11/D12/D13 Tx WR.Luc-GFP A34-K151E vs. D11/D12/D13 Tx WR.mIL2v | D11/D12/D13 Tx WR.Luc-GFP A34-K151E vs. D11/D12/D13 Tx WR.mIL2v A34-K151E | D11 only Tx WR.mIL2v vs. D11 only Tx WR.mIL2v A34-K151E | D11/D12/D13 Tx WR.mIL2v vs. D11/D12/D13 Tx WR.mIL2v A34-K151E |
| Day 18 | **0.042** | **0.002** | **<0.001** | **0.004** | 0.275 | 0.536 |
| Day 21 | **<0.001** | **<0.001** | **<0.001** | **<0.001** | 0.056 | 0.894 |
| Day 24 | **<0.001** | **<0.001** | **<0.001** | **<0.001** | **<0.001** | 0.931 |
| Day 27 | **<0.001** | **<0.001** | **<0.001** | **<0.001** | **<0.001** | 0.746 |
| Day 31 | **0.002** | **<0.001** | **<0.001** | **<0.001** | **<0.001** | 0.802 |
| Day 34 | **0.020** | **<0.001** | **<0.001** | **<0.001** | **<0.001** | 0.969 |
| Day 39 | 0.197 | **<0.001** | **<0.001** | **<0.001** | **0.003** | 0.894 |

| Group | Median survival | Log-rank test p value vs. G1 | Log-rank test p value vs. G2 |
|---|---|---|---|
| 1 | Day 34 | | |
| 2 | Day 42 | p=0.022 | |
| 3 | Undefined | p<0.0001 | p=0.0011 |

| Group | Median survival | Log-rank test p value vs. G4 | Log-rank test p value vs. G5 |
|---|---|---|---|
| 4 | Day 34 | | |
| 5 | Undefined | p<0.0001 | |
| 6 | Undefined | p<0.0001 | p>0.05 |

FIG. 24 (Table 6)

| | | | D12 sera | | D13 sera | | D14 sera | |
|---|---|---|---|---|---|---|---|---|
| | | | 2-way ANOVA (p value) | | 2-way ANOVA (p value) | | 2-way ANOVA (p value) | |
| **Tx schedule** | **Group** | **Treatment** | **vs. G1** | **vs. G2** | **vs. G1** | **vs. G2** | **vs. G1** | **vs. G2** |
| D11 only Tx | 1 | WR.Luc-GFP.A34-K151E | | | | | | |
| | 2 | WR.mIL2v | <0.0001 | | <0.0001 | | <0.0001 | |
| | 3 | WR.mIL2v.A34-K151E | <0.0001 | >0.05 | <0.0001 | >0.05 | <0.0001 | >0.05 |
| **Tx schedule** | **Group** | **Treatment** | **vs. G4** | **vs. G5** | **vs. G4** | **vs. G5** | **vs. G4** | **vs. G5** |
| D11, D12, D13 Tx | 4 | WR.Luc-GFP.A34-K151E | | | | | | |
| | 5 | WR.mIL2v | <0.0001 | | <0.0001 | | <0.0001 | |
| | 6 | WR.mIL2v.A34-K151E | <0.0001 | >0.05 | <0.0001 | >0.05 | <0.0001 | >0.05 |

| | | | 2-way ANOVA (p value) | | |
|---|---|---|---|---|---|
| **Tx schedule** | **Group** | **Treatment** | **D12 sera** | **D13 sera** | **D14 sera** |
| D11 only Tx | 2 | WR.mIL2v | >0.05 | >0.05 | >0.05 |
| D11, D12, D13 Tx | 5 | WR.mIL2v | | | |
| D11 only Tx | 3 | WR.mIL2v.A34-K151E | >0.05 | >0.05 | >0.05 |
| D11, D12, D13 Tx | 6 | WR.mIL2v.A34-K151E | | | |

FIG. 25A
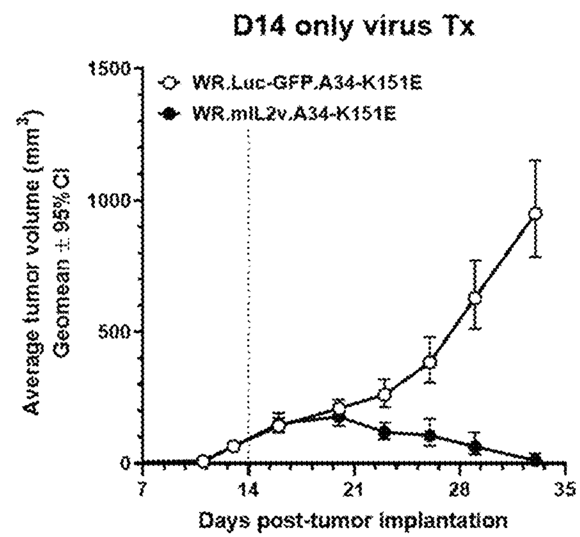
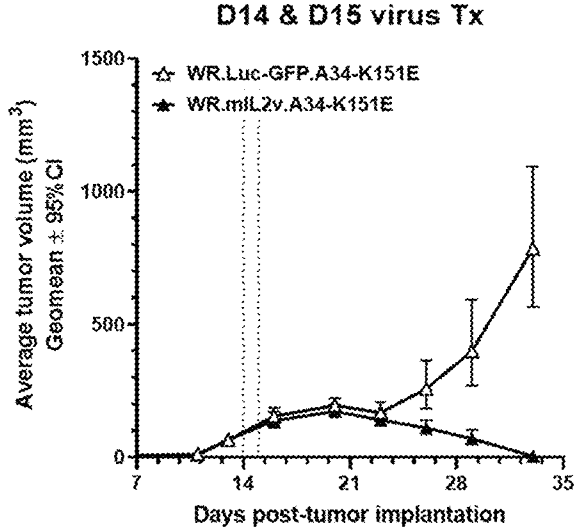
FIG. 25B
FIG. 25C
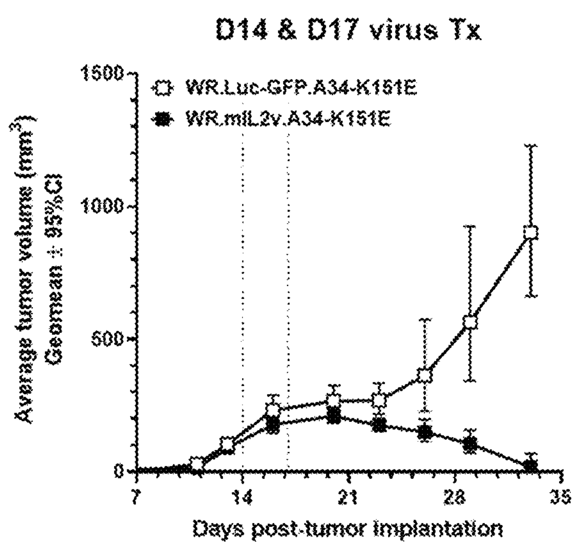

FIG. 26 (Table 7)

| | ANCOVA results (p values for designated comparisons) | | | | | |
|---|---|---|---|---|---|---|
| Post-tumor cell implant time point | D14 only Tx WR.Luc-GFP A34-K151E vs. D14 only Tx WR.mIL2v A34-K151E | D14/D15 Tx WR.Luc-GFP A34-K151E vs. D14/D15 Tx WR.mIL2v A34-K151E | D14/D17 Tx WR.Luc-GFP A34-K151E vs. D14/D17 Tx WR.mIL2v A34-K151E | D14 only Tx WR.mIL2v A34-K151E vs. D14/15 Tx WR.mIL2v A34-K151E | D14 only Tx WR.mIL2v A34-K151E vs. D14/D17 Tx WR.mIL2v A34-K151E | D14/D15 Tx WR.mIL2v A34-K151E vs. D14/D17 Tx WR.mIL2v A34-K151E |
| Day 16 | **0.049** | 0.455 | 0.141 | 0.151 | 0.765 | 0.254 |
| Day 20 | **0.004** | **0.018** | 0.099 | 0.382 | 0.535 | 0.800 |
| Day 23 | **<0.001** | **<0.001** | 0.094 | 0.423 | 0.447 | 0.119 |
| Day 26 | **<0.001** | **<0.001** | **<0.001** | 0.858 | 0.724 | 0.862 |
| Day 29 | **<0.001** | **<0.001** | **<0.001** | 0.577 | 0.673 | 0.892 |
| Day 33 | **<0.001** | **<0.001** | **<0.001** | 0.648 | 0.140 | 0.052 |

FIG. 28 (Table 8)

| | | 2-way ANOVA (p value) | | |
|---|---|---|---|---|
| **Tx schedule** | **Treatment** | **D15 sera** | **D16 sera** | **D18 sera** |
| D14 only Tx | WR.Luc-GFP.A34-K151E<br>WR.mIL2v.A34-K151E | 0.0007 | <0.0001 | <0.0001 |
| | | | | |
| D14 & D15 Tx | WR.Luc-GFP.A34-K151E<br>WR.mIL2v.A34-K151E | 0.0002 | <0.0001 | <0.0001 |
| | | | | |
| D14 & D17 Tx | WR.Luc-GFP.A34-K151E<br>WR.mIL2v.A34-K151E | 0.0002 | <0.0001 | <0.0001 |

| | | 2-way ANOVA (p value) | | |
|---|---|---|---|---|
| **Tx schedule** | **Treatment** | **D15 sera** | **D16 sera** | **D18 sera** |
| D14 only Tx<br>D14 & D15 Tx | WR.mIL2v.A34-K151E | >0.05 | >0.05 | >0.05 |
| | | | | |
| D14 only Tx<br>D14 & D17 Tx | WR.mIL2v.A34-K151E | >0.05 | >0.05 | >0.05 |
| | | | | |
| D14 & D15 Tx<br>D14 & D17 Tx | WR.mIL2v.A34-K151E | >0.05 | >0.05 | >0.05 |

FIG. 29B
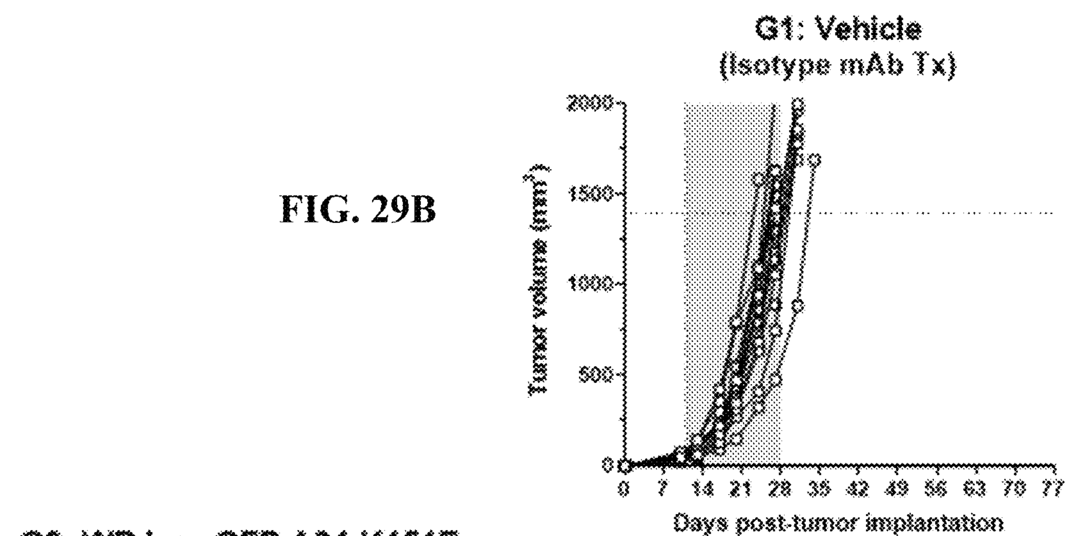
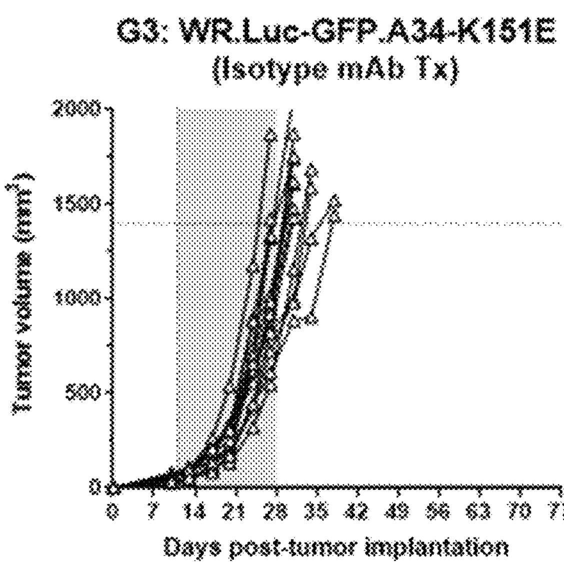
FIG. 29C
FIG. 29D
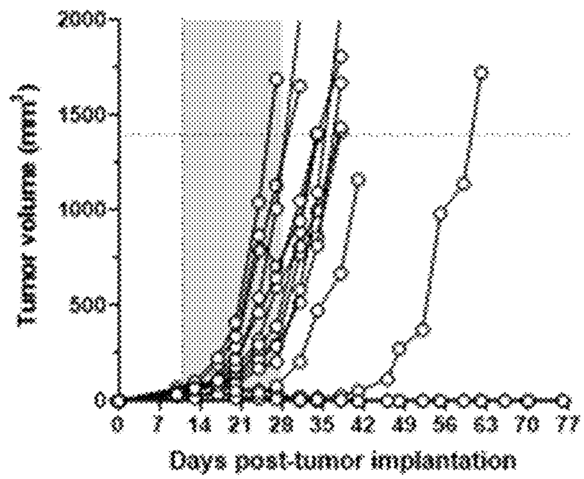

FIG. 29E
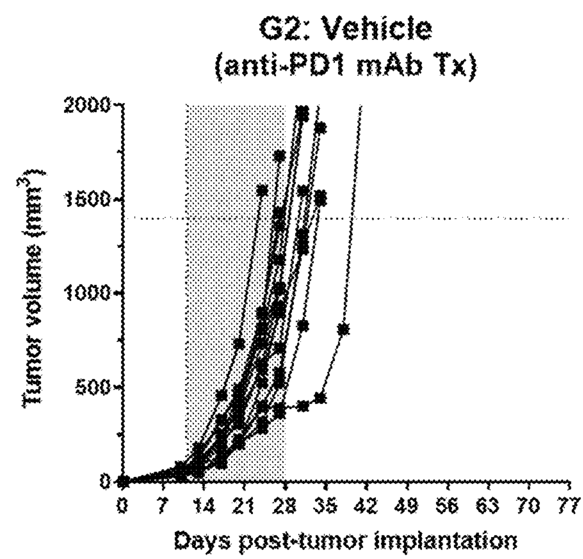
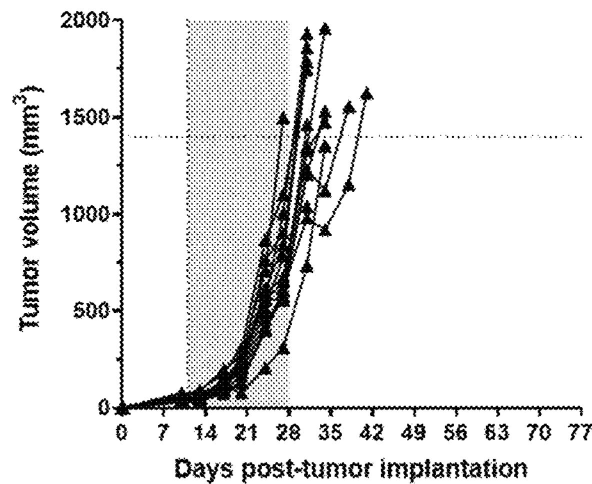
FIG. 29F
FIG. 29G
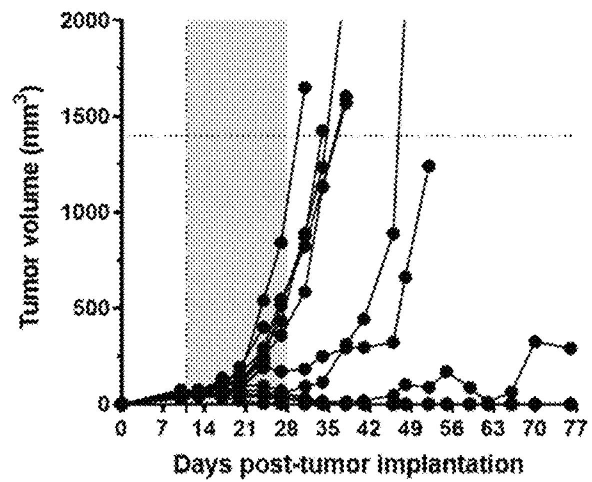

FIG. 30 (Table 9)

| | ANCOVA results (p values for designated comparisons) | | | | | |
|---|---|---|---|---|---|---|
| Post-tumor cell implant time point | Vehicle + isotype mAb vs. WR.Luc-GFP A34-K151E + isotype mAb | Vehicle + isotype mAb vs. WR.mIL2v A34-K151E + isotype mAb | WR.Luc-GFP A34-K151E + isotype mAb vs. WR.mIL2v A34-K151E + isotype mAb | Vehicle + anti-PD1 mAb vs. WR.Luc-GFP A34-K151E + anti-PD1 mAb | Vehicle + anti-PD1 mAb vs. WR.mIL2v A34-K151E + anti-PD1 mAb | WR.Luc-GFP A34-K151E + anti-PD1 mAb vs. WR.mIL2v A34-K151E + anti-PD1 mAb |
| Day 13 | **0.0128** | **<0.001** | **0.008** | **<0.001** | **<0.001** | 0.9208 |
| Day 17 | **0.0037** | **<0.001** | **<0.001** | **<0.001** | **<0.001** | **<0.001** |
| Day 20 | **0.0017** | **<0.001** | **<0.001** | **<0.001** | **<0.001** | **<0.001** |
| Day 24 | 0.1518 | **<0.001** | **<0.001** | 0.232 | **<0.001** | **<0.001** |
| Day 27 | 0.1917 | **<0.001** | **<0.001** | 0.144 | **<0.001** | **<0.001** |
| Day 31 | 0.3114 | **<0.001** | **<0.001** | 0.465 | **<0.001** | **<0.001** |

| Post-tumor cell implant time point | Vehicle + isotype mAb vs. Vehicle + anti-PD1 mAb | WR.Luc-GFP A34-K151E + isotype mAb vs. WR.Luc-GFP A34-K151E + anti-PD1 mAb | WR.mIL2v A34-K151E + isotype mAb vs. WR.mIL2v A34-K151E + anti-PD1 mAb | | | |
|---|---|---|---|---|---|---|
| Day 13 | 0.370 | **<0.001** | 0.459 | | | |
| Day 17 | 0.476 | **0.002** | **0.048** | | | |
| Day 20 | 0.101 | 0.061 | 0.084 | | | |
| Day 24 | 0.119 | 0.190 | **0.014** | | | |
| Day 27 | 0.143 | 0.100 | **0.007** | | | |
| Day 31 | 0.301 | 0.432 | **0.012** | | | |

FIG. 33A (Table 10)

| | Mean serum cytokine levels ± SEM (One-way ANOVA results: p-value represents Tukey's post-hoc comparisons) | | | | | | | |
|---|---|---|---|---|---|---|---|---|
| | Human IL-2 or IL-2v (ng/mL) | Mouse IL-1β (ng/mL) | Mouse IL-6 (ng/mL) | Mouse IL-10 (ng/mL) | Mouse IL-12p70 (ng/mL) | Mouse IFN-α (ng/mL) | Mouse IFN-γ (ng/mL) | Mouse TNF-α (ng/mL) |
| Vehicle | 1.3 ± 0.4 | 0.9 ± 0.1 | 14 ± 3 | 4.5 ± 0.7 | 118 ± 22 | 226 ± 62 | 0.5 ± 0.1 | 6.6 ± 0.2 |
| WR Luc-2A-GFP (VV3) | 1.6 ± 0.7 ($p>0.05$) | 1.8 ± 0.2 ($p<0.01$)[a] | 247 ± 36 ($p<0.001$)[a] | 31 ± 3 ($p<0.001$)[a] | 269 ± 32 ($p<0.001$)[a] | 174 ± 61 ($p>0.05$) | 69 ± 12 ($p<0.001$)[a] | 20 ± 2 ($p<0.001$)[a] |
| WR hIL-2 (VV99) | 4689 ± 1682 ($p<0.001$)[b] | 22 ± 4 ($p<0.001$)[d] | 541 ± 74 ($p<0.001$)[b] ($p<0.01$)[c] | 215 ± 30 ($p<0.001$)[d] | 2539 ± 127 ($p<0.001$)[d] | 285 ± 67 ($p>0.05$) | 735 ± 322 ($p<0.001$)[d] | 59 ± 5 ($p<0.001$)[d] |
| WR hIL-2v (VV100) | 4674 ± 927 ($p<0.001$)[b] | 1.7 ± 0.4 ($p=0.03$)[a] | 213 ± 29 ($p<0.001$)[a] | 28 ± 2 ($p<0.001$)[a] | 278 ± 28 ($p<0.001$)[a] | 279 ± 87 ($p>0.05$) | 86 ± 28 ($p<0.001$)[a] | 19 ± 1 ($p<0.001$)[a] |

(a) p-value represents post-hoc comparison vs. Vehicle group
(b) p-value represents post-hoc comparison vs. Vehicle and VV3 groups
(c) p-value represents post-hoc comparison vs. VV3 and VV100 groups
(d) p-value represents post-hoc comparison vs. Vehicle, VV3 and VV100 groups

FIG. 33B (Table 11)

| Treatment | Fold increase in serum cytokine levels over vehicle treatment (Percent reduction from WR hIL-2) | | | | | | | |
|---|---|---|---|---|---|---|---|---|
| | Human IL-2 or IL-2v (ng/mL) | Mouse IL-1β (ng/mL) | Mouse IL-6 (ng/mL) | Mouse IL-10 (ng/mL) | Mouse IL-12p70 (ng/mL) | Mouse IFN-α (ng/mL) | Mouse IFN-γ (ng/mL) | Mouse TNF-α (ng/mL) |
| WR Luc-2A-GFP (VV3) | 1.2x | 2.0x | 17.6x | 6.9x | 2.3x | 0.8x | 138.0x | 3.0x |
| WR hIL-2 (VV99) | 3606.9x | 24.4x | 38.6x | 47.8x | 21.5x | 1.3x | 1470.0x | 8.9x |
| WR hIL-2v (VV100) | 3595.4x (0%) | 1.9x (92%) | 15.2x (61%) | 6.2x (87%) | 2.4x (89%) | 1.2x (2%) | 172.0x (88%) | 2.9x (68%) |

RECOMBINANT VACCINIA VIRUS AND METHODS OF USE THEREOF

CROSS REFERENCE TO RELATED APPLICATIONS

The present application claims the benefit of priority to U.S. Provisional Application No. 62/797,287, filed on Jan. 14, 2019, U.S. Provisional Application No. 62/854,121, filed on May 29, 2019, and to U.S. Provisional Application No. 62/886,727, filed on Aug. 14, 2019.

INCORPORATION BY REFERENCE OF SEQUENCE LISTING PROVIDED AS A TEXT FILE

A Sequence Listing is provided herewith as a text file, "PC40316_SequenceListing_ST25.txt" created on Dec. 11, 2019 and having a size of 56 KB. The contents of the text file are incorporated by reference herein in their entirety.

INTRODUCTION

Oncolytic viruses (OVs) are viruses that selectively replicate in cancer cells. Live replicating OVs have been tested in clinical trials in a variety of human cancers. OVs can induce anti-tumor immune responses, as well as direct lysis of tumor cells. Common OVs include attenuated strains of Herpes Simplex Virus (HSV), Adenovirus (Ad), Measles Virus (MV), Coxsackie virus (CV), Vesicular Stomatitis Virus (VSV), and Vaccinia Virus (VV).

Vaccinia virus replicates in the cytoplasm of a host cell. The large vaccinia virus genome codes for various enzymes and proteins used for viral DNA replication. During replication, vaccinia produces several infectious forms which differ in their outer membranes: the intracellular mature virion (IMV), the intracellular enveloped virion (IEV), the cell-associated enveloped virion (CEV) and the extracellular enveloped virion (EEV). IMV is the most abundant infectious form and is thought to be responsible for spread between hosts; the CEV is believed to play a role in cell-to-cell spread; and the EEV is thought to be important for long range dissemination within the host organism.

SUMMARY

The present disclosure provides a replication-competent, recombinant oncolytic vaccinia virus comprising a nucleotide sequence encoding a variant interleukin-2 (IL-2v) polypeptide; and compositions comprising the replication-competent, recombinant oncolytic vaccinia virus. The present disclosure provides methods of inducing oncolysis in an individual having a tumor, the methods comprising administering to the individual an effective amount of a replication-competent, recombinant oncolytic vaccinia virus of the present disclosure or a composition of the present disclosure.

BRIEF DESCRIPTION OF THE DRAWINGS

FIG. 1 provides amino acid sequences of the mature and precursor forms of wild-type human IL-2 (hIL-2).

FIG. 2 provides amino acid sequences of the mature and precursor forms of wild-type mouse IL-2 (mIL-2).

FIG. 4 provides Table 1, which presents a statistical comparison of virotherapy-induced tumor growth inhibition using analysis of covariance (ANCOVA).

FIGS. 9A-9F depict kinetic immunophenotype profiling of tumor infiltrating lymphocyte (TIL) populations following IT treatment with 1e5 plaque forming units (pfu) (FIGS. 9A-9C) or 1e7 pfu (FIGS. 9D-9F) transgene-armed Cop vaccinia virus.

FIGS. 10A-10I depicts assessment of virotherapy-induced tumor growth inhibition on C57BL/6 female mice implanted SC with MC38 tumor cells.

FIG. 11 provides Table 2, which presents a statistical comparison of virotherapy-induced tumor growth inhibition using ANCOVA.

FIG. 17 presents Table 4, which provides a statistical comparison of virotherapy-induced tumor growth inhibition using ANCOVA for the subcutaneous LLC tumor model study presented in FIGS. 16A-16E.

FIG. 21 presents Table 5, which provides a statistical comparison of virotherapy-induced tumor growth inhibition using ANCOVA for the subcutaneous MC38 tumor model study depicted in FIGS. 20A-20H.

FIG. 24 presents Table 6, which provides a statistical comparison of IL-2 levels detected in sera collected from groups of MC38 tumor-bearing mice given one or three separate IV doses of reporter or mIL-2v transgene-armed WR virus (presented in FIG. 23).

FIGS. 25A-25I depict an assessment of a recombinant oncolytic vaccinia virus of the present disclosure on tumor growth in vivo using IV delivery into C57BL/6 female mice implanted SC with LLC tumor cells.

FIG. 26 presents Table 7, which provides a statistical comparison of virotherapy-induced tumor growth inhibition using ANCOVA for the subcutaneous LLC tumor model study depicted in FIGS. 25A-25I.

FIG. 28 presents Table 8, which provides a statistical comparison of IL-2 levels detected in sera collected from groups of LLC tumor-bearing mice given one, two or three separate IV doses of reporter or mIL-2v transgene-armed WR virus (presented in FIG. 27).

FIGS. 29A-29G depict an assessment of IV virotherapy (administration of a recombinant oncolytic vaccinia virus of the present disclosure) combined with checkpoint inhibitor therapy on tumor growth inhibition in C57BL/6 female mice implanted SC with MC38 tumor cells.

FIG. 30 presents Table 9, which provides a statistical comparison of virotherapy plus isotype or anti-PD1 mAb effect on tumor growth inhibition using ANCOVA for the subcutaneous MC38 tumor model study depicted in FIGS. 29A-29G.

FIGS. 33A and 33B presents Tables 10 and Table 11, which provide (A) mean serum cytokine levels following intravenous treatment of B16F10 tumor-bearing C57BL/6 mice with vehicle, wild-type hIL-2 or hIL-2v transgene-armed WR vaccinia viruses and (B) fold increase in cytokine levels over vehicle treatment for each virus treatment and the percent reduction in proinflammatory cytokine levels.

DEFINITIONS

Figure 3A:
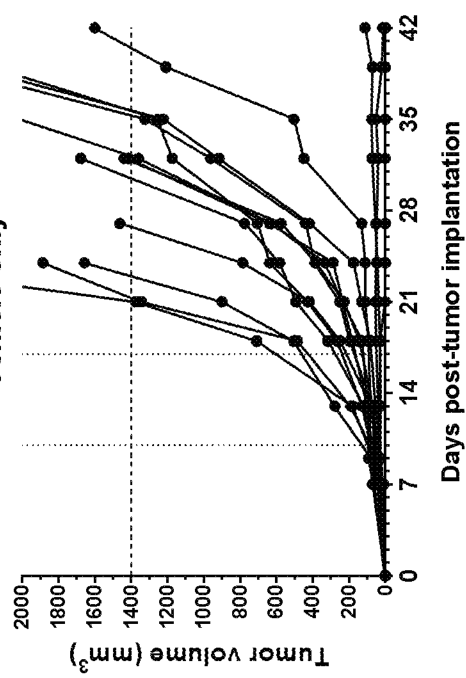
FIGS. 3A-3E depict assessment of oncolytic virus-induced tumor growth inhibition on C57BL/6 female mice implanted subcutaneously (s.c. or SC) with MC38 tumor cells.
Figure 3B:
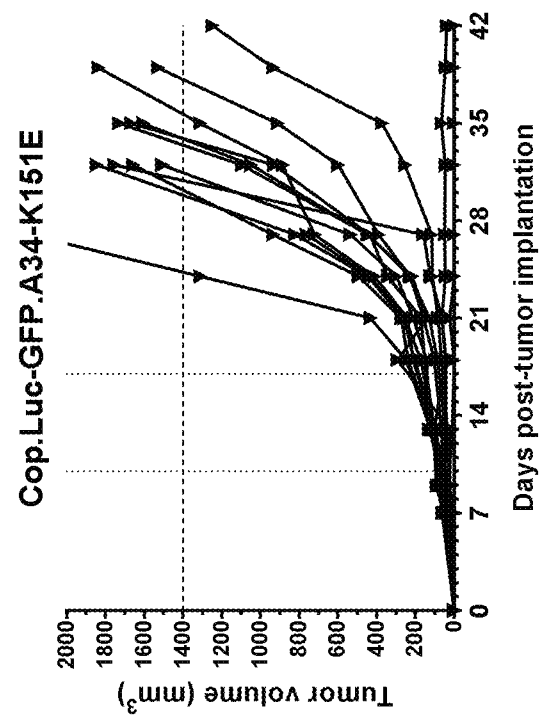
Figure 3C:
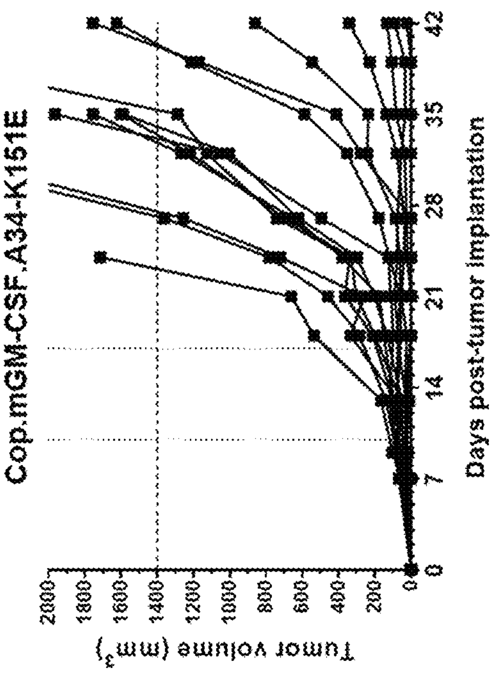
Figure 3D:
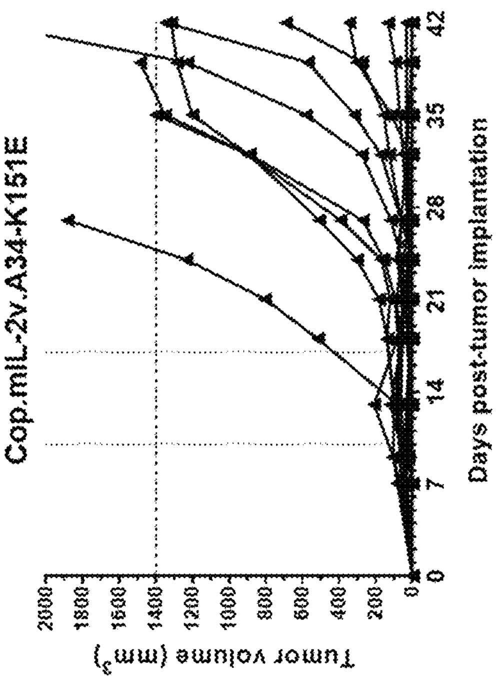
Figure 3E:
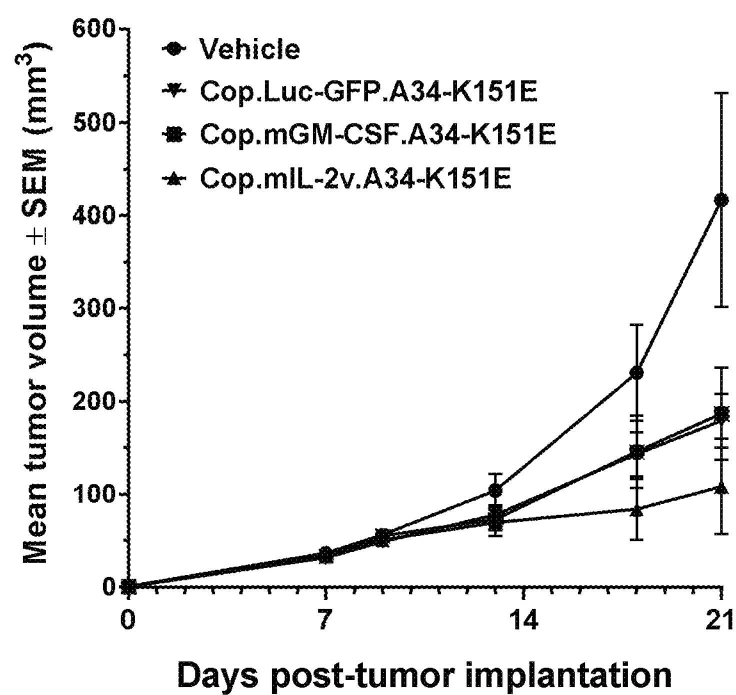

As used herein, an "oncolytic" vaccinia virus is a vaccinia virus that preferentially infects and kills cancer cells, compared to normal (non-cancerous) cells.

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, e.g., in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "individual," "subject," "host," and "patient," used interchangeably herein, refer to a mammal, including, but not limited to, murines (e.g., rats, mice), lagomorphs (e.g., rabbits), non-human primates, humans, canines, felines, ungulates (e.g., equines, bovines, ovines, porcines, caprines), etc.

A "therapeutically effective amount" or "efficacious amount" refers to the amount of an agent (e.g., a replication-competent, recombinant oncolytic vaccinia virus of the present disclosure), or combined amounts of two agents (e.g., a replication-competent, recombinant oncolytic vaccinia virus of the present disclosure and a second therapeutic agent), that, when administered to a mammal or other subject for treating a disease, is sufficient to effect such treatment for the disease. The "therapeutically effective amount" will vary depending on the agent(s), the disease and its severity and the age, weight, etc., of the subject to be treated.

The term "biological activity" refers to any cellular response that is the direct result of binding of a cytokine (e.g. IL-2 or IL-2v) to cell surface receptors coupled with initiation of intracellular signaling pathways.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a vaccinia virus" includes a plurality of such vaccinia viruses and reference to "the variant IL-2 polypeptide" includes reference to one or more variant IL-2 polypeptides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides a replication-competent, recombinant oncolytic vaccinia virus comprising a nucleotide sequence encoding a variant IL-2 polypeptide (IL-2v); and compositions comprising the replication-competent, recombinant oncolytic vaccinia virus. The present disclosure provides methods of inducing oncolysis in an individual having a tumor, the methods comprising administering to the individual an effective amount of a replication-competent, recombinant oncolytic vaccinia virus of the present disclosure or a composition of the present disclosure.

Oncolytic Vaccinia Virus

The present disclosure provides a replication-competent, recombinant oncolytic vaccinia virus comprising a nucleotide sequence encoding a variant interleukin-2 (IL-2v) polypeptide. The IL-2v polypeptide comprises an amino acid substitution that provides for reduced binding to CD25 (high-affinity IL-2 receptor cc subunit), compared to wild-type IL-2. The IL-2v polypeptide-encoding nucleotide sequence is present in the genome of the replication-competent, recombinant oncolytic vaccinia virus, and may be referred to as a "transgene." The IL-2v polypeptide-encoding nucleotide sequence is not normally present in wild-type vaccinia virus, and is thus heterologous to wild-type vaccinia virus. Thus, the IL-2v polypeptide-encoding nucleotide sequence can be referred to as a "heterologous nucleic acid comprising a nucleotide sequence encoding an IL-2v polypeptide." A virus comprising a transgene is said to be "armed" with the transgene. Thus, e.g., a replication-competent, recombinant oncolytic vaccinia virus of the present disclosure that comprises a nucleotide sequence encoding an IL-2v polypeptide is said to be "armed" with the IL-2v-encoding nucleotide sequence.

The amino acid sequence of the mature form of a wild-type human IL-2 (hIL-2) polypeptide (SEQ ID NO:1) is provided in FIG. 1. The amino acid sequence of the mature form of a wild-type mouse IL-2 (mIL-2) polypeptide (SEQ ID NO:23) is provided in FIG. 2. In some cases, an IL-2v polypeptide encoded by a replication-competent, recombinant oncolytic vaccinia virus of the present disclosure comprises an amino acid substitution that provides for reduced binding to CD25. In some cases, an IL-2v polypeptide encoded by a replication-competent, recombinant oncolytic vaccinia virus of the present disclosure comprises a substitution of one or more of F42, Y45, and L72, based on the amino acid numbering of the IL-2 amino acid sequence depicted in SEQ ID NO:1. In some cases, an IL-2v polypeptide encoded by a replication-competent, recombinant oncolytic vaccinia virus of the present disclosure comprises a substitution of one or more of F42 and Y45, based on the amino acid numbering of the IL-2 amino acid sequence depicted in SEQ ID NO:1. In some cases, an IL-2v polypeptide encoded by a replication-competent, recombinant oncolytic vaccinia virus of the present disclosure comprises a substitution of one or more of F42, and L72, based on the amino acid numbering of the IL-2 amino acid sequence depicted in SEQ ID NO:1. In some cases, an IL-2v polypeptide encoded by a replication-competent, recombinant oncolytic vaccinia virus of the present disclosure comprises a substitution of one or more of Y45, and L72, based on the amino acid numbering of the IL-2 amino acid sequence depicted in SEQ ID NO:1. In some cases, an IL-2v polypeptide encoded by a replication-competent, recombinant oncolytic vaccinia virus of the present disclosure comprises an F42L, F42A, F42G, F42S, F42T, F42Q, F42E, F42D, F42R, or F42K substitution, based on the amino acid numbering of the IL-2 amino acid sequence depicted in SEQ ID NO:1. In some cases, an IL-2v polypeptide encoded by a replication-competent, recombinant oncolytic vaccinia virus of the present disclosure comprises a Y45A, Y45G, Y45S, Y45T, Y45Q, Y45E, Y45N, Y45D, Y45R, or Y45K substitution, based on the amino acid numbering of the IL-2 amino acid sequence depicted in SEQ ID NO:1. In some cases, an IL-2v polypeptide encoded by a replication-competent, recombinant oncolytic vaccinia virus of the present disclosure comprises an L72G, L72A, L72S, L72T, L72Q, L72E, L72N, L72R, or L72K substitution, based on the amino acid numbering of the IL-2 amino acid sequence depicted in SEQ ID NO:1.

In some cases, an IL-2v polypeptide encoded by a replication-competent, recombinant oncolytic vaccinia virus of the present disclosure provides reduced biological activity when compared to wild-type IL-2. In some cases, said reduced biological activity is tested by measuring potency at inducing increased pSTAT5 levels in CD25+ CD4+ Treg cells when compared to wild-type IL-2, as disclosed at Example 8. In some cases, an IL-2v polypeptide encoded by a replication-competent, recombinant oncolytic vaccinia virus of the present disclosure provides reduced concentration potency when compared to wild-type IL-2 at inducing increased pSTAT5 levels in CD25+ CD4+ Treg cells (e.g. using the test disclosed at Example 8). In some cases, an IL-2v polypeptide encoded by a replication-competent, recombinant oncolytic vaccinia virus of the present disclosure provides reduced concentration potency of at least 1, at least 2 or at least 3 logs when compared to wild-type IL-2 at inducing increased pSTAT5 levels in CD25+ CD4+ Treg cells (e.g. using the test disclosed at Example 8). In some cases, an IL-2v polypeptide encoded by a replication-competent, recombinant oncolytic vaccinia virus of the present disclosure provides reduced concentration potency of about 1, about 2 or about 3 logs when compared to wild-type IL-2 at inducing increased pSTAT5 levels in CD25+ CD4+ Treg cells (e.g. using the test disclosed at Example 8).

In some cases, said reduced biological activity is tested by measuring the proinflammatory cytokine levels after treatment with an IL-2v polypeptide encoded by a replication-competent, recombinant oncolytic vaccinia virus when compared to wild-type IL-2, as disclosed at Example 9. In some cases, an IL-2v polypeptide encoded by a replication-competent, recombinant oncolytic vaccinia virus of the present disclosure provides reduced proinflammatory cytokine levels when compared to wild-type IL-2 (e.g. using the test disclosed at Example 9). In some cases, an IL-2v polypeptide encoded by a replication-competent, recombinant oncolytic vaccinia virus of the present disclosure provides reduced proinflammatory cytokine levels by at least 10%, at least 15%, at least 20%, at least 25%, at least 30%, at least 40%, at least 45%, at least 50%, at least 55%, at least 60%, at least 65%, at least 70%, at least 75%, at least 80%, at least 85%, at least 90%, at least 95%, or at least 100%, when compared to wild type IL-2 (e.g. using the test disclosed at Example 9).

The amino acid sequence of the precursor form of the wild-type hIL-2 polypeptide (SEQ ID NO:21) is provided in FIG. 1. The precursor form of the wild-type hIL-2 polypeptide includes a signal peptide (e.g., MYRMQLLSCIALSLALVTNS (SEQ ID NO:22)). The amino acid sequence of the precursor form of the mouse wild-type IL-2 polypeptide (SEQ ID NO:24) is provided in FIG. 2. In some cases, a replication-competent, recombinant oncolytic vaccinia virus of the present disclosure comprises a nucleotide sequence encoding an IL-2v polypeptide that includes a signal peptide (e.g., MYRMQLLSCIALSLALVTNS (SEQ ID NO:22). Thus, e.g., in some cases, a replication-competent, recombinant oncolytic vaccinia virus of the present disclosure comprises a nucleotide sequence encoding an IL-2v polypeptide having at least 95% (e.g., at least 95%, at least 98%, at least 99%, or 100%) amino acid sequence identity to the IL-2 amino acid sequence depicted in SEQ ID NO:21, and comprising a substitution of one or more of F42, Y45, and L72, based on the amino acid numbering of the IL-2 amino acid sequence depicted in SEQ ID NO:1. As will be appreciated, F42, Y45, and L72 of the IL-2 amino acid sequence depicted in SEQ ID NO: 1 correspond to F62, Y65, and L92 of the IL-2 amino acid sequence depicted in SEQ ID NO:21.

In some cases, an IL-2v polypeptide encoded by a replication-competent, recombinant oncolytic vaccinia virus of the present disclosure comprises one or more of: a) an F42L, F42A, F42G, F42S, F42T, F42Q, F42E, F42D, F42R, or F42K substitution; b) a Y45A, Y45G, Y45S, Y45T, Y45Q, Y45E, Y45N, Y45D, Y45R, or Y45K substitution; and c) an L72G, L72A, L72S, L72T, L72Q, L72E, L72N, L72R, or L72K substitution, based on the amino acid numbering of the IL-2 amino acid sequence depicted in SEQ ID NO:1. In some cases, an IL-2v polypeptide encoded by a replication-competent, recombinant oncolytic vaccinia virus of the present disclosure comprises: a) an F42L, F42A, F42G, F42S, F42T, F42Q, F42E, F42D, F42R, or F42K substitution; and b) an Y45A, Y45G, Y45S, Y45T, Y45Q, Y45E, Y45N, Y45D, Y45R, or Y45K substitution, based on the amino acid numbering of the IL-2 amino acid sequence depicted in SEQ ID NO:1. In some cases, an IL-2v polypeptide encoded by a replication-competent, recombinant oncolytic vaccinia virus of the present disclosure comprises: a) an F42L, F42A, F42G, F42S, F42T, F42Q, F42E, F42D, F42R, or F42K substitution; and b) an L72G, L72A, L72S, L72T, L72Q, L72E, L72N, L72R, or L72K substitution, based on the amino acid numbering of the IL-2 amino acid sequence depicted in SEQ ID NO:1. In some cases, an IL-2v polypeptide encoded by a replication-competent, recombinant oncolytic vaccinia virus of the present disclosure comprises: a) a Y45A, Y45G, Y45S, Y45T, Y45Q, Y45E, Y45N, Y45D, Y45R, or Y45K substitution; and b) an L72G, L72A, L72S, L72T, L72Q, L72E, L72N, L72R, or L72K substitution, based on the amino acid numbering of the IL-2 amino acid sequence depicted in SEQ ID NO: 1. In some cases, an IL-2v polypeptide encoded by a replication-competent, recombinant oncolytic vaccinia virus of the present disclosure comprises: a) an F42L, F42A, F42G, F42S, F42T, F42Q, F42E, F42D, F42R, or F42K substitution; b) a Y45A, Y45G, Y45S, Y45T, Y45Q, Y45E, Y45N, Y45D, Y45R, or Y45K substitution; and c) an L72G, L72A, L72S, L72T, L72Q, L72E, L72N, L72R, or L72K substitution, based on the amino acid numbering of the IL-2 amino acid sequence depicted in SEQ ID NO:1.

In some cases, the amino acid substitution that provides for reduced binding to CD25 is one or more of F42A, Y45A, and L72G, based on the amino acid numbering of the IL-2 amino acid sequence depicted in SEQ ID NO:1. In some cases, the amino acid substitution that provides for reduced binding to CD25 is one or more of F42A and Y45A, based on the amino acid numbering of the IL-2 amino acid sequence depicted in SEQ ID NO:1. In some cases, the amino acid substitution that provides for reduced binding to CD25 is F42A and L72G, based on the amino acid numbering of the IL-2 amino acid sequence depicted in SEQ ID NO:1. In some cases, the amino acid substitution that provides for reduced binding to CD25 is Y45A, and L72G, based on the amino acid numbering of the IL-2 amino acid sequence depicted in SEQ ID NO: 1. In some cases, the amino acid substitution that provides for reduced binding to CD25 is F42A, Y45A, and L72G, based on the amino acid numbering of the IL-2 amino acid sequence depicted in SEQ ID NO:1.

In some cases, an IL-2v polypeptide encoded by a replication-competent, recombinant oncolytic vaccinia virus of the present disclosure comprises an amino acid sequence having at least 95% (e.g., at least 95%, at least 98%, at least 99%, or 100%) amino acid sequence identity to the amino acid sequence depicted in SEQ ID NO:1, and comprises an F42A substitution, based on the amino acid numbering of the IL-2 amino acid sequence depicted in SEQ ID NO:1. In some cases, an IL-2v polypeptide encoded by a replication-competent, recombinant oncolytic vaccinia virus of the present disclosure comprises an amino acid sequence having at least 95% (e.g., at least 95%, at least 98%, at least 99%, or 100%) amino acid sequence identity to the amino acid sequence depicted in SEQ ID NO:1, and comprises a Y45A substitution, based on the amino acid numbering of the IL-2 amino acid sequence depicted in SEQ ID NO:1. In some cases, an IL-2v polypeptide encoded by a replication-competent, recombinant oncolytic vaccinia virus of the present disclosure comprises an amino acid sequence having at least 95% (e.g., at least 95%, at least 98%, at least 99%, or 100%) amino acid sequence identity to the amino acid sequence depicted in SEQ ID NO:1, and comprises an L72G substitution, based on the amino acid numbering of the IL-2 amino acid sequence depicted in SEQ ID NO:1. In some cases, an IL-2v polypeptide encoded by a replication-competent, recombinant oncolytic vaccinia virus of the present disclosure comprises an amino acid sequence having at least 95% (e.g., at least 95%, at least 98%, at least 99%, or 100%) amino acid sequence identity to the amino acid sequence depicted in SEQ ID NO:1, and comprises an F42A substitution and an L72G substitution, based on the amino acid numbering of the IL-2 amino acid sequence depicted in SEQ ID NO:1. In some cases, an IL-2v polypeptide encoded by a replication-competent, recombinant oncolytic vaccinia virus of the present disclosure comprises an amino acid sequence having at least 95% (e.g., at least 95%, at least 98%, at least 99%, or 100%) amino acid sequence identity to the amino acid sequence depicted in SEQ ID NO:1, and comprises an F42A substitution and a Y45A substitution based on the amino acid numbering of the IL-2 amino acid sequence depicted in SEQ ID NO:1. In some cases, an IL-2v polypeptide encoded by a replication-competent, recombinant oncolytic vaccinia virus of the present disclosure comprises an amino acid sequence having at least 95% (e.g., at least 95%, at least 98%, at least 99%, or 100%) amino acid sequence identity to the amino acid sequence depicted in SEQ ID NO:1, and comprises a Y45A substitution and an L72G substitution, based on the amino acid numbering of the IL-2 amino acid sequence depicted in SEQ ID NO:1. In some cases, an IL-2v polypeptide encoded by a replication-competent, recombinant oncolytic vaccinia virus of the present disclosure comprises an amino acid sequence having at least 95% (e.g., at least 95%, at least 98%, at least 99%, or 100%) amino acid sequence identity to the amino acid sequence depicted in SEQ ID NO:1, and comprises an F42A substitution, a Y45A substitution, and an L72G substitution, based on the amino acid numbering of the IL-2 amino acid sequence depicted in SEQ ID NO:1.

In some cases, an IL-2v polypeptide encoded by a replication-competent, recombinant oncolytic vaccinia virus of the present disclosure does not include a substitution of T3 and/or C125. In other words, in some cases, an IL-2v polypeptide encoded by a replication-competent, recombinant oncolytic vaccinia virus of the present disclosure comprises a Thr at amino acid position 3, and a Cys at amino acid position 125, based on the amino acid numbering of the IL-2 amino acid sequence depicted in SEQ ID NO:1.

The vaccinia virus used to construct a replication-competent, recombinant oncolytic vaccinia virus of the present disclosure can include attenuated and/or tumor-selective vaccinia viruses. As used herein, "attenuated" means low toxicity (for example, low virus replication, low cytolytic activity, low cytotoxic activity) to normal cells (for example, non-tumor cells). As used herein, "tumor selective" means toxicity to tumor cells (for example, oncolytic) higher than that to normal cells (for example, non-tumor cell). Vaccinia viruses genetically modified to be deficient in the function of a specific protein or to suppress the expression of a specific gene or protein (Guse et al. (2011) *Expert Opinion on Biological Therapy* 11:595) may be used in an oncolytic virus of the present disclosure. For example, in order to increase tumor selectivity of vaccinia virus, vaccinia virus deficient in the function of vaccinia growth factor (VGF) (McCart et al. (2001) *Cancer Research* 61:8751); vaccinia virus having a modified vaccinia virus TK gene, a modified hemagglutinin (HA) gene, and a modified F3 gene or an interrupted F3 locus (WO 2005/047458), vaccinia virus deficient in the function of VGF and O1L (WO 2015/076422); vaccinia virus in which a target sequence of a microRNA whose expression is decreased in cancer cells is inserted into the 3' noncoding region of the B5R gene (WO 2011/125469); HA and F14.5L (Zhang et al. (2007) *Cancer Research* 67:10038); vaccinia virus deficient in the function of B18R (Kirn et al. (2007) *PLoS Medicine* 4:e353); vaccinia virus deficient in the function of ribonucleotide reductase (Gammon et al. (2010) *PLoS Pathogens* 6:e1000984); vaccinia virus deficient in the function of serine protease inhibitor (e.g., SPI-1, SPI-2) (Guo et al. (2005) *Cancer Research* 65:9991); vaccinia virus deficient in the function of SPI-1 and SPI-2 (Yang et al. (2007) *Gene Therapy* 14:638); vaccinia virus deficient in the function of ribonucleotide reductase genes F4L or I4L (Child et al. (1990) *Virology* 174:625; Potts et al. (2017) *EMBO Mol. Med.* 9:638); vaccinia virus deficient in the function of B18R (B19R in Copenhagen strain) (Symons et al. (1995) *Cell* 81:551); vaccinia virus deficient in the function of A48R (Hughes et al. (1991) *J. Biol. Chem.* 266:20103); vaccinia virus deficient in the function of B8R (Verardi et al. (2001) *J. Virol.* 75:11); vaccinia virus deficient in the function of B15R (B16R in Copenhagen strain) (Spriggs et al. (1992) *Cell* 71:145); vaccinia virus deficient in the function of A41R (Ng et al. (2001) *Journal of General Virology* 82:2095); vaccinia virus deficient in the function of A52R (Bowie et al. (2000) *Proc. Natl. Acad. Sci. USA* 97:10162); vaccinia virus deficient in the function of F1L (Gerlic et al. (2013) *Proc. Natl. Acad. Sci. USA* 110:7808); vaccinia virus deficient in the function of E3L (Chang et al. (1992) *Proc. Natl. Acad. Sci. USA* 89:4825); vaccinia virus deficient in the function of A44R-A46R (Bowie et al. (2000) *Proc. Natl. Acad. Sci. USA* 97:10162); vaccinia virus deficient in the function of K1L (Bravo Cruz et al. (2017) *Journal of Virology* 91:e00524); vaccinia virus deficient in the function of A48R, B18R, C11R, and TK (Mejias-Perez et al. (2017) *Molecular Therapy: Oncolytics* 8:27); or vaccinia virus having mutations in the E3L and K3L regions (WO 2005/007824) may be used. Moreover, vaccinia virus deficient in the function of OIL may be used (Schweneker et al. (2012) *J. Virol.* 86:2323). Moreover, vaccinia virus deficient in the extracellular region of B5R (Bell et al. (2004) *Virology* 325:425) or vaccinia virus deficient in the A34R region (Thirunavukarasu et al. (2013) *Molecular Therapy* 21:1024) may be used. Moreover, vaccinia virus deficient in interleukin-1β (IL-1β) receptor (WO 2005/030971) may be used. Such insertion of a foreign gene or deletion or mutation of a gene can be made, for example, by a known homologous recombination or site-directed mutagenesis. Moreover, vaccinia virus having a combination of two or more of such genetic modifications may be used in a replication-competent, recombinant oncolytic vaccinia virus of the present disclosure.

As used herein, "being deficient" means that the gene region specified by this term has reduced or no function and includes a deficiency resulting from one or more of: i) mutation (e.g., substitution, inversion, etc.) and/or truncation and/or deletion of the gene region specified by this term; ii) mutation and/or truncation and/or deletion of a promoter region controlling expression of the gene region; and iii)

mutation and/or truncation and/or deletion of a polyadenylation sequence such that translation of a polypeptide encoded by the gene region is reduced or eliminated. A replication-competent, recombinant oncolytic vaccinia virus of the present disclosure that comprises a genetic alteration such that the replication-competent, recombinant oncolytic vaccinia virus is “deficient” in a given vaccinia virus gene exhibits reduced production and/or activity of a gene product (e.g., mRNA gene product; polypeptide gene product) of the gene; for example, the amount and/or activity of the gene product is less than 75%, less than 60%, less than 50%, less than 40%, less than 30%, less than 25%, less than 20%, less than 15%, less than 10%, less than 5%, or less than 1% of the amount and/or activity of the same gene product produced by wild-type vaccinia virus, or by a control vaccinia virus that does not comprise the genetic alteration. For example, “being deficient” may be a result of the deletion in a region consisting of the specified gene region or the deletion in a neighboring gene region comprising the specified gene region. As an example, a mutation and/or truncation and/or deletion of a promoter region that reduces transcription of a gene region can result in deficiency. A gene region can also be rendered deficient through incorporation of a transcriptional termination element such that translation of a polypeptide encoded by the gene region is reduced or eliminated. A gene region can also be rendered deficient through use of a gene-editing enzyme or a gene-editing complex (e.g., a CRISPR/Cas effector polypeptide complexed with a guide RNA) to reduce or eliminate transcription of the gene region. A gene region can also be rendered deficient through use of competitive reverse promoter/polymerase occupancy to reduce or eliminate transcription of the gene region. A gene region can also be rendered deficient by insertion of a nucleic acid into the gene region, thereby knocking out the gene region.

A replication-competent, recombinant oncolytic vaccinia virus of the present disclosure will in some instances lack vaccinia virus thymidine kinase (TK) activity. In some cases, a replication-competent, recombinant oncolytic vaccinia virus of the present disclosure comprises a deletion of all or a portion of the vaccinia virus TK coding region, such that the replication-competent, recombinant oncolytic vaccinia virus is TK deficient. For example, in some cases, a replication-competent, recombinant oncolytic vaccinia virus of the present disclosure comprises a J2R deletion. See, e.g., Mejia-Perez et al. (2018) *Mol. Ther. Oncolytics* 8:27. In some cases, a replication-competent, recombinant oncolytic vaccinia virus of the present disclosure comprises an insertion into the J2R region, thereby resulting in reduced or no vaccinia virus TK activity.

A replication-competent, recombinant oncolytic vaccinia virus of the present disclosure will in some instances comprise an A34R gene comprising a K151E substitution (i.e., comprising a modification that provides for a K151E substitution in the encoded polypeptide). See, e.g., Blasco et al. (1993) J. Virol. 67(6):3319-3325; and Thirunavukarasu et al. (2013) *Mol. Ther.* 21:1024. The A34R gene encodes vaccinia virus gp22-24.

A replication-competent, recombinant oncolytic vaccinia virus of the present disclosure can be constructed from any of a variety of strains of vaccinia virus. Strains of the vaccinia virus suitable for use include, but not limited to, the strains Lister, New York City Board of Health (NYBH), Wyeth, Copenhagen, Western Reserve (WR), Modified Vaccinia Ankara (MVA), EM63, Ikeda, Dalian, LIVP, Tian Tan, IHD-J, Tashkent, Bern, Paris, Dairen and derivatives the like. In some cases, a replication-competent, recombinant oncolytic vaccinia virus of the present disclosure is a Copenhagen strain vaccinia virus. In some cases, a replication-competent, recombinant oncolytic vaccinia virus of the present disclosure is a WR strain vaccinia virus.

The nucleotide sequences of the genomes of vaccinia viruses of various strains are known in the art. See, e.g., Goebel et al. (1990) *Virology* 179:247; Goebel et al. (1990) *Virology* 179:517. The nucleotide sequence of the Copenhagen strain vaccinia virus is known; see, e.g., GenBank Accession No. M35027. The nucleotide sequence of the WR strain vaccinia virus is known; see, e.g., GenBank Accession No. AY243312; and GenBank Accession No. NC_006998. The WR strain of vaccinia virus is available from the American Type Culture Collection (ATCC); ATCC VR-1354.

A replication-competent, recombinant oncolytic vaccinia virus of the present disclosure exhibits oncolytic activity. Examples of methods for evaluating whether a given virus exhibits oncolytic activity include a method for evaluating decrease of the survival rate of cancer cells by the addition of the virus. Examples of cancer cells to be used for the evaluation include the malignant melanoma cell RPMI-7951 (for example, ATCC HTB-66), the lung adenocarcinoma HCC4006 (for example, ATCC CRL-2871), the lung carcinoma A549 (for example, ATCC CCL-185), the lung carcinoma HOP-62 (for example, DCTD Tumor Repository), the lung carcinoma EKVX (for example, DCTD Tumor Repository), the small cell lung cancer cell DMS 53 (for example, ATCC CRL-2062), the lung squamous cell carcinoma NCI-H226 (for example, ATCC CRL-5826), the kidney cancer cell Caki-1 (for example, ATCC HTB-46), the bladder cancer cell 647-V (for example, DSMZ ACC 414), the head and neck cancer cell Detroit 562 (for example, ATCC CCL-138), the breast cancer cell JIMT-1 (for example, DSMZ ACC 589), the breast cancer cell MDA-MB-231 (for example, ATCC HTB-26), the breast cancer cell MCF7 (for example, ATCC HTB-22), the breast cancer HS-578T (for example, ATCC HTB-126), the breast ductal carcinoma T-47D (for example, ATCC HTB-133), the esophageal cancer cell 0E33 (for example, ECACC 96070808), the glioblastoma U-87MG (for example, ECACC 89081402), the neuroblastoma GOTO (for example, JCRB JCRB0612), the myeloma RPMI 8226 (for example, ATCC CCL-155), the ovarian cancer cell SK-OV-3 (for example, ATCC HTB-77), the ovarian cancer cell OVMANA (for example, JCRB JCRB1045), the cervical cancer HeLa (for example, ATCC CCL-2), the colon cancer cell RKO (for example, ATCC CRL-2577), the colon cancer cell HT-29 (for example, ATCC HTB-38), the colon cancer Colo 205 (for example, ATCC CCL-222), the colon cancer SW620 (for example, ATCC CCL-227), the colorectal carcinoma HCT 116 (for example, ATCC CCL-247), the pancreatic cancer cell BxPC-3 (for example, ATCC CRL-1687), the bone osteosarcoma U-2 OS (for example, ATCC HTB-96), the prostate cancer cell LNCaP clone FGC (for example, ATCC CRL-1740), the hepatocellular carcinoma JHH-4 (for example, JCRB JCRB0435), the mesothelioma NCI-H28 (for example, ATCC CRL-5820), the cervical cancer cell SiHa (for example, ATCC HTB-35), and the gastric cancer cell Kato III (for example, RIKEN BRC RCB2088).

A nucleic acid comprising a nucleotide sequence encoding an IL-2v polypeptide can be introduced into vaccinia virus using established techniques. An example of a suitable technique is reactivation with helper virus. Another example of a suitable technique is as homologous recombination. For example, a plasmid (also referred to as transfer vector plasmid DNA) in which a nucleic acid comprising a nucleotide sequence encoding an IL-2v polypeptide is inserted can be generated, generating a recombinant transfer vector; the recombinant transfer vector can be introduced into cells infected with vaccinia virus. The nucleic acid comprising a nucleotide sequence encoding the IL-2v polypeptide is then introduced into the vaccinia virus from the recombinant transfer vector via homologous recombination. The region in which a nucleic acid comprising a nucleotide sequence encoding an IL-2v polypeptide is introduced can be a gene region that is inessential for the life cycle of vaccinia virus. For example, the region in which a nucleic acid comprising a nucleotide sequence encoding an IL-2v polypeptide is introduced can be a region within the VGF gene in vaccinia virus deficient in the VGF function, a region within the OIL gene in vaccinia virus deficient in the OIL function, or a region or regions within either or both of the VGF and OIL genes in vaccinia virus deficient in both VGF and O1L functions. In the above, the foreign gene(s) can be introduced so as to be transcribed in the direction same as or opposite to that of the VGF and OIL genes. As another example, the region in which a nucleic acid comprising a nucleotide sequence encoding an IL-2v polypeptide is introduced can be a region within the B18 gene (B19 in Copenhagen) in vaccinia virus deficient in B18 (B19) function.

In some case, the nucleotide sequence encoding the IL-2v polypeptide is operably linked to a transcriptional control element, e.g., a promoter. In some cases, the promoter provides for expression of the IL-2v polypeptide in tumor cells. Suitable promoters include, but are not limited to, a pSEL promoter, a PSFJ1-10 promoter, a PSFJ2-16 promoter, a pHyb promoter, a Late-Early optimized promoter, a p7.5K promoter, a p11K promoter, a T7.10 promoter, a CPX promoter, a modified H5 promoter, an H4 promoter, a HF promoter, an H6 promoter, and a T7 hybrid promoter.

In some cases, the nucleotide sequence encoding the IL-2v polypeptide is operably linked to a regulatable promoter. In some cases, the regulatable promoter is a reversible promoter. In some cases, the nucleotide sequence encoding the IL-2v polypeptide is operably linked to a tetracycline-regulated promoter, (e.g., a promoter system such as TetActivators, TetON, TetOFF, Tet-On Advanced, Tet-On 3G, etc.). In some cases, the nucleotide sequence encoding the IL-2v polypeptide is operably linked to a repressible promoter. In some cases, the nucleotide sequence encoding the IL-2v polypeptide is operably linked to a promoter that is tetracycline repressible, e.g., the promoter is repressed in the presence of tetracycline or a tetracycline analog or derivative. In some cases, the nucleotide sequence encoding the IL-2v polypeptide is operably linked to a TetOFF promoter system. Bujard and Gossen (1992) *Proc. Natl. Acad. Sci. USA* 89:5547. For example, a TetOFF promoter system is repressed (inactive) in the presence of tetracycline (or suitable analog or derivative, such as doxycycline); once tetracycline is removed, the promoter is active and drives expression of the IL-2v polypeptide. In some cases, the nucleotide sequence encoding the IL-2v polypeptide is operably linked to a promoter that is tetracycline activatable, e.g., the promoter is activated in the presence of tetracycline or a tetracycline analog or derivative.

Exemplary Sequences

As noted above, a replication-competent, recombinant oncolytic vaccinia virus comprises a nucleic acid comprising a nucleotide sequence encoding an IL-2v polypeptide.

Suitable amino acid sequences of IL-2v polypeptides include, e.g., a mouse IL-2v polypeptide comprising an amino acid sequence having at least 95% (e.g., at least 95%, at least 98%, at least 99%, or 100%) amino acid sequence identity to the following amino acid sequence:

MYSMQLASCVTLTLVLLVNSAPTSSSTSSSTAEAQQQQQQQQQQQHLEQLLMDL QELLSRMENYRNLKLPRMLTAKFALPKQATELKDLQCLEDELGPLRHVLDGTQSKS FQLEDAENFISNIRVTVVKLKGSDNTFECQFDDESATVVDFLRRWIAFCQSIISTSPQ (SEQ ID NO:3), and comprising F76A, Y79A, and L106G substitutions (i.e., comprising Ala-76, Ala-79, and Gly-106).

Suitable nucleotide sequences encoding an IL-2v polypeptide include, e.g., a nucleotide sequence encoding a mouse IL-2v polypeptide and having at least 95% (e.g., at least 95%, at least 98%, at least 99%, or 100%) nucleotide sequence identity to the following nucleotide sequence:

ATGTACAGCATGCAGCTGGCCAGCTGCGTGACAC TGACCCTCGTGCTGCTGGTG AACAGCGCTCCTACCTCCTCCAGCACCAGCAGCAGCACCGCTGAGGCCCAGCAG CAGCAGCAGCAACAGCAACAGCAGCAACAACATTTAGAACAGCTGCTGATGGA TTTACAAGAACTGCTGTCTCGTATGGAGAACTATCGTAATTTAAAGCTGCCTCGT ATGCTGACCGCCAAGTTCGCTTTACCCAAGCAAGCTACAGAGCTGAAGGATTTA CAGTGTTTAGAGGACGAGCTGGGCCCTCTGAGGCATGTGCTGGACGGCACCCAG AGCAAGAGCTTCCAGCTGGAGGACGCCGAGAACTTTATCAGCAACATTCGTGTG ACCGTGGTGAAGCTGAAGGGCAGCGACAACACCTTCGAGTGCCAGTTCGACGAC GAGAGCGCCACAGTGGTGGACTTTTTAAGAAGGTGGATCGCCTTCTGCCAGTCC ATCATCAGCACCAGCCCCCAG (SEQ ID NO:2), where the encoded IL-2v polypeptide comprises F76A, Y79A, and L106G substitutions (i.e., comprises Ala-76, Ala-79, and Gly-106). This sequence is codon optimized for expression in mouse.

In some cases, a nucleotide sequence encoding a mouse IL-2v polypeptide is codon optimized for vaccinia virus. The following is a non-limiting example of a nucleotide sequence encoding a mouse IL-2v polypeptide that codon optimized for vaccinia virus:

```
                                                (SEQ ID NO: 19)
ATGTACTCGATGCAGTTAGCTTCCTGCGTGACCCTAACCTTAGTCTTGCTA

GTGAATTCGGCGCCCACCTCATCCTCAACGTCATCTTCCACAGCGGAGGCT

CAACAGCAGCAGCAACAGCAGCAACAACAACAGCAGCATTTGGAACAATTG

CTAATGGACTTACAGGAACTACTATCAAGAATGGAGAATTATCGAAACCTA

AAGTTACCTCGAATGTTGACAGCAAAATTTGCGTTGCCAAAGCAGGCCACA

GAGCTAAAGGACCTACAGTGTCTTGAAGATGAGCTAGGACCACTTCGTCAC

GTTTTAGACGGAACACAGTCCAAGTCTTTTCAGTTGGAAGACGCCGAGAAC

TTTATATCTAACATACGTGTTACTGTCGTAAAACTTAAAGGATCGGACAAT

ACTTTCGAATGCCAATTCGATGATGAAAGTGCAACCGTCGTGGACTTCTTG

CGACGTTGGATCGCCTTCTGTCAAAGTATAATTTCCACTTCGCCACAG.
```

Suitable amino acid sequences of IL-2v polypeptides include, e.g., a human IL-2v polypeptide comprising an amino acid sequence having at least 95% (e.g., at least 95%, at least 98%, at least 99%, or 100%) amino acid sequence identity to the following amino acid sequence:

MYRMQLLSCIALSLALVTN- SAPTSSSTKKTQLQLEHLLLDLQMILNGIN- NYKNPKLT RMLTAKF AMPKKATELKHLQCLEEELKPLEEVLN GAQSKNFHLRPRDLISNINVIVL ELKGSETTFMC- EYADETATIVEFLNRWITFCQSIISTLT (SEQ ID NO:14), and comprising F62A, Y65A, and L92G substitutions (i.e., comprising Ala-62, Ala-65, and Gly-92).

Suitable nucleotide sequences encoding an IL-2v polypeptide include, e.g., a nucleotide sequence encoding a human IL-2v polypeptide and having at least 80%, at least 85%, at least 90%, at least 95%, at least 98%, at least 99%, or 100%, nucleotide sequence identity to the following nucleotide sequence:

ATGTATCGTATGCAGCTGCTGAGCTGCATCGCTT- TATCTTTAGCTTTAGTGACCA ACAGCGCCCC- TACCAGCTCCTCCACCAAGAA- GACCCAGCTGCAGCTGGAGCATT TACTGCTGGATTTACAGATGATTTTAAACGG- CATCAACAACTACAAGAACCCCA AGCTGACTCGTATGCTGACCGCCAAGTTCGC- TATGCCCAAGAAGGCCACCGAGC TGAAGCACCTCCAGTGTTTAGAGGAGGAGCT- GAAGCCTTTAGAGGAGGTGCTGA ATG- GAGCCCAGAGCAAGAATTTCCATT- TAAGGCCTCGTGATTTAATCAGCAACA TCAACGTGATCGTGCTGGAGCT- GAAAGGCTCCGAGACCACCTTCATGTGCGAGT ACGCCGACGAGACCGCCACCATCGTG- GAGTTTTTAAATCGTTGGATCACCTTCTG CCAGAGCATCATCAGCACTTTAACC (SEQ ID NO:12), where the encoded IL-2v polypeptide comprises F62A, Y65A, and L92G substitutions (i.e., comprises Ala-62, Ala-65, and Gly-92). In some cases, the nucleotide sequence is human codon optimized. SEQ ID NO:12 is an example of a human codon-optimized IL-2v-encoding nucleotide sequence.

Suitable nucleotide sequences encoding an IL-2v polypeptide include, e.g., a nucleotide sequence encoding a human IL-2v polypeptide and having at least 80%, at least 85%, at least 90%, at least 95%, at least 98%, at least 99%, or 100%, nucleotide sequence identity to the following nucleotide sequence:

ATGTATCGAATGCAAT- TACTTTCCTGTATCGCACTTTCATT- AGCCCTTGTGACCA ACTCAGCGCCAACAT- CAAGTTCGACCAAGAAGACGCAGTTGCAGCT- AGAGCATT TGCTTTTGGATCTTCAAATGATCCT- TAATGGTATAAATAATTATAAGAACCCCAA ATTGACGCGAATGCTAACAGCTAAAT- TCGCAATGCCAAAGAAGGCAACCGAGTT AAAGCACCTACAATGCTTG- GAAGAAGAACTAAAACCCCTTGAGGAGGTAT- TAAA TGGTGCTCAGTCGAAGAATTTT- CATCTTCGACCTCGAGACCTAATTTCAAATATT AACGTAATTGTTTTGGAATTAAAGGGTTCG- GAAACTACTTTTATGTGTGAGTACG CAGACGAGACAGCTACAATAGTGGAGTTTCT- TAACCGTTGGATAACCTTTTGTCA ATCAATCAT- TTCGACTTTGACC (SEQ ID NO:13), where the encoded IL-2v polypeptide comprises F62A, Y65A, and L92G substitutions (i.e., comprises Ala-62, Ala-65, and Gly-92). In some cases, the nucleotide sequence is codon optimized for vaccinia virus. SEQ ID NO:13 is an example of a vaccinia virus codon-optimized IL-2v-encoding nucleotide sequence.

Suitable amino acid sequences of IL-2v polypeptides include, e.g., a human IL-2v polypeptide comprising an amino acid sequence having at least 95% (e.g., at least 95%, at least 98%, at least 99%, or 100%) amino acid sequence identity to the following amino acid sequence:

APTSSSTKKTQLQLEHLLLDLQMILNGIN- NYKNPKLTRMLTAKFAMPKKATELKHL QCLEEELKPLEEVLN GAQSKNFHLRPRDLISNINVIVLELKGSETTFMC- EYADETATI VEFLNRWITFCQSIISTLT (SEQ ID NO:9), and comprising F42A, Y45A, and L72G substitutions (i.e., comprising Ala-42, Ala-45, and Gly-72).

Suitable nucleotide sequences encoding an IL-2v polypeptide include, e.g., a nucleotide sequence encoding a human IL-2v polypeptide and having at least 80%, at least 85%, at least 90%, at least 95%, at least 98%, at least 99%, or 100%, nucleotide sequence identity to the following nucleotide sequence:

GCCCCTACCAGCTCCTCCACCAAGAA- GACCCAGCTGCAGCTGGAGCATTTACTG CTG- GATTTACAGATGATTTTAAACGGCAT- CAACAACTACAAGAACCCCAAGCTG ACTCGTATGCTGACCGCCAAGTTCGCTATGCC- CAAGAAGGCCACCGAGCTGAAG CACCTCCAGTGTTTAGAGGAGGAGCT- GAAGCCTTTAGAGGAGGTGCTGAATGGA GCCCAGAGCAAGAATTTCCATT- TAAGGCCTCGTGATTTAATCAGCAACATCAAC GTGATCGTGCTGGAGCTGAAAGGCTCCGA- GACCACCTTCATGTGCGAGTACGCC GACGA- GACCGCCACCATCGTGGAGTTTT- TAAATCGTTGGATCACCTTCTGCCAGA GCATCATCAGCACTTTAACC (SEQ ID NO:10), where the encoded IL-2v polypeptide comprises F42A, Y45A, and L72G substitutions (i.e., comprises Ala-42, Ala-45, and Gly-72). In some cases, the nucleotide sequence is human codon optimized. SEQ ID NO:10 is an example of a human codon-optimized IL-2v-encoding nucleotide sequence.

Suitable nucleotide sequences encoding an IL-2v polypeptide include, e.g., a nucleotide sequence encoding a human IL-2v polypeptide and having at least 80%, at least 85%, at least 90%, at least 95%, at least 98%, at least 99%, or 100%, nucleotide sequence identity to the following nucleotide sequence:

GCGCCAACATCAAGTTCGACCAAGAA- GACGCAGTTGCAGCTAGAGCATT TGCTTTTG- GATCTTCAAATGATCCTTAATGGTATAAATAAT- TATAAGAAC CCCAAATTGACGCGAATGCTAACAGCTAAAT- TCGCAATGCCAAAGAAGG CAACCGAGT- TAAAGCACCTACAATGCTTG- GAAGAAGAACTAAAACCCCT TGAGGAGGTAT- TAAATGGTGCTCAGTCGAAGAATTTT- CATCTTCGACCTC GAGACCTAATTTCAAATAT- TAACGTAATTGTTTTGGAATTAAAGGGTTCG GAAACTACTTTTATGTGTGAGTACGCAGACGA- GACAGCTACAATAGTGG AGTTTCT- TAACCGTTGGATAACCTTTTGTCAATCAATCAT- TTCGACTTTGA CC (SEQ ID NO:11), where the encoded IL-2v polypeptide comprises F42A, Y45A, and L72G substitutions (i.e., comprises Ala-42, Ala-45, and Gly-72). In some cases, the nucleotide sequence is codon optimized for vaccinia virus. SEQ ID NO:11 is an example of a vaccinia virus codon-optimized IL-2v-encoding nucleotide sequence.

In some cases, a replication-competent, recombinant oncolytic vaccinia virus of the present disclosure comprises a homologous recombination donor fragment encoding an IL-2v polypeptide, where the homologous recombination donor fragment comprises a nucleotide sequence having at least 80%, at least 85%, at least 90%, at least 95%, at least 98%, at least 99%, or 100%, nucleotide sequence identity to the nucleotide sequence set forth in any one of SEQ ID NO:4 (VV27/VV38 homologous recombination donor fragment), SEQ ID NO:5 (VV39 homologous recombination donor fragment), SEQ ID NO:15 (VV75 homologous recombination donor fragment containing hIL-2v (human codon optimized)), SEQ ID NO:16 (Copenhagen J2R homologous recombination plasmid containing hIL-2v (human codon optimized)), SEQ ID NO:17 (homologous recombination donor fragment containing hIL-2v (vaccinia virus codon optimized)), SEQ ID NO:18 (Copenhagen J2R homologous recombination plasmid containing hIL-2v (vaccinia virus codon optimized)), and SEQ ID NO:20 (mouse IL-2 variant (vaccinia virus codon optimized) homologous recombination donor fragment).

In some cases, a replication-competent, recombinant oncolytic vaccinia virus of the present disclosure comprises a nucleotide sequence having at least 80%, at least 85%, at least 90%, at least 95%, at least 98%, at least 99%, or 100%, nucleotide sequence identity to the nucleotide sequence set forth in SEQ ID NO:6 (Copenhagen J2R homologous recombination plasmid); and comprises a nucleic acid comprising a nucleotide sequence encoding an IL-2v polypeptide.

In some cases, a replication-competent, recombinant oncolytic vaccinia virus of the present disclosure comprises a nucleotide sequence having at least 80%, at least 85%, at least 90%, at least 95%, at least 98%, at least 99%, or 100%, nucleotide sequence identity to the nucleotide sequence set forth in SEQ ID NO:7 (Copenhagen J2R homologous recombination plasmid containing mouse IL-2 variant (mIL-2v) polypeptide). In some cases, the replication-competent, recombinant oncolytic vaccinia virus comprises, in place of the mIL-2v polypeptide, a human IL-2 variant (hIL-2v) polypeptide, as described above.

In some cases, a replication-competent, recombinant oncolytic vaccinia virus of the present disclosure comprises a nucleotide sequence having at least 80%, at least 85%, at least 90%, at least 95%, at least 98%, at least 99%, or 100%, nucleotide sequence identity to the nucleotide sequence set forth in SEQ ID NO:8 (Western Reserve J2R homologous recombination plasmid containing mIL-2v). In some cases, the replication-competent, recombinant oncolytic vaccinia virus comprises, in place of the mIL-2v polypeptide, a human IL-2 variant (hIL-2v) polypeptide, as described above.

In some cases, a replication-competent, recombinant oncolytic vaccinia virus of the present disclosure is VV27, (Copenhagen vaccinia containing A34R-K151E and mIL-2v transgene). In some cases, the replication-competent, recombinant oncolytic vaccinia virus comprises, in place of the mIL-2v polypeptide, a human IL-2 variant (hIL-2v) polypeptide, as described above.

In some cases, a replication-competent, recombinant oncolytic vaccinia virus of the present disclosure is VV38, (Copenhagen vaccinia containing mIL-2v transgene). In some cases, the replication-competent, recombinant oncolytic vaccinia virus comprises, in place of the mIL-2v polypeptide, a human IL-2 variant (hIL-2v) polypeptide, as described above.

In some cases, a replication-competent, recombinant oncolytic vaccinia virus of the present disclosure is VV39, (Western Reserve vaccinia containing mIL-2v transgene). In some cases, the replication-competent, recombinant oncolytic vaccinia virus comprises, in place of the mIL-2v polypeptide, a human IL-2 variant (hIL-2v) polypeptide, as described above.

Compositions

The present disclosure provides a composition, which may be a pharmaceutical composition, comprising a replication-competent, recombinant oncolytic vaccinia virus of the present disclosure. In some cases, the composition is a pharmaceutical composition. In some cases, the pharmaceutical composition is suitable for administering to an individual in need thereof, where the individual is a human.

A pharmaceutical composition comprising a replication-competent, recombinant oncolytic vaccinia virus of the present disclosure can optionally include a pharmaceutically acceptable carrier(s) that facilitate processing of an active ingredient into pharmaceutically acceptable compositions. As used herein, the term "pharmacologically acceptable carrier" refers to any carrier that has substantially no long-term or permanent detrimental effect when administered and encompasses terms such as "pharmacologically acceptable vehicle, stabilizer, diluent, auxiliary or excipient." Such a carrier generally is mixed with a replication-competent, recombinant oncolytic vaccinia virus of the present disclosure, and can be a solid, semi-solid, or liquid agent. It is understood that a replication-competent, recombinant oncolytic vaccinia virus of the present disclosure can be soluble or can be delivered as a suspension in the desired carrier or diluent. Any of a variety of pharmaceutically acceptable carriers can be used including, without limitation, aqueous media such as, e.g., distilled, deionized water, saline; solvents; dispersion media; coatings; antibacterial and antifungal agents; isotonic and absorption delaying agents; or any other inactive ingredient. Selection of a pharmacologically acceptable carrier can depend on the mode of administration. Except insofar as any pharmacologically acceptable carrier is incompatible with a replication-competent, recombinant oncolytic vaccinia virus of the present disclosure, its use in pharmaceutically acceptable compositions is contemplated. Non-limiting examples of specific uses of such pharmaceutical carriers can be found in "Pharmaceutical Dosage Forms and Drug Delivery Systems" (Howard C. Ansel et al., eds., Lippincott Williams & Wilkins Publishers, 7th ed. 1999); "Remington: The Science and Practice of Pharmacy" (Alfonso R. Gennaro ed., Lippincott, Williams & Wilkins, 20th 2000); "Goodman & Gilman's The Pharmacological Basis of Therapeutics" Joel G. Hardman et al., eds., McGraw-Hill Professional, 10th ed. 2001); and "Handbook of Pharmaceutical Excipients" (Raymond C. Rowe et al., APhA Publications, 4th edition 2003).

A subject pharmaceutical composition can optionally include, without limitation, other pharmaceutically acceptable components, including, without limitation, buffers, preservatives, tonicity adjusters, salts, antioxidants, physiological substances, pharmacological substances, bulking agents, emulsifying agents, wetting agents, and the like. Various buffers and means for adjusting pH can be used to prepare a pharmaceutical composition disclosed in the present specification, provided that the resulting preparation is pharmaceutically acceptable. Such buffers include, without limitation, acetate buffers, citrate buffers, phosphate buffers, neutral buffered saline, phosphate buffered saline and borate buffers. It is understood that acids or bases can be used to adjust the pH of a composition as needed. Pharmaceutically acceptable antioxidants include, without limitation, sodium metabisulfite, sodium thiosulfate, acetylcysteine, butylated hydroxyanisole and butylated hydroxytoluene. Useful preservatives include, without limitation, benzalkonium chloride, chlorobutanol, thimerosal, phenylmercuric acetate, phenylmercuric nitrate and a stabilized oxy chloro composition, for example, PURITE™. Tonicity adjustors suitable for inclusion in a subject pharmaceutical composition include, without limitation, salts such as, e.g., sodium chloride, potassium chloride, mannitol or glycerin and other pharmaceutically acceptable tonicity adjustor. It is understood that these and other substances known in the art of pharmacology can be included in a subject pharmaceutical composition.

Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

A pharmaceutical composition of the present disclosure can comprise a replication-competent, recombinant oncolytic vaccinia virus of the present disclosure in an amount of from about $10^2$ plaque-forming units (pfu) per ml (pfu/ml) to about $10^4$ pfu/ml, from about $10^4$ pfu/ml to about $10^5$ pfu/ml, from about $10^5$ pfu/ml to about $10^6$ pfu/ml, from about $10^6$ pfu/ml to about 10' pfu/ml, from about 10' pfu/ml to about $10^8$ pfu/ml, from about $10^8$ pfu/ml to about $10^9$ pfu/ml, from about $10^9$ pfu/ml to about $10^{10}$ pfu/ml, from about $10^{10}$ pfu/ml to about $10^{11}$ pfu/ml, or from about $10^{11}$ pfu/ml to about $10^{12}$ pfu/ml.

Methods of Inducing Oncolysis

The present disclosure provides methods of inducing oncolysis in an individual having a tumor, the methods comprising administering to the individual an effective amount of a replication-competent, recombinant oncolytic vaccinia virus of the present disclosure or a composition of the present disclosure. Administration of an effective amount of a replication-competent, recombinant oncolytic vaccinia virus of the present disclosure, or a composition of the present disclosure, is also referred to herein as "virotherapy."

In some cases, an "effective amount" of a replication-competent, recombinant oncolytic vaccinia virus of the present disclosure is an amount that, when administered in one or more doses to an individual in need thereof, reduces the number of cancer cells in the individual. For example, in some cases, an "effective amount" of a replication-competent, recombinant oncolytic vaccinia virus of the present disclosure is an amount that, when administered in one or more doses to an individual in need thereof, reduces the number of cancer cells in the individual by at least 10%, at least 15%, at least 20%, at least 25%, at least 30%, at least 40%, at least 50%, at least 60%, at least 70%, at least 80%, at least 90%, or at least 95%, compared to the number of cancer cells in the individual before administration of the replication-competent, recombinant oncolytic vaccinia virus, or in the absence of administration with the replication-competent, recombinant oncolytic vaccinia virus. In some cases, an "effective amount" of a replication-competent, recombinant oncolytic vaccinia virus of the present disclosure is an amount that, when administered in one or more doses to an individual in need thereof, reduces the number of cancer cells in the individual to undetectable levels. In some cases, an "effective amount" of a replication-competent, recombinant oncolytic vaccinia virus of the present disclosure is an amount that, when administered in one or more doses to an individual in need thereof, reduces the tumor mass in the individual. For example, in some cases, an "effective amount" of a replication-competent, recombinant oncolytic vaccinia virus of the present disclosure is an amount that, when administered in one or more doses to an individual in need thereof, reduces the tumor mass in the individual by at least 10%, at least 15%, at least 20%, at least 25%, at least 30%, at least 40%, at least 50%, at least 60%, at least 70%, at least 80%, at least 90%, or at least 95%, compared to the tumor mass in the individual before administration of the replication-competent, recombinant oncolytic vaccinia virus, or in the absence of administration with the replication-competent, recombinant oncolytic vaccinia virus.

In some cases, an "effective amount" of a replication-competent, recombinant oncolytic vaccinia virus of the present disclosure is an amount that, when administered in one or more doses to an individual in need thereof, increases survival time of the individual. For example, in some cases, an "effective amount" of a replication-competent, recombinant oncolytic vaccinia virus of the present disclosure is an amount that, when administered in one or more doses to an individual in need thereof, increases survival time of the individual by at least 1 month, at least 2 months, at least 3 months, from 3 months to 6 months, from 6 months to 1 year, from 1 year to 2 years, from 2 years to 5 years, from 5 years to 10 years, or more than 10 years, compared to the expected survival time of the individual in the absence of administration with the replication-competent, recombinant oncolytic vaccinia virus.

In some cases, an "effective amount" of a replication-competent, recombinant oncolytic vaccinia virus of the present disclosure is an amount that, when administered in one or more doses to an individual in need thereof, provides for an increase in the number of IFN-γ-producing T cells. For example, in some cases, an "effective amount" of a replication-competent, recombinant oncolytic vaccinia virus of the present disclosure is an amount that, when administered in one or more doses to an individual in need thereof, provides for an increase in the number of IFN-γ-producing T cells in the individual of at least 10%, at least 25%, at least 50%, at least 2-fold, at least 5-fold, or at least 10-fold, compared to the number of IFN-γ-producing T cells in the individual before administration of the replication-competent, recombinant oncolytic vaccinia virus, or in the absence of administration with the replication-competent, recombinant oncolytic vaccinia virus.

In some cases, an "effective amount" of a replication-competent, recombinant oncolytic vaccinia virus of the present disclosure is an amount that, when administered in one or more doses to an individual in need thereof, provides for an increase in the circulating level of IL-2 or IL-2v in the individual. For example, in some cases, an "effective amount" of a replication-competent, recombinant oncolytic vaccinia virus of the present disclosure is an amount that, when administered in one or more doses to an individual in need thereof, provides for an increase in the circulating level of IL-2 or IL-2v in the individual at least 10%, at least 25%, at least 50%, at least 2-fold, at least 5-fold, or at least 10-fold, compared to the circulating level of IL-2 or IL-2v in the individual before administration of the replication-competent, recombinant oncolytic vaccinia virus, or in the absence of administration with the replication-competent, recombinant oncolytic vaccinia virus.

In some cases, an "effective amount" of a replication-competent, recombinant oncolytic vaccinia virus of the present disclosure is an amount that, when administered in one or more doses to an individual in need thereof, provides for an increase in the circulating level of IL-2v polypeptide in the individual. For example, in some cases, an "effective amount" of a replication-competent, recombinant oncolytic vaccinia virus of the present disclosure is an amount that, when administered in one or more doses to an individual in need thereof, provides for an increase in the circulating level of IL-2v polypeptide in the individual at least 10%, at least 25%, at least 50%, at least 2-fold, at least 5-fold, or at least 10-fold, compared to the circulating level of IL-2v polypeptide in the individual before administration of the replication-competent, recombinant oncolytic vaccinia virus, or in the absence of administration with the replication-competent, recombinant oncolytic vaccinia virus.

In some cases, an "effective amount" of a replication-competent, recombinant oncolytic vaccinia virus of the present disclosure is an amount that, when administered in one or more doses to an individual in need thereof, provides for an increase in the number of $CD8^+$ tumor-infiltrating lymphocytes (TILs). For example, in some cases, an "effective amount" of a replication-competent, recombinant oncolytic vaccinia virus of the present disclosure is an amount that, when administered in one or more doses to an individual in need thereof, provides for an increase in the number of $CD8^+$ TILs of at least 10%, at least 25%, at least 50%, at least 2-fold, at least 5-fold, or at least 10-fold, compared to the number of $CD8^+$ TILs in the individual before administration of the replication-competent, recombinant oncolytic vaccinia virus, or in the absence of administration with the replication-competent, recombinant oncolytic vaccinia virus.

In some cases, an "effective amount" of a replication-competent, recombinant oncolytic vaccinia virus of the present disclosure is an amount that, when administered in one or more doses to an individual in need thereof, induces a durable anti-tumor immune response, e.g., an anti-tumor immune response that provides for reduction in tumor cell number and/or tumor mass and/or tumor growth for at least 1 month, at least 2 months, at least 6 months, or at least 1 year.

A suitable dosage can be determined by an attending physician or other qualified medical personnel, based on various clinical factors. As is well known in the medical arts, dosages for any one patient depend upon many factors, including the patient's size, body surface area, age, tumor burden, and other relevant factors.

A replication-competent, recombinant oncolytic vaccinia virus of the present disclosure can be administered in an amount of from about $10^2$ plaque-forming units (pfu) to about $10^4$ pfu, from about $10^4$ pfu to about $10^5$ pfu, from about $10^5$ pfu to about $10^6$ pfu, from about $10^6$ pfu to about $10^7$ pfu, from about 10' pfu to about $10^8$ pfu, from about $10^8$ pfu to about $10^9$ pfu, from about $10^9$ pfu to about $10^{10}$ pfu, or from about $10^{10}$ pfu to about $10^{11}$ pfu, per dose.

In some cases, a replication-competent, recombinant oncolytic vaccinia virus of the present disclosure is administered in a total amount of from about $1\times10^9$ pfu to $5\times10^{11}$ pfu. In some cases, a replication-competent, recombinant oncolytic vaccinia virus of the present disclosure is administered in a total amount of from about $1\times10^9$ pfu to about $5\times10^9$ pfu, from about $5\times10^9$ pfu to about $10^{10}$ pfu, from about $10^{10}$ pfu to about $5\times10^{10}$ pfu, from about $5\times10^{10}$ pfu to about $10^{11}$ pfu, or from about $10^{11}$ pfu to about $5\times10^{11}$ pfu. In some cases, a replication-competent, recombinant oncolytic vaccinia virus of the present disclosure is administered in a total amount of about $2\times10^{10}$ pfu.

In some cases, a replication-competent, recombinant oncolytic vaccinia virus of the present disclosure is administered in an amount of from about $1\times10^8$ pfu/kg patient weight to about $5\times10^9$ pfu/kg patient weight. In some cases, a replication-competent, recombinant oncolytic vaccinia virus of the present disclosure is administered in an amount of from about $1\times10^8$ pfu/kg patient weight to about $5\times10^8$ pfu/kg patient weight, from about $5\times10^8$ pfu/kg patient weight to about $10^9$ pfu/kg patient weight, or from about $10^9$ pfu/kg patient weight to about $5\times10^9$ pfu/kg patient weight. In some cases, a replication-competent, recombinant oncolytic vaccinia virus of the present disclosure is administered in an amount of $1\times10^8$ pfu/kg patient weight. In some cases, a replication-competent, recombinant oncolytic vaccinia virus of the present disclosure is administered in an amount of $2\times10^8$ pfu/kg patient weight. In some cases, a replication-competent, recombinant oncolytic vaccinia virus of the present disclosure is administered in an amount of $3\times10^8$ pfu/kg patient weight. In some cases, a replication-competent, recombinant oncolytic vaccinia virus of the present disclosure is administered in an amount of $4\times10^8$ pfu/kg patient weight. In some cases, a replication-competent, recombinant oncolytic vaccinia virus of the present disclosure is administered in an amount of $5\times10^8$ pfu/kg patient weight.

In some cases, multiple doses of a replication-competent, recombinant oncolytic vaccinia virus of the present disclosure are administered. The frequency of administration of a replication-competent, recombinant oncolytic vaccinia virus of the present disclosure can vary depending on any of a variety of factors, e.g., severity of the symptoms, etc. For example, in some embodiments, a replication-competent, recombinant oncolytic vaccinia virus of the present disclosure is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid).

The duration of administration of a replication-competent, recombinant oncolytic vaccinia virus of the present disclosure, e.g., the period of time over which a multimeric polypeptide of the present disclosure, a replication-competent, recombinant oncolytic vaccinia virus of the present disclosure is administered, can vary, depending on any of a variety of factors, e.g., patient response, etc. For example, a replication-competent, recombinant oncolytic vaccinia virus of the present disclosure can be administered over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

A replication-competent, recombinant oncolytic vaccinia virus of the present disclosure is administered to an individual using any available method and route suitable for drug delivery, including in vivo and ex vivo methods, as well as systemic and localized routes of administration.

Conventional and pharmaceutically acceptable routes of administration include intratumoral, peritumoral, intramuscular, intratracheal, intrathecal, intracranial, subcutaneous, intradermal, topical application, intravenous, intraarterial, intraperitoneal, intrabladder, rectal, nasal, oral, and other enteral and parenteral routes of administration. Routes of administration may be combined, if desired, or adjusted depending upon the replication-competent, recombinant oncolytic vaccinia virus and/or the desired effect. A replication-competent, recombinant oncolytic vaccinia virus of the present disclosure can be administered in a single dose or in multiple doses.

In some cases, a replication-competent, recombinant oncolytic vaccinia virus of the present disclosure is administered intravenously. In some cases, a replication-competent, recombinant oncolytic vaccinia virus of the present disclosure is administered intramuscularly. In some cases, a replication-competent, recombinant oncolytic vaccinia virus of the present disclosure is administered locally. In some cases, a replication-competent, recombinant oncolytic vaccinia virus of the present disclosure is administered intratumorally. In some cases, a replication-competent, recombinant oncolytic vaccinia virus of the present disclosure is administered peritumorally. In some cases, a replication-competent, recombinant oncolytic vaccinia virus of the present disclosure is administered intracranially. In some cases, a replication-competent, recombinant oncolytic vaccinia virus of the present disclosure is administered subcutaneously. In some cases, a replication-competent, recombinant oncolytic vaccinia virus of the present disclosure is administered intra-arterially. In some cases, a replication-competent, recombinant oncolytic vaccinia virus of the present disclosure is administered intraperitoneally. In some cases, a replication-competent, recombinant oncolytic vaccinia virus of the present disclosure is administered via an intrabladder route of administration. In some cases, a replication-competent, recombinant oncolytic vaccinia virus of the present disclosure is administered intrathecally.

Combination

In some cases, a replication-competent, recombinant oncolytic vaccinia virus of the present disclosure is administered as an adjuvant therapy to a standard cancer therapy. Standard cancer therapies include surgery (e.g., surgical removal of cancerous tissue), radiation therapy, bone marrow transplantation, chemotherapeutic treatment, antibody treatment, biological response modifier treatment, immunotherapy treatment, and certain combinations of the foregoing. In some cases, a method of the present disclosure comprises: a) administering to an individual in need thereof a replication-competent, recombinant oncolytic vaccinia virus of the present disclosure, or a composition comprising same; and b) administering to the individual a second cancer therapy. In some cases, the second cancer therapy is selected from chemotherapy, biological therapy, radiotherapy, immunotherapy, hormone therapy, anti-vascular therapy, cryotherapy, toxin therapy, oncolytic virus therapy (e.g., an oncolytic virus other than a replication-competent, recombinant oncolytic vaccinia virus of the present disclosure), a cell therapy, and surgery.

Radiation therapy includes, but is not limited to, x-rays or gamma rays that are delivered from either an externally applied source such as a beam, or by implantation of small radioactive sources.

Suitable antibodies for use in cancer treatment include, but are not limited to, e.g., avelumab (Bavencio®; an anti-PD-L1 antibody), trastuzumab (Herceptin), bevacizumab (Avastin™), cetuximab (Erbitux™), panitumumab (Vectibix™), Ipilimumab (Yervoy™), rituximab (Rituxan), alemtuzumab (Lemtrada™), Ofatumumab (Arzerra™), Oregovomab (OvaRex™), Lambrolizumab (MK-3475), pertuzumab (Perjeta™), ranibizumab (Lucentis™) etc., and conjugated antibodies, e.g., gemtuzumab ozogamicin (Mylortarg™), Brentuximab vedotin (Adcetris™), $^{90}$Y-labelled ibritumomab tiuxetan (Zevalin™), $^{131}$I-labelled tositumoma (Bexxar™), etc. Suitable antibodies for use in cancer treatment include, but are not limited to, e.g., Ipilimumab targeting CTLA-4 (as used in the treatment of Melanoma, Prostate Cancer, RCC); Tremelimumab targeting CTLA-4 (as used in the treatment of CRC, Gastric, Melanoma, NSCLC); Nivolumab targeting PD-1 (as used in the treatment of Melanoma, NSCLC, RCC); MK-3475 targeting PD-1 (as used in the treatment of Melanoma); Pidilizumab targeting PD-1 (as used in the treatment of Hematologic Malignancies); BMS-936559 targeting PD-L1 (as used in the treatment of Melanoma, NSCLC, Ovarian, RCC); MEDI4736 targeting PD-L1; MPDL33280A targeting PD-L1 (as used in the treatment of Melanoma); Rituximab targeting CD20 (as used in the treatment of Non-Hodgkin's lymphoma); Ibritumomab tiuxetan and tositumomab (as used in the treatment of Lymphoma); Brentuximab vedotin targeting CD30 (as used in the treatment of Hodgkin's lymphoma); Gemtuzumab ozogamicin targeting CD33 (as used in the treatment of Acute myelogenous leukaemia); Alemtuzumab targeting CD52 (as used in the treatment of Chronic lymphocytic leukaemia); IGN101 and adecatumumab targeting EpCAM (as used in the treatment of Epithelial tumors (breast, colon and lung)); Labetuzumab targeting CEA (as used in the treatment of Breast, colon and lung tumors); huA33 targeting gpA33 (as used in the treatment of Colorectal carcinoma); Pemtumomab and oregovomab targeting Mucins (as used in the treatment of Breast, colon, lung and ovarian tumors); CC49 (minretumomab) targeting TAG-72 (as used in the treatment of Breast, colon and lung tumors); cG250 targeting CAIX (as used in the treatment of Renal cell carcinoma); J591 targeting PSMA (as used in the treatment of Prostate carcinoma); MOv18 and MORAb-003 (farletuzumab) targeting Folate-binding protein (as used in the treatment of Ovarian tumors); 3F8, ch14.18 and KW-2871 targeting Gangliosides (such as GD2, GD3 and GM2) (as used in the treatment of Neuroectodermal tumors and some epithelial tumors); hu3S193 and IgN311 targeting Le y (as used in the treatment of Breast, colon, lung and prostate tumors); Bevacizumab targeting VEGF (as used in the treatment of Tumor vasculature); IM-2C6 and CDP791 targeting VEGFR (as used in the treatment of Epithelium-derived solid tumors); Etaracizumab targeting Integrin_V_3 (as used in the treatment of Tumor vasculature); Volociximab targeting Integrin_5_1 (as used in the treatment of Tumor vasculature); Cetuximab, panitumumab, nimotuzumab and 806 targeting EGFR (as used in the treatment of Glioma, lung, breast, colon, and head and neck tumors); Trastuzumab and pertuzumab targeting ERBB2 (as used in the treatment of Breast, colon, lung, ovarian and prostate tumors); MM-121 targeting ERBB3 (as used in the treatment of Breast, colon, lung, ovarian and prostate, tumors); AMG 102, METMAB and SCH 900105 targeting MET (as used in the treatment of Breast, ovary and lung tumors); AVE1642, IMC-A12, MK-0646, R1507 and CP 751871 targeting IGF1R (as used in the treatment of Glioma, lung, breast, head and neck, prostate and thyroid cancer); KB004 and IIIA4 targeting EPHA3 (as used in the treatment of Lung, kidney and colon tumors, melanoma, glioma and haematological malignancies); Mapatumumab (HGS-ETR1) targeting TRAILR1 (as used in the treatment of Colon, lung and pancreas tumors and hematological malignancies); HGS-ETR2 and CS-1008 targeting TRAILR2; Denosumab targeting RANKL (as used in the treatment of Prostate cancer and bone metastases); Sibrotuzumab and F19 targeting FAP (as used in the treatment of Colon, breast, lung, pancreas, and head and neck tumors); 81C6 targeting Tenascin (as used in the treatment of Glioma, breast and prostate tumors); Blinatumomab (Blincyto; Amgen) targeting CD3 (as used in the treatment of ALL); pembrolizumab targeting PD-1 as used in cancer immunotherapy; 9E10 antibody targeting c-Myc; and the like.

In some cases, a method of the present disclosure comprises administering: a) an effective amount of a replication-competent, recombinant oncolytic vaccinia virus of the present disclosure; and b) an anti-PD-1 antibody. In some cases, a method of the present disclosure comprises administering: a) an effective amount of a replication-competent, recombinant oncolytic vaccinia virus of the present disclosure; and b) an anti-PD-L1 antibody. Suitable anti-PD-1 antibodies include, but are not limited to, pembrolizumab (Keytruda®; MK-3475), Nivolumab (Opdivo®; BMS-926558; MDX1106), Pidilizumab (CT-011), AMP-224, AMP-514 (MEDI-0680), PDR001, and PF-06801591. Suitable anti-PD-L1 antibodies include, but are not limited to, BMS-936559 (MDX1105), durvalumab (MEDI4736; Imfinzi), Atezolizumab (MPDL33280A; Tecentriq), MSB0010718C, and Avelumab (Bavencio; MSB0010718C). See, e.g., Sunshine and Taube (2015) *Curr. Opin. Pharmacol.* 23:32; and Heery et al. (2017) *The Lancet Oncology* 18:587; Iwai et al. (2017) *J. Biomed. Sci.* 24:26; Hu-Lieskovan et al. (2017) *Annals of Oncology* 28: issue Suppl. 5, mdx376.048; and U.S. Patent Publication No. 2016/0159905.

In some cases, a suitable antibody is a bispecific antibody, e.g., a bispecific monoclonal antibody. Catumaxomab, blinatumomab, solitomab, pasotuxizumab, and flotetuzumab are non-limiting examples of bispecific antibodies suitable for use in cancer therapy. See, e.g., Chames and Baty (2009) *MAbs* 1:539; and Sedykh et al. (2018) *Drug Des. Devel. Ther.* 12:195.

Biological response modifiers suitable for use in connection with the methods of the present disclosure include, but are not limited to, (1) inhibitors of tyrosine kinase (RTK) activity; (2) inhibitors of serine/threonine kinase activity; (3) tumor-associated antigen antagonists, such as antibodies that bind specifically to a tumor antigen; (4) apoptosis receptor agonists; (5) interleukin-2; (6) interferon-α; (7) interferon-γ; (8) colony-stimulating factors; (9) inhibitors of angiogenesis; and (10) antagonists of tumor necrosis factor.

Chemotherapeutic agents are non-peptidic (i.e., non-proteinaceous) compounds that reduce proliferation of cancer cells, and encompass cytotoxic agents and cytostatic agents. Non-limiting examples of chemotherapeutic agents include alkylating agents, nitrosoureas, antimetabolites, antitumor antibiotics, plant (vinca) alkaloids, and steroid hormones.

Agents that act to reduce cellular proliferation are known in the art and widely used. Such agents include alkylating agents, such as nitrogen mustards, nitrosoureas, ethylenimine derivatives, alkyl sulfonates, and triazenes, including, but not limited to, mechlorethamine, cyclophosphamide (Cytoxan™), melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide.

Antimetabolite agents include folic acid analogs, pyrimidine analogs, purine analogs, and adenosine deaminase inhibitors, including, but not limited to, cytarabine (CYTOSAR-U), cytosine arabinoside, fluorouracil (5-FU), floxuridine (FudR), 6-thioguanine, 6-mercaptopurine (6-MP), pentostatin, 5-fluorouracil (5-FU), methotrexate, 10-propargyl-5,8-dideazafolate (PDDF, CB3717), 5,8-dideazatetrahydrofolic acid (DDATHF), leucovorin, fludarabine phosphate, pentostatine, and gemcitabine.

Suitable natural products and their derivatives, (e.g., vinca alkaloids, antitumor antibiotics, enzymes, lymphokines, and epipodophyllotoxins), include, but are not limited to, Ara-C, paclitaxel (Taxol®), docetaxel (Taxotere®), deoxycoformycin, mitomycin-C, L-asparaginase, azathioprine; brequinar; alkaloids, e.g. vincristine, vinblastine, vinorelbine, vindesine, etc.; podophyllotoxins, e.g. etoposide, teniposide, etc.; antibiotics, e.g. anthracycline, daunorubicin hydrochloride (daunomycin, rubidomycin, cerubidine), idarubicin, doxorubicin, epirubicin and morpholino derivatives, etc.; phenoxizone biscyclopeptides, e.g. dactinomycin; basic glycopeptides, e.g. bleomycin; anthraquinone glycosides, e.g. plicamycin (mithramycin); anthracenediones, e.g. mitoxantrone; azirinopyrrolo indolediones, e.g. mitomycin; macrocyclic immunosuppressants, e.g. cyclosporine, FK-506 (tacrolimus, prograf), rapamycin, etc.; and the like.

Other anti-proliferative cytotoxic agents are navelbene, CPT-11, anastrazole, letrazole, capecitabine, reloxafine, cyclophosphamide, ifosamide, and droloxafine.

Microtubule affecting agents that have antiproliferative activity are also suitable for use and include, but are not limited to, allocolchicine (NSC 406042), Halichondrin B (NSC 609395), colchicine (NSC 757), colchicine derivatives (e.g., NSC 33410), dolstatin 10 (NSC 376128), maytansine (NSC 153858), rhizoxin (NSC 332598), paclitaxel (Taxol®), Taxol® derivatives, docetaxel (Taxotere®), thiocolchicine (NSC 361792), trityl cysterin, vinblastine sulfate, vincristine sulfate, natural and synthetic epothilones including but not limited to, eopthilone A, epothilone B, discodermolide; estramustine, nocodazole, and the like.

Hormone modulators and steroids (including synthetic analogs) that are suitable for use include, but are not limited to, adrenocorticosteroids, e.g. prednisone, dexamethasone, etc.; estrogens and pregestins, e.g. hydroxyprogesterone caproate, medroxyprogesterone acetate, megestrol acetate, estradiol, clomiphene, tamoxifen; etc.; and adrenocortical suppressants, e g. aminoglutethimide; 17α-ethinylestradiol; diethylstilbestrol, testosterone, fluoxymesterone, dromostanolone propionate, testolactone, methylprednisolone, methyl-testosterone, prednisolone, triamcinolone, chlorotrianisene, hydroxyprogesterone, aminoglutethimide, estramustine, medroxyprogesterone acetate, leuprolide, Flutamide (Drogenil), Toremifene (Fareston), and Zoladex®. Estrogens stimulate proliferation and differentiation, therefore compounds that bind to the estrogen receptor are used to block this activity. Corticosteroids may inhibit T cell proliferation.

Other chemotherapeutic agents include metal complexes, e.g. cisplatin (cis-DDP), carboplatin, etc.; ureas, e.g. hydroxyurea; and hydrazines, e.g. N-methylhydrazine; epidophyllotoxin; a topoisomerase inhibitor; procarbazine; mitoxantrone; leucovorin; tegafur; etc. Other anti-proliferative agents of interest include immunosuppressants, e.g. mycophenolic acid, thalidomide, desoxyspergualin, azasporine, leflunomide, mizoribine, azaspirane (SKF 105685); Iressa® (ZD 1839, 4-(3-chloro-4-fluorophenylamino)-7-methoxy-6-(3-(4-morpholinyl)propoxy)quinazoline); etc.

"Taxanes" include paclitaxel, as well as any active taxane derivative or pro-drug. "Paclitaxel" (which should be understood herein to include analogues, formulations, and derivatives such as, for example, docetaxel, TAXOL™, TAXOTERE™ (a formulation of docetaxel), 10-desacetyl analogs of paclitaxel and 3'N-desbenzoyl-3'N-t-butoxycarbonyl analogs of paclitaxel) may be readily prepared utilizing techniques known to those skilled in the art (see also WO 94/07882, WO 94/07881, WO 94/07880, WO 94/07876, WO 93/23555, WO 93/10076; U.S. Pat. Nos. 5,294,637; 5,283,253; 5,279,949; 5,274,137; 5,202,448; 5,200,534; 5,229,529; and EP 590,267), or obtained from a variety of commercial sources, including for example, Sigma Chemical Co., St. Louis, Mo. (T7402 from *Taxus brevifolia*; or T-1912 from *Taxus yannanensis*).

Paclitaxel should be understood to refer to not only the common chemically available form of paclitaxel, but analogs and derivatives (e.g., Taxotere™ docetaxel, as noted above) and paclitaxel conjugates (e.g., paclitaxel-PEG, paclitaxel-dextran, or paclitaxel-xylose).

Cell therapy includes chimeric antigen receptor (CAR) T cell therapy (CAR-T therapy); natural killer (NK) cell therapy; dendritic cell (DC) therapy (e.g., DC-based vaccine); T cell receptor (TCR) engineered T cell-based therapy; and the like.

Cancers

Cancer cells that may be treated by methods and compositions of the present disclosure include cells from the bladder, blood, bone, bone marrow, brain, breast, colon, esophagus, gastrointestine, gum, head, kidney, liver, lung, nasopharynx, neck, ovary, prostate, skin, stomach, spinal cord, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; Paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; Leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; Kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; Ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; pancreatic cancer; rectal cancer; and hairy cell leukemia.

Tumors that can be treated using a method of the present disclosure include, e.g., a brain cancer tumor, a head and neck cancer tumor, an esophageal cancer tumor, a skin cancer tumor, a lung cancer tumor, a thymic cancer tumor, a stomach cancer tumor, a colon cancer tumor, a liver cancer tumor, an ovarian cancer tumor, a uterine cancer tumor, a bladder cancer tumor, a testicular cancer tumor, a rectal cancer tumor, a breast cancer tumor, or a pancreatic cancer tumor.

In some cases, the tumor is a colorectal adenocarcinoma. In some cases, the tumor is non-small cell lung carcinoma. In some cases, the tumor is a triple-negative breast cancer. In some cases, the tumor is a solid tumor. In some cases, the tumor is a liquid tumor. In some cases, the tumor is recurrent. In some cases, the tumor is a primary tumor. In some cases, the tumor is metastatic.

Subjects Suitable for Treatment

A variety of subjects are suitable for treatment with a subject method of treating cancer. Suitable subjects include any individual, e.g., a human or non-human animal who has cancer, who has been diagnosed with cancer, who is at risk for developing cancer, who has had cancer and is at risk for recurrence of the cancer, who has been treated with an agent other than a an oncolytic vaccinia virus of the present disclosure for the cancer and failed to respond to such treatment, or who has been treated with an agent other than an oncolytic vaccinia virus of the present disclosure for the cancer but relapsed after initial response to such treatment.

Vaccinia Virus Immunogenic Compositions

The present disclosure provides a recombinant vaccinia virus comprising, in its genome, a nucleotide sequence encoding an IL-2v polypeptide, where the IL-2v polypeptide comprises one or more amino acid substitutions that provides for reduced binding to CD25, compared to wild-type IL-2. In some cases, the recombinant vaccinia virus comprises, in its genome, a nucleotide sequence encoding a cancer antigen (also referred to herein as a "cancer-associated antigen"). Thus, the present disclosure provides a recombinant vaccinia virus comprising, in its genome: i) a nucleotide sequence encoding an IL-2v polypeptide, where the IL-2v polypeptide comprises one or more amino acid substitutions that provides for reduced binding to CD25, compared to wild-type IL-2; and ii) a nucleotide sequence encoding a cancer antigen. Such recombinant vaccinia viruses, when administered to an individual in need thereof (e.g., an individual having a cancer), can induce or enhance an immune response in the individual to the encoded cancer antigen. The immune response can reduce the number of cancer cells in the individual. In some cases, the recombinant vaccinia virus is replication competent. In some cases, the recombinant vaccinia virus is replication incompetent. In some cases, the recombinant vaccinia virus is not oncolytic. Suitable IL-2v polypeptides are as described above.

Cancer-associated antigens include, but are not limited to, α-folate receptor; carbonic anhydrase IX (CAIX); CD19; CD20; CD22; CD30; CD33; CD44v7/8; carcinoembryonic antigen (CEA); epithelial glycoprotein-2 (EGP-2); epithelial glycoprotein-40 (EGP-40); folate binding protein (FBP); fetal acetylcholine receptor; ganglioside antigen GD2; Her2/neu; IL-13R-a2; kappa light chain; LeY; L1 cell adhesion molecule; melanoma-associated antigen (MAGE); MAGE-A1; mesothelin; MUC1; NKG2D ligands; oncofetal antigen (h5T4); prostate stem cell antigen (PSCA); prostate-specific membrane antigen (PSMA); tumor-associate glycoprotein-72 (TAG-72); vascular endothelial growth factor receptor-2 (VEGF-R2) (See, e.g., Vigneron et al. (2013) *Cancer Immunity* 13:15; and Vigneron (2015) *BioMed Res. Int'l* Article ID 948501; and epidermal growth factor receptor (EGFR) vIII polypeptide (see, e.g., Wong et al. (1992) *Proc. Natl. Acad. Sci. USA* 89:2965; and Miao et al. (2014) *PLoSOne* 9:e94281); a MUC1 polypeptide; a human papillomavirus (HPV) E6 polypeptide; an LMP2 polypeptide; an HPV E7 polypeptide; an epidermal growth factor receptor (EGFR) vIII polypeptide; a HER-2/neu polypeptide; a melanoma antigen family A, 3 (MAGE A3) polypeptide; a p53 polypeptide; a mutant p53 polypeptide; an NY-ESO-1 polypeptide; a folate hydrolase (prostate-specific membrane antigen; PSMA) polypeptide; a carcinoembryonic antigen (CEA) polypeptide; a melanoma antigen recognized by T-cells (melanA/MART1) polypeptide; a Ras polypeptide; a gp100 polypeptide; a proteinase3 (PR1) polypeptide; a bcr-abl polypeptide; a tyrosinase polypeptide; a survivin polypeptide; a prostate specific antigen (PSA) polypeptide; an hTERT polypeptide; a sarcoma translocation breakpoints polypeptide; a synovial sarcoma X (SSX) breakpoint polypeptide; an EphA2 polypeptide; a prostate acid phosphatase (PAP) polypeptide; a melanoma inhibitor of apoptosis (ML-IAP) polypeptide; an alpha-fetoprotein (AFP) polypeptide; an epithelial cell adhesion molecule (EpCAM) polypeptide; an ERG (TMPRSS2 ETS fusion) polypeptide; a NA17 polypeptide, a paired-box-3 (PAX3) polypeptide; an anaplastic lymphoma kinase (ALK) polypeptide; an androgen receptor polypeptide; a cyclin B1 polypeptide; an N-myc proto-oncogene (MYCN) polypeptide; a Ras homolog gene family member C (RhoC) polypeptide; a tyrosinase-related protein-2 (TRP-2) polypeptide; a mesothelin polypeptide; a prostate stem cell antigen (PSCA) polypeptide; a melanoma associated antigen-1 (MAGE A1) polypeptide; a cytochrome P450 1B1 (CYP1B1) polypeptide; a placenta-specific protein 1 (PLAC1) polypeptide; a BORIS polypeptide (also known as CCCTC-binding factor or CTCF); an ETV6-AML polypeptide; a breast cancer antigen NY-BR-1 polypeptide (also referred to as ankyrin repeat domain-containing protein 30A); a regulator of G-protein signaling (RGS5) polypeptide; a squamous cell carcinoma antigen recognized by T-cells (SART3) polypeptide; a carbonic anhydrase IX polypeptide; a paired box-5 (PAX5) polypeptide; an OY-TES1 (testis antigen; also known as acrosin binding protein) polypeptide; a sperm protein 17 polypeptide; a lymphocyte cell-specific protein-tyrosine kinase (LCK) polypeptide; a high molecular weight melanoma associated antigen (HMW-MAA); an A-kinase anchoring protein-4 (AKAP-4); a synovial sarcoma X breakpoint 2 (SSX2) polypeptide; an X antigen family member 1 (XAGE1) polypeptide; a B7 homolog 3 (B7H3; also known as CD276) polypeptide; a legumain polypeptide (LGMN1; also known as asparaginyl endopeptidase); a tyrosine kinase with Ig and EGF homology domains-2 (Tie-2; also known as angiopoietin-1 receptor) polypeptide; a P antigen family member 4 (PAGE4) polypeptide; a vascular endothelial growth factor receptor 2 (VEGF2) polypeptide; a MAD-CT-1 polypeptide; a fibroblast activation protein (FAP) polypeptide; a platelet derived growth factor receptor beta (PDGFβ) polypeptide; a MAD-CT-2 polypeptide; a Fos-related antigen-1 (FOSL) polypeptide; and a Wilms tumor-1 (WT-1) polypeptide.

Amino acid sequences of cancer-associated antigens are known in the art; see, e.g., MUC1 (GenBank CAA56734); LMP2 (GenBank CAA47024); HPV E6 (GenBank AAD33252); HPV E7 (GenBank AHG99480); EGFRvIII (GenBank NP_001333870); HER-2/neu (GenBank AAI67147); MAGE-A3 (GenBank AAH11744); p53 (GenBank BAC16799); NY-ESO-1 (GenBank CAA05908); PSMA (GenBank AAH25672); CEA (GenBank AAA51967); melan/MART1 (GenBank NP_005502); Ras (GenBank NP_001123914); gp100 (GenBank AAC60634); bcr-abl (GenBank AAB60388); tyrosinase (GenBank AAB60319); survivin (GenBank AAC51660); PSA (GenBank CAD54617); hTERT (GenBank BAC11010); SSX (GenBank NP_001265620); Eph2A (GenBank NP_004422); PAP (GenBank AAH16344); ML-IAP (GenBank AAH14475); AFP (GenBank NP_001125); EpCAM (GenBank NP_002345); ERG (TMPRSS2 ETS fusion) (GenBank ACA81385); PAX3 (GenBank AAI01301); ALK (GenBank NP_004295); androgen receptor (GenBank NP_000035); cyclin B1 (GenBank CA099273); MYCN (GenBank NP_001280157); RhoC (GenBank AAH52808); TRP-2 (GenBank AAC60627); mesothelin (GenBank AAH09272); PSCA (GenBank AAH65183); MAGE A1 (GenBank NP_004979); CYP1B1 (GenBank AAM50512); PLAC1 (GenBank AAG22596); BORIS (GenBank NP_001255969); ETV6 (GenBank NP_001978); NY-BR1 (GenBank NP_443723); SART3 (GenBank NP_055521); carbonic anhydrase IX (GenBank EAW58359); PAX5 (Gen- Bank NP_057953); OY-TES1 (GenBank NP_115878); sperm protein 17 (GenBank AAK20878); LCK (GenBank NP_001036236); HMW-MAA (GenBank NP_001888); AKAP-4 (GenBank NP_003877); SSX2 (GenBank CAA60111); XAGE1 (GenBank NP_001091073; XP_001125834; XP_001125856; and XP_001125872); B7H3 (GenBank NP_001019907; XP_947368; XP_950958; XP_950960; XP_950962; XP_950963; XP_950965; and XP_950967); LGMN1 (GenBank NP_001008530); TIE-2 (GenBank NP_000450); PAGE4 (GenBank NP_001305806); VEGFR2 (GenBank NP_002244); MAD-CT-1 (GenBank NP_005893 NP_056215); FAP (GenBank NP_004451); PDGFβ (GenBank NP_002600); MAD-CT-2 (GenBank NP_001138574); FOSL (GenBank NP_005429); and WT-1 (GenBank NP_000369). These polypeptides are also discussed in, e.g., Cheever et al. (2009) *Clin. Cancer Res.* 15:5323, and references cited therein; Wagner et al. (2003) *J. Cell. Sci.* 116:1653; Matsui et al. (1990) *Oncogene* 5:249; and Zhang et al. (1996) *Nature* 383:168.

As noted above, in some cases, a recombinant vaccinia virus of the present disclosure is replication incompetent. In some cases, the replication-incompetent recombinant vaccinia virus comprises a modification of a vaccinia virus gene that results in inability of the vaccinia virus to replicate. One or more vaccinia virus genes encoding gene products required for replication can be modified such that the vaccinia virus is unable to replicate. For example, a recombinant vaccinia virus can be modified to reduce the levels and/or activity of an intermediate transcription factor (e.g., A8R and/or A23R) (see, e.g., Wyatt et al. (2017) *mBio* 8:e00790; and Warren et al. (2012) *J. Virol.* 86:9514) and/or a late transcription factor (e.g., one or more of G8R, A1L, and A2L) (see, e.g., Yang et al. (2013) *Virology* 447:213). Reducing the levels and/or activity of an intermediate transcription factor and/or a late transcription factor can result in a modified vaccinia virus that can express polypeptide(s) encoded by a nucleotide sequence(s) that is operably linked to an early viral promoter; however, the virus will be unable to replicate. Modifications include, e.g., deletion of all or part of the gene; insertion into the gene; and the like. For example, all or a portion of the A8R gene can be deleted. As another example, all or a portion of the A23R gene can be deleted. As another example, all or a portion of the G8R gene can be deleted. As another example, all or a portion of the AIL gene can be deleted. As another example, all or a portion of the A2L gene can be deleted.

As noted above, in some cases, a recombinant vaccinia virus of the present disclosure is in some cases non-oncolytic.

To induce or enhance an immune response in an individual to a cancer antigen, a recombinant vaccinia virus of the present disclosure (e.g., a recombinant vaccinia virus comprising, in its genome: i) a nucleotide sequence encoding an IL-2v polypeptide, where the IL-2v polypeptide comprises one or more amino acid substitutions that provides for reduced binding to CD25, compared to wild-type IL-2; and ii) a nucleotide sequence encoding the cancer antigen) would be administered to an individual in need thereof. Subjects suitable for treatment include those described above. In some cases, the recombinant vaccinia virus is administered to an individual in need thereof in a low dose, e.g., from about $10^2$ plaque-forming units (pfu) to about $10^4$ pfu, from about $10^4$ pfu to about $10^5$ pfu, or from about $10^5$ pfu to about $10^6$ pfu per dose. In some cases, the recombinant vaccinia virus is administered to an individual in need thereof in a dose of from about $10^6$ pfu to about $10^{12}$ pfu, e.g., in a dose of from about $10^6$ pfu to about $10^7$ pfu, from about $10^7$ pfu to about $10^8$ pfu, from about $10^8$ pfu to about $10^9$ pfu, from about $10^9$ pfu to about $10^{10}$ pfu, from about $10^{10}$ pfu to about $10^{11}$ pfu, or from about $10^{11}$ pfu to about $10^{12}$ pfu.

A recombinant vaccinia virus of the present disclosure can be administered to an individual in need thereof in a pharmaceutical composition, e.g., the pharmaceutical composition can comprise: a) a recombinant vaccinia virus of the present disclosure; and b) a pharmaceutically acceptable excipient. Thus, the present disclosure provides a pharmaceutical composition comprising: a) a recombinant vaccinia virus of the present disclosure; and b) a pharmaceutically acceptable excipient. Suitable pharmaceutically acceptable excipients are as described above. In some cases, the pharmaceutical composition comprises an adjuvant. Suitable adjuvants include, but are not limited to, alum, aluminum phosphate, aluminum hydroxide, MF59 (4.3% w/v squalene, 0.5% w/v Tween 80™, 0.5% w/v Span 85), CpG-containing nucleic acid (where the cytosine is unmethylated), monophosphoryl lipid A (MPL), 3-Q-desacyl-4'-monophosphoryl lipid A (3DMPL), and the like.

A recombinant vaccinia virus of the present disclosure can be administered to an individual in need thereof via any suitable route of administration, e.g., a route of administration as described above. For example, a recombinant vaccinia virus of the present disclosure can be administered to an individual in need thereof via an intramuscular, an intravenous, a subcutaneous route of administration.

Examples of Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure numbered 1-42 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Aspect 1. A replication-competent, recombinant oncolytic vaccinia virus comprising, in its genome, a nucleotide sequence encoding a variant interleukin-2 (IL-2v) polypeptide, wherein the IL-2v polypeptide comprises one or more amino acid substitutions that provides for reduced binding to CD25, compared to wild-type IL-2.

Aspect 2. The vaccinia virus of aspect 1, wherein the vaccinia virus comprises a modification to render the vaccinia thymidine kinase deficient.

Aspect 3. The vaccinia virus of aspect 2, wherein the modification results in a lack of J2R expression and/or function.

Aspect 4. The vaccinia virus of any one of aspects 1-3, wherein the vaccinia virus is a Copenhagen strain vaccinia virus.

Aspect 5. The vaccinia virus of any one of aspects 1-3, wherein the vaccinia virus is a WR strain vaccinia virus.

Aspect 6. The vaccinia virus of any one of aspects 1-5, wherein the vaccinia virus comprises an A34R gene comprising a K151E substitution.

Aspect 7. The vaccinia virus of any one of aspects 1-6, wherein the IL-2v polypeptide comprises substitutions of one or more of F42, Y45, and L72, based on the amino acid numbering of the IL-2 amino acid sequence depicted in SEQ ID NO:1.

Aspect 8. The vaccinia virus of any one of aspects 1-7, wherein the amino acid substitution that provides for reduced binding to CD25 is an F42L, F42A, F42G, F42S, F42T, F42Q, F42E, F42D, F42R, or F42K substitution, based on the amino acid numbering of the IL-2 amino acid sequence depicted in SEQ ID NO:1.

Aspect 9. The vaccinia virus of any one of aspects 1-8, wherein the amino acid substitution that provides for reduced binding to CD25 is a Y45A, Y45G, Y45S, Y45T, Y45Q, Y45E, Y45N, Y45D, Y45R, or Y45K substitution, based on the amino acid numbering of the IL-2 amino acid sequence depicted in SEQ ID NO:1.

Aspect 10. The vaccinia virus of any one of aspects 1-9, wherein the amino acid substitution that provides for reduced binding to CD25 is an L72G, L72A, L72S, L72T, L72Q, L72E, L72N, L72R, or L72K substitution, based on the amino acid numbering of the IL-2 amino acid sequence depicted in SEQ ID NO:1.

Aspect 11. The vaccinia virus of any one of aspects 1-10, wherein the IL-2v polypeptide comprises F42A, Y45A, and L72G substitutions, based on the amino acid numbering of the IL-2 amino acid sequence depicted in SEQ ID NO:1.

Aspect 12. The vaccinia virus of any one of aspects 1-11, wherein the IL-2v polypeptide-encoding nucleotide sequence is operably linked to a regulatable promoter.

Aspect 13. The vaccinia virus of aspect 12, wherein the regulatable promoter is regulated by tetracycline or a tetracycline analog or derivative.

Aspect 14. A composition comprising: a) the vaccinia virus of any one of aspects 1-13; and b) a pharmaceutically acceptable excipient.

Aspect 15. A method of inducing oncolysis in an individual having a tumor, the method comprising administering to the individual an effective amount of the vaccinia virus of any one of aspects 1-13, or the composition of aspect 14.

Aspect 16. The method of aspect 15, wherein said administering comprises administering a single dose of the virus or the composition.

Aspect 17. The method of aspect 16, wherein the single dose comprises at least $10^6$ plaque forming units (pfu) of the vaccinia virus.

Aspect 18. The method of aspect 16, wherein the single dose comprises from $10^9$ to $10^{12}$ pfu of the vaccinia virus.

Aspect 19. The method of aspect 15, wherein said administering comprises administering multiple doses of the vaccinia virus or the composition.

Aspect 20. The method of aspect 19, wherein the vaccinia virus or the composition is administered every other day.

Aspect 21. The method of any one of aspects 15-20, wherein the vaccinia virus or the composition is administered once per week.

Aspect 22. The method of any one of aspects 15-20, wherein the vaccinia virus or the composition is administered every other week.

Aspect 23. The method of any one of aspects 15-21, wherein the tumor is a brain cancer tumor, a head and neck cancer tumor, an esophageal cancer tumor, a skin cancer tumor, a lung cancer tumor, a thymic cancer tumor, a stomach cancer tumor, a colon cancer tumor, a liver cancer tumor, an ovarian cancer tumor, a uterine cancer tumor, a bladder cancer tumor, a testicular cancer tumor, a rectal cancer tumor, a breast cancer tumor, or a pancreatic cancer tumor.

Aspect 24. The method of any one of aspects 15-22, wherein the tumor is a colorectal adenocarcinoma.

Aspect 25. The method of any one of aspects 15-22, wherein the tumor is non-small cell lung carcinoma.

Aspect 26. The method of any one of aspects 15-22, wherein the tumor is a triple-negative breast cancer.

Aspect 27. The method of any one of aspects 15-22, wherein the tumor is a solid tumor.

Aspect 28. The method of any one of aspects 15-22, wherein the tumor is a liquid tumor.

Aspect 29. The method of any one of aspects 15-28, wherein the tumor is recurrent.

Aspect 30. The method of any one of aspects 15-28, wherein the tumor is a primary tumor.

Aspect 31. The method of any one of aspects 15-28, wherein the tumor is metastatic.

Aspect 32. The method of any one of aspects 15-31, further comprising administering to the individual a second cancer therapy.

Aspect 33. The method of aspect 32, wherein the second cancer therapy is selected from chemotherapy, biological therapy, radiotherapy, immunotherapy, hormone therapy, anti-vascular therapy, cryotherapy, toxin therapy, oncolytic virus therapy, a cell therapy, and surgery.

Aspect 34. The method of aspect 32, wherein the second cancer therapy comprises an anti-PD1 antibody or an anti-PD-L1 antibody.

Aspect 35. The method of any one of aspects 15-34, wherein the individual is immunocompromised.

Aspect 36. The method of any one of aspects 15-35, wherein said administering of the vaccinia virus or the composition is intratumoral.

Aspect 37. The method of any one of aspects 15-35, wherein said administering of the vaccinia virus or the composition is peritumoral.

Aspect 38. The method of any one of aspects 15-35, wherein said administering of the vaccinia virus or the composition is intravenous.

Aspect 39. The method of any one of aspects 15-35, wherein said administering of the vaccinia virus or the composition is intra-arterial.

Aspect 40. The method of any one of aspects 15-35, wherein said administering of the vaccinia virus or the composition is intrabladder.

Aspect 41. The method of any one of aspects 15-35, wherein said administering of the vaccinia virus or the composition is intrathecal.

Aspect 42. A recombinant vaccinia virus comprising, in its genome, a nucleotide sequence encoding a variant interleukin-2 (IL-2v) polypeptide, wherein the IL-2v polypeptide comprises one or more amino acid substitutions that provides for reduced binding to CD25, compared to wild-type IL-2.

Aspect 43. A replication-competent, recombinant oncolytic vaccinia virus comprising, in its genome, a nucleotide sequence encoding a variant interleukin-2 (IL-2v) polypeptide comprising SEQ ID NO: 9, wherein the vaccinia virus is a Copenhagen strain vaccinia virus, is vaccinia thymidine kinase deficient, and comprises an A34R gene comprising a K151E substitution.

Aspect 44. The vaccinia virus of aspect 43, further comprising a signal peptide.

Aspect 45. The vaccinia virus of aspect 44, wherein the signal peptide comprises SEQ ID NO:22.

Aspect 46. A replication-competent, recombinant oncolytic vaccinia virus comprising, in its genome, a variant interleukin-2 (IL-2v) nucleotide sequence comprising SEQ ID NO:10, wherein the vaccinia virus is a Copenhagen strain vaccinia virus, is vaccinia thymidine kinase deficient, and comprises an A34R gene comprising a K151E substitution.

Aspect 47. A replication-competent, recombinant oncolytic vaccinia virus comprising, in its genome, a variant interleukin-2 (IL-2v) nucleotide sequence comprising SEQ ID NO:12, wherein the vaccinia virus is a Copenhagen strain vaccinia virus, is vaccinia thymidine kinase deficient, and comprises an A34R gene comprising a K151E substitution.

Aspect 48. A composition comprising: (i) the vaccinia virus of any one of aspects 42-47 and (ii) a pharmaceutically acceptable carrier.

Aspect 49. A replication-competent, recombinant oncolytic vaccinia virus comprising, in its genome, a nucleotide sequence encoding a variant interleukin-2 (IL-2v) polypeptide, wherein the IL-2v polypeptide provides reduced biological activity when compared to wild-type IL-2.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); i.v., intravenous(ly); i.t., intratumoral(ly); and the like.

Example 1

Generation of Recombinant Vaccinia Virus Constructs

Features of certain vaccinia virus constructs generated in connection with the examples provided below are summarized in Table 3, below. Each virus in Table 3 has a deletion of the J2R gene except VV18 which has an insertional inactivation of the J2R gene. VV27, VV38, VV39 and VV79 have the gene encoding mouse IL-2v (with F76A, Y79A, L106G substitutions) which was codon optimized for expression in mouse cells, and VV75, VV99 and VV100 has the gene encoding human IL-2v (with F62A, Y65A, and L92G substitutions) which was codon optimized for expression in human cells.

TABLE 3

| Vaccinia Virus Construct (VV #) | Description |
|---|---|
| VV27 | Cop.mIL-2v.A34R-K151E |
| VV38 | Cop.mIL-2v |
| VV39 | WR.mIL-2v |
| VV79 | WR.mIL-2v.A34R-K151E |
| VV16 | Cop.Luc-GFP.A34R-K151E |
| VV18 | Cop.mGM-CSF.A34R-K151E |
| VV03 | WR.Luc-GFP |
| VV17 | WR.Luc-GFP.A34R-K151E |
| VV75 | Cop hIL-2v.A34R-K151E |
| VV99 | WR.hIL-2 |
| VV100 | WR.hIL-2v |

VV27 Construction

The virus is based on the Copenhagen strain of vaccinia and carries the gene encoding the mouse IL-2 variant under the control of a synthetic early late promoter and operator. The virus was engineered for enhanced extracellular enveloped virus (EEV) production by incorporation of a K151E substitution in the A34R gene. VV27 was constructed using a helper virus-mediated, restriction enzyme-guided, homologous recombination repair and rescue technique. First, the gene encoding mouse IL-2v (F76A, Y79A, L106G) was codon optimized for expression in mouse cells and synthesized by GeneWiz (South Plainfield, N.J.). The DNA was digested with BglII/AsiSI and inserted into the Copenhagen J2R homologous recombination plasmid also digested with BglII/AsiSI. The mouse IL-2v gene and flanking left and right vaccinia homology regions were amplified by PCR to generate the homologous recombination donor fragment. BSC-40 cells were infected with Shope Fibroma Virus (SFV), a helper virus, for one hour and subsequently transfected with a mixture of the donor amplicon and purified vaccinia genomic DNA previously restriction digested within the J2R region. The parent genomic DNA originated from a Copenhagen strain vaccinia virus carrying firefly luciferase and GFP in place of the native J2R gene and a K151E mutation (substitution) within the A34R gene for enhanced EEV production. Transfected cells were incubated until significant cytopathic effects were observed and total cell lysate was harvested by 3 rounds of freezing/thawing and sonication. Lysates were serially diluted, plated on BSC-40 monolayers, and covered by agar overlay. GFP negative plaques were isolated under a fluorescent microscope over a total of three rounds of plaque purification. One plaque (KR144) was selected for intermediate amplification in BSC-40 cells in a T225 flask, prior to large scale amplification in HeLa cells in a 20-layer cell factory. The virus was purified by sucrose gradient ultracentrifugation and thoroughly characterized in quality control assays, including full genome next generation sequencing.

VV38 Construction

The virus is based on the Copenhagen strain of vaccinia and carries the gene encoding the mouse IL-2 variant under the control of a synthetic early late promoter and operator. The virus is identical to VV27 except that it carries a wildtype A34R gene and is not engineered for enhanced EEV production. VV38 was constructed using a helper virus-mediated, restriction enzyme-guided, homologous recombination repair and rescue technique. BSC-40 cells were infected with SFV helper virus for 1-2 hours and subsequently transfected with a mixture of the donor amplicon and purified vaccinia genomic DNA previously digested with AsiSI in the J2R region. The parent genomic DNA originated from a Copenhagen strain vaccinia virus carrying firefly luciferase and GFP in place of the native J2R gene. Transfected cells were incubated until significant cytopathic effects were observed and total cell lysate was harvested by 3 rounds of freezing/thawing and sonication. Lysates were serially diluted, plated on BSC-40 monolayers, and covered by agar overlay. GFP negative plaques were isolated under a fluorescent microscope for a total of three rounds of plaque purification. One plaque (LW226) was selected for intermediate amplification in BSC-40 cells in a T225 flask, prior to large scale amplification in HeLa cells in a 20-layer cell factory. The virus was purified by sucrose gradient ultracentrifugation and thoroughly characterized in quality control assays, including full genome next generation sequencing.

VV39 Construction

The virus is based on the Western Reserve (WR) strain of vaccinia and carries the gene encoding the mouse IL-2 variant under the control of a synthetic early late promoter and operator. VV39 was constructed using a helper virus-mediated, restriction enzyme-guided, homologous recombination repair and rescue technique. BSC-40 cells were infected with SFV helper virus for 1-2 hours and subsequently transfected with a mixture of the donor amplicon and purified vaccinia genomic DNA previously digested with AsiSI in the J2R region. The parent genomic DNA originated from a WR strain vaccinia virus carrying a luciferase-2A-GFP reporter gene cassette in place of the native J2R gene and a wild-type A34R, which is not engineered for enhanced EEV production. Transfected cells were incubated until significant cytopathic effects were observed and total cell lysate was harvested by 3 rounds of freezing/thawing and sonication. Lysates were serially diluted, plated on BSC-40 monolayers, and covered by agar overlay. GFP negative plaques were isolated under a fluorescent microscope for a total of three rounds of plaque purification. One plaque (LW228) was selected for intermediate amplification in BSC-40 cells in a T225 flask, prior to large scale amplification in HeLa cells in a 20-layer cell factory. The virus (lot #180330) was purified by sucrose gradient ultracentrifugation and thoroughly characterized in quality control assays, including full genome next generation sequencing.

Example 2 mIL-2v-Armed Vaccinia Virus Activity in MC38 Tumor-Bearing C57BL/6 Mice

Female C57BL/6 mice (8-10 weeks old) were implanted subcutaneously (SC) on the right upper rear flank with 5e5 MC38 tumor cells. MC38 is a murine colon adenocarcinoma cell line. See, e.g., Cancer Research (1975) vol. 35, pp. 2434-2439. Nine days after tumor cell implantation, mice were randomized based on tumor volume into separate treatment groups (average tumor volume per group ~50 mm$^3$; N=14-25/group). On days 10 and 17 post-implantation, tumors were directly injected with 60 μL vehicle (30 mM Tris, 10% sucrose, pH 8.0) or 60 μL vehicle containing 1e7 plaque forming units (pfu) of transgene-armed Copenhagen (Cop) vaccinia virus. Tumor-bearing mice were observed daily, and both tumor volumes and body weights measured bi-weekly until mice were humanely sacrificed either due to i) tumor volume surpassing 1400 mm$^3$, ii) ≥20% body weight loss, or iii) severely diminished health status. Groups of mice were treated as follows:

Group i) vehicle only;

Group ii) VV16: Cop vaccinia virus carrying the A34R-K151E mutation (amino acid substitution) and armed with a Luciferase and green fluorescent protein (Luc-2A-GFP) dual reporter cassette;

Group iii) VV18: Cop vaccinia virus carrying the A34R-K151E substitution and armed with a murine granulocyte-macrophage colony-stimulating factor (mGM-CSF) transgene; or Group iv) VV27: Cop vaccinia virus carrying the A34R-K151E substitution and armed with a murine interleukin 2 variant (mIL-2v) transgene (VV27).

Comparisons between the tumor growth profiles of groups (i)-(iv) (FIG. 3) revealed that only the mIL-2v-armed Cop vaccinia virus (Cop.mIL-2v.A34R-K151E) produced a statistically significant inhibitory effect on tumor growth over multiple consecutive days (FIG. 4, Table 1, ANCOVA results).

FIGS. 3A-3E. Assessment of virotherapy-induced tumor growth inhibition on C57BL/6 female mice implanted SC with MC38 tumor cells. Tumor growth trajectories are shown for individual mice in groups treated with vehicle only (A) or Copenhagen vaccinia virus armed with either a Luciferase-2A-GFP reporter (Cop.Luc-GFP.A34R-K151E) (B), mGM-CSF (Cop.mGM-CSF.A34R-K151E) (C), or mIL-2v (Cop.mIL-2v.A34R-K151E) (D) transgene. Dashed vertical lines on each graph represent time points when mice received intratumoral injections of vehicle or virus. The dashed horizontal line on each graph represents the tumor volume threshold used as a criterion to remove animals from the study. Average tumor mean volumes (mm$^3$)±SEM for each treatment group are shown through day 21 post-tumor implant (E), which was the last tumor measurement time point when animals in each group were still alive.

FIG. 4, Table 1. Statistical comparison of virotherapy-induced tumor growth inhibition using ANCOVA. Tumor volumes for individual mice in each group prior to vehicle/virus treatment (day 7 post-tumor implantation) or on multiple days after treatment were analyzed by ANCOVA to determine statistically significant inhibitory effects on tumor growth across various treatment groups. Columns show the statistical results (p values) of comparisons between specific treatment group pairs. Values in bold font represent comparative ANCOVA results where p≤0.05.

Figure 5:
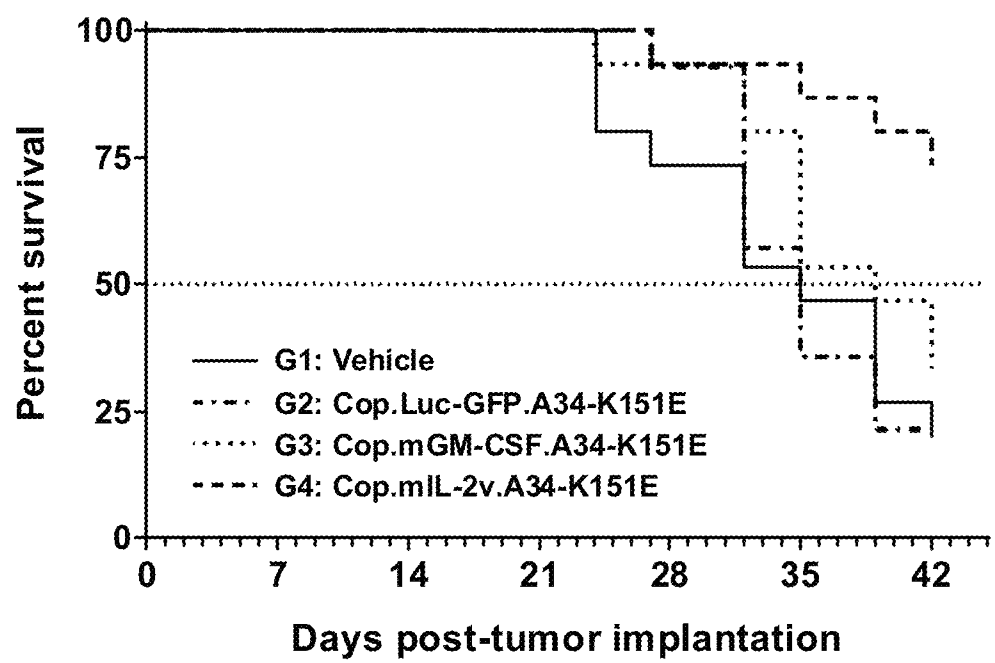
FIG. 5 depicts survival of MC38 tumor-implanted C57BL/6 female mice following treatment with vehicle or virus on days 10 and 17 after implantation.

Survival of animals in each treatment group (N=15/group) was also assessed up through day 42 post-tumor implantation (FIG. 5). In this case, mice treated with the mIL-2v-armed Cop vaccinia virus showed a statistically significant mean survival advantage over all other treatment groups (Log rank/Mantel-Cox test, p=0.0084). Within the cohorts of animals surviving out to day 42, 40% (6 of 15) had no or very small tumors (volume <50 mm$^3$) in the mIL-2v-armed Cop vaccinia virus treated group in comparison to only 7% (1 of 15) for the mGM-CSF-armed Cop vaccinia virus treated group or 13% (2 of 15) in either the vehicle or reporter transgene-armed vaccinia virus treated groups.

FIG. 5. Survival of MC38 tumor-implanted C57BL/6 female mice following treatment with vehicle or virus on days 10 and 17 after implantation. Mice were designated on a daily basis as deceased upon reaching one or more criteria for humane sacrifice (tumor volume ≥1400 mm$^3$, body weight loss ≥20%, and/or severely diminished health status). The point of intersection between each group's curve and the vertical dashed line indicates the median (50%) survival threshold for group.

Figure 6A:
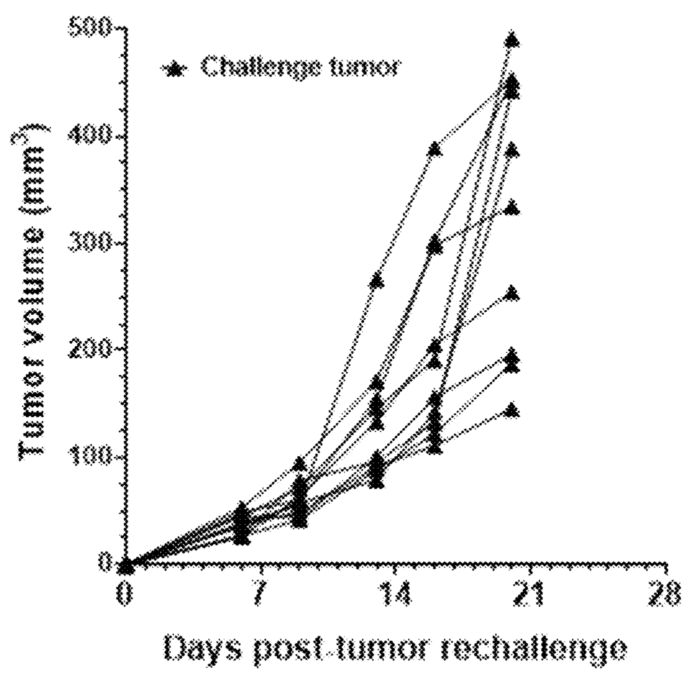
FIGS. 6A and 6B depicts SC MC38 tumor cell challenge of untreated (control, no prior tumor or treatment) C57BL/6 female mice (FIG. 6A) or those previously implanted with MC38 tumor cells and treated with mIL-2v-armed Copenhagen (Cop.mIL-2v.A34-K151E) virus (FIG. 6B).
Figure 6B:
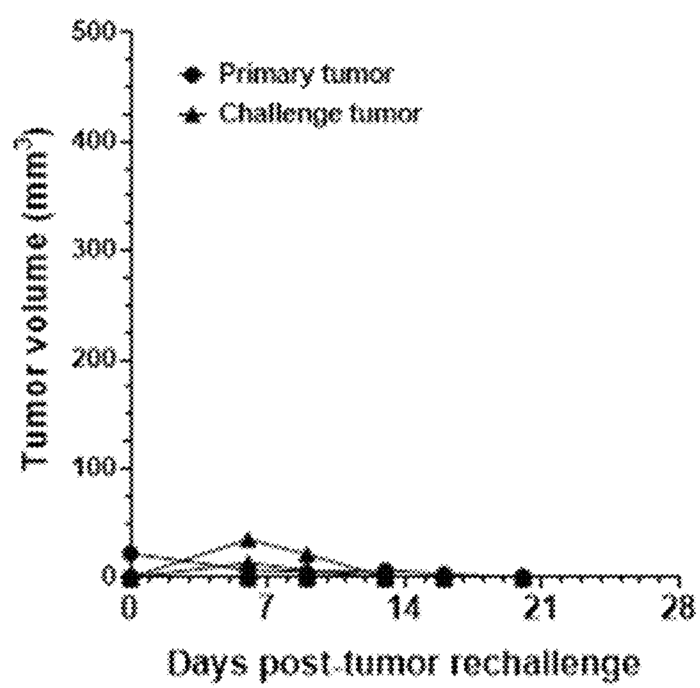

Mice from the mIL-2v-armed Cop vaccinia virus treated group with no or low tumor burden were further evaluated to determine whether MC38 tumor cells implanted at a second anatomical site could effectively form tumors in the absence of additional virus treatment. On day 47 after the first tumor cell implantation, 6 mice from the mIL-2v-armed Cop vaccinia virus treated group along with 10 additional mice, which had neither been previously implanted with MC38 tumor cells nor treated with vehicle or virus, were inoculated SC with 5e5 MC38 tumor cells on the left rear flank. Tumor volumes were then measured biweekly to monitor tumor growth progression over time (FIGS. 6A and 6B). Under these conditions, all mice previously treated with mIL-2v-armed Cop vaccinia virus not only completely rejected the second tumors within two weeks, but also cleared any residual traces of the original primary tumors. This was in contrast to the control group, where all mice developed rapidly growing MC38 tumors over the same period. This result suggested that mIL-2v-armed Cop vaccinia virus treatment facilitated induction of anti-tumor responses that could continue to control new tumor outgrowth after virotherapy was discontinued.

FIGS. 6A and 6B. Subcutaneous MC38 tumor cell challenge of untreated (control, no prior tumor or treatment) C57BL/6 female mice (A) or those previously implanted with MC38 tumor cells and treated with mIL-2v-armed Cop (Cop.mIL-2v.A34-K151E) virus (B). Tumor growth profiles are displayed for individual mice in each group as well as primary and secondary tumors on the same animals (Cop.mIL-2v.A34R-K151E treated group only). After tumor cell implantation, no treatment was administered to either group.

Figure 7:
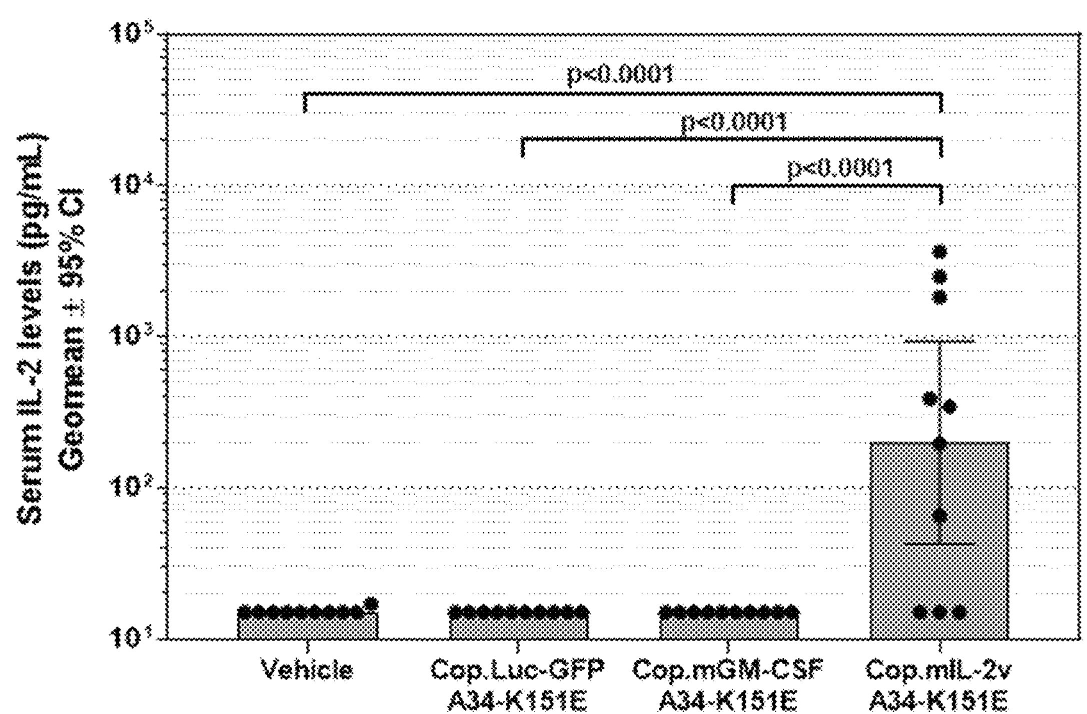
FIG. 7 depicts IL-2 levels detected in sera collected from MC38 tumor-bearing C57BL/6 female mice 48 hr after the first intratumoral (i.t. or IT) injection with vehicle or transgene-armed Cop vaccinia viruses.

In addition to monitoring tumor growth inhibition and survival, sera and spleens were collected from tumor-bearing mice at various time points after injection with vehicle or transgene-armed Cop vaccinia virus to assess circulating IL-2 levels and host cellular responses, respectively. Circulating IL-2 levels in sera collected from each treatment group 48 hr after receiving intratumoral injections were quantified by ELISA (FIG. 7). Measurable levels of IL-2 were detected in the serum from the majority of animals treated with the mIL-2v-armed Cop vaccinia virus, while no IL-2 was seen in any animal from the vehicle or other transgene-armed Cop vaccinia virus. This latter result indicated that intratumoral injection of Cop vaccinia viruses lacking the mIL-2v transgene, at least at the tested dose levels, was insufficient to induce increased circulating IL-2 levels in the sera of treated animals Thus, elevated levels seen in the sera of mice treated with the mIL-2v-armed Cop vaccinia virus should be indicative of transgene-mediated expression following intratumoral injection.

FIG. 7. IL-2 levels detected in sera collected from MC38 tumor-bearing C57BL/6 female mice 48 hr after the first intratumoral injection with vehicle or transgene-armed Cop vaccinia viruses. Each symbol represents the calculated IL-2 serum levels for an individual mouse, while bars represent group geometric mean (N=10/group). Error bars represent 95% confidence intervals. Statistical comparisons between groups were performed using a one-way ANOVA on log-transformed data followed by a Sidak's post-hoc test between selected groups (post-hoc test results shown as p values).

Cellular responses to vaccinia virus and MC38 tumor antigens induced as a result of treating tumors with transgene-armed Cop viruses were assessed by ELISpot or intracellular cytokine staining assays using splenocytes recovered from individual mice. In both assays, splenocytes were restimulated overnight with culture media containing vaccinia protein-specific peptides, a Murine Leukemia Virus (MuLV) protein-specific peptide (p15E) expressed by MC38 cells, or irradiated MC38 cells to promote detection of antigen-specific IFN-γ producing cells. Quantitation of IFN-γ+ splenocytes recovered from mice 3-days after the second intratumoral injection of vehicle or virus (day 20 post-tumor implantation) revealed both considerable and comparable responses to vaccinia peptides in both groups treated with transgene-armed virus, while no responses were apparent in the vehicle treated group (FIG. 8A); this result is consistent with exposure to vaccinia virus. Antigen-specific responses to irradiated MC38 tumor cells and the MuLV p15E peptide, by comparison, were statistically elevated only in the mIL-2v-armed Cop vaccinia virus treated group compared to the vehicle treated group (FIG. 8B; p=0.044 for irradiated MC38 cells and p=0.011 for MuLV p15E, one-way ANOVA). In mice that had controlled or eliminated primary MC38 tumors as a result of IL-2v-armed Cop vaccinia virus treatment and were subsequently rechallenged with a second MC38 tumor cell implantation, vaccinia virus and MC38 tumor cell antigen-specific IFN-γ+ CD8+ T cells frequencies were statistically higher than for untreated control mice 4-weeks following tumor rechallenge (FIG. 8C; $p<0.0001$ for B8 peptide restimulation; $p<0.05$ for MuLV p15E peptide restimulation; $p<0.01$ for irradiated MC38 cell restimulation; paired t test analysis). Taken together, these cellular analyses indicate that virotherapy of tumors with an IL-2v-armed Cop vaccinia virus can induce efficacious and durable anti-tumor cellular responses.

Figure 8A:
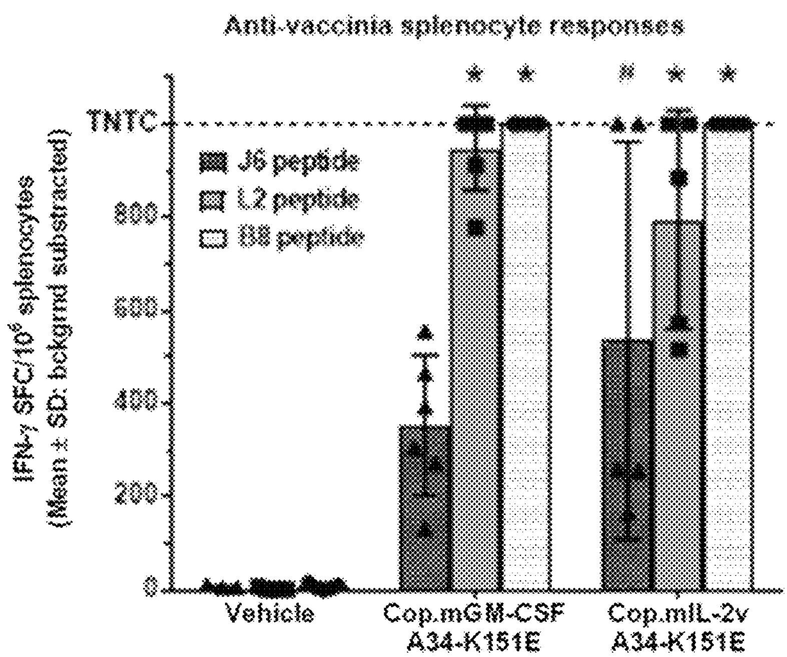
FIGS. 8A-8C depict host cellular responses to vaccinia viral antigens and MC38 tumor antigens following initial oncolytic virus treatment (FIG. 8A and FIG. 8B) and tumor rechallenge (FIG. 8C).
Figure 8B:
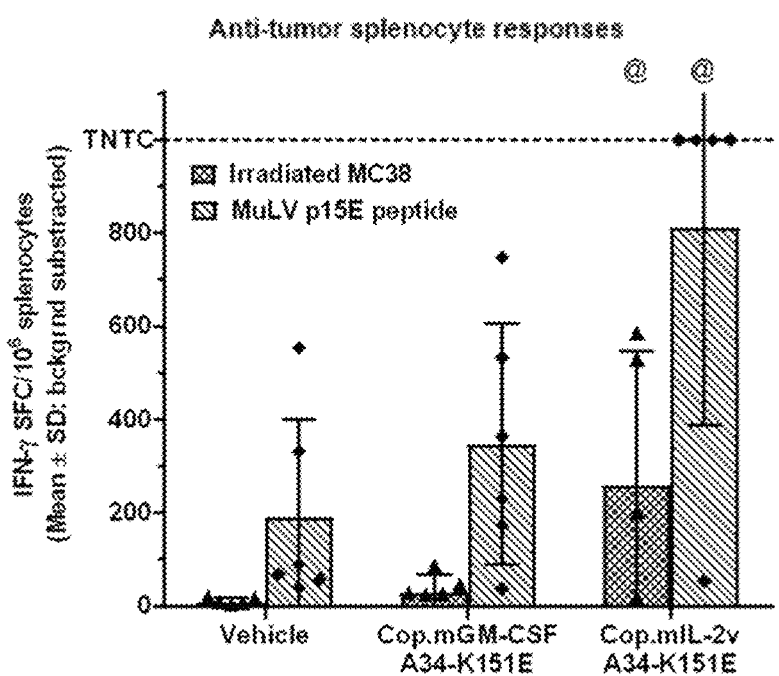
Figure 8C:
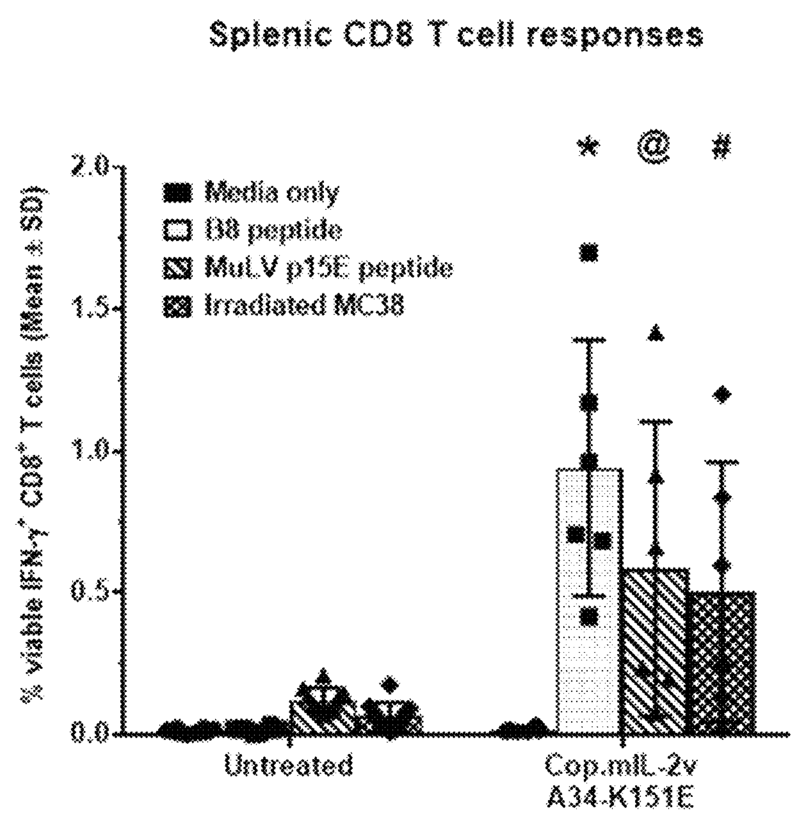

FIGS. 8A-8C. Host cellular responses to vaccinia viral antigens and MC38 tumor antigens following initial virotherapy (A, B) and tumor rechallenge (C). A and B) Splenocytes recovered at day 20 from C57BL/6 female mice implanted with MC38 tumor cells on day 0 and injected intratumorally with vehicle or transgene-armed Cop vaccinia virus on days 10 and 17 were restimulated overnight in culture media +/− peptides derived from vaccinia proteins (J6, L2 or B8), a MuLV peptide expressed by MC38 cells (p15E), or γ-irradiated MC38 cells on IFN-γ ELISpot plates. After 18 hr, plates were developed to detect spot forming cells (SFC), dried, and counted using an ELISpot plate reader. Mean IFN-γ+ SFC responses per 1e6 input cells are shown for each treatment group with responses for individual animals indicated by symbols. C) Splenocytes recovered on day 27 post-tumor rechallenge from IL-2v-armed Cop vaccinia virus treated, MC38 tumor-bearing C57BL/6 female mice, or day 27 post-implantation of untreated (control) mice were similarly restimulated overnight with viral and MC38 tumor antigens in 96-well culture plates containing media with Brefeldin A. After 15-19 hr, cells were harvested, stained for surface markers and viability, then fixed and permeabilized to stain for intracellular IFN-γ. The frequency of live CD8+ T cells producing IFN-γ in each sample were detected and enumerated by flow cytometry and are represented as mean % IFN-γ+ CD8+ T cells per total live splenocytes. For graphs a and b, statistical comparisons between treatment groups and each restimulation condition were performed using a one-way ANOVA with Tukey's post-hoc test ($^{@}p<0.05$ between vehicle and virus-treated groups; $^{\#}p<0.01$ between vehicle and virus treated groups; $^{*}p<0.0001$ between vehicle and virus-treated groups). TNTC=too numerous to count, upper limit of detection in assay. For graph c, statistical comparisons between groups with the same restimulation antigen were performed using an unpaired t test ($^{@}p<0.05$ between naïve and virus-treated groups; $^{\#}p<0.01$ between naive and virus treated groups; $^{*}p<0.0001$ between naive and virus-treated groups).

Example 3 mIL-2v-Armed Vaccinia Virus Activity in MC38 Tumor-Bearing C57BL/6 Mice

Groups of MC38 tumor-bearing C57BL/6 female mice, established as described in Example 1, were injected intratumorally on day 10 post-tumor implantation with 60 μL vehicle or 60 μL containing different dose levels (1e5 pfu vs. 1e7 pfu) of transgene-armed Cop vaccinia virus. At designated time points thereafter, tumors and spleens were collected from cohorts of mice in each treatment group to assess virus and transgene-mediated changes in immune cell populations. Tumors recovered on days 13, 15, 17 and 21 post-tumor implantation from these mice were first processed to release tumor infiltrating lymphocytes (TIL). TIL were then stained to enumerate specific immune cell types by flow cytometry. Kinetic analysis of TIL (FIGS. 9A-9F) revealed that both tested dose levels of the mIL-2v-armed Cop vaccinia virus, but not the other transgene-armed Cop vaccinia viruses, produced a transient but statistically significant increase in NK cells at 120 hr post-treatment (2-way ANOVA, $p<0.0001$ for mIL-2v-armed Cop vaccinia virus treatment vs. vehicle and other test vaccinia virus treatments). At the 1e5 pfu dose level (FIGS. 9A-9C), the mIL-2v-armed Cop vaccinia virus treatment was also able to produce a faster increase in CD8+ TIL seen at 120 hr post-treatment 2-way ANOVA, $p<0.001$ for mIL-2v-armed Cop vaccinia virus vs. vehicle and other test vaccinia virus treatments), although by the 168 hr post-treatment time point all vaccinia virus-treated groups showed a similar statistically significant increase in CD8+ TIL (2-way ANOVA, $p<0.0007$ for all test Cop vaccinia virus vs. vehicle treatment). In contrast, IL-2v-armed Cop vaccinia virus treatment did not lead to increases in regulatory CD4+ TIL (FIGS. 9A-9F), and use of any tested Cop vaccinia virus resulted in lower regulatory CD4+ TIL as compared to vehicle treatment at 168 hr post-treatment (2-way ANOVA, $p\leq0.05$). These results are consistent with the predicted action of the mIL-2v protein, which is expected to act as a stimulator for NK and CD8+ T cell activity but not regulatory CD4+ T cell activity.

FIGS. 9A-9F. Kinetic immunophenotype profiling of TIL populations following intratumoral treatment with 1e5 pfu (A-C) or 1e7 pfu (D-F) transgene-armed Cop vaccinia virus. TIL were isolated from MC38 tumor-bearing C57BL/6 female mice at different time points after intratumoral injection (day 10 post-tumor implantation) with vehicle or transgene-armed Cop vaccinia virus and then stained using a cocktail of fluorophore-labeled antibodies to quantify the frequency of NK cell, CD8+ T cell, and CD4+ T regulatory (Treg) cell populations among total live CD45+ TIL by flow cytometry. Each graph shows the measured frequency of the indicated cell population at several time points following injection of vehicle or Cop vaccinia virus armed with either a Luciferase-GFP reporter (Cop.Luc-GFP.A34R-K151E) or a mIL-2v (Cop.mIL-2v.A34R-K151E) transgene. Error bars represent the standard error of the mean.

Example 4 mIL-2v-Armed Vaccinia Virus Activity in MC38 Tumor-Bearing C57BL/6 Mice

Figure 10A:
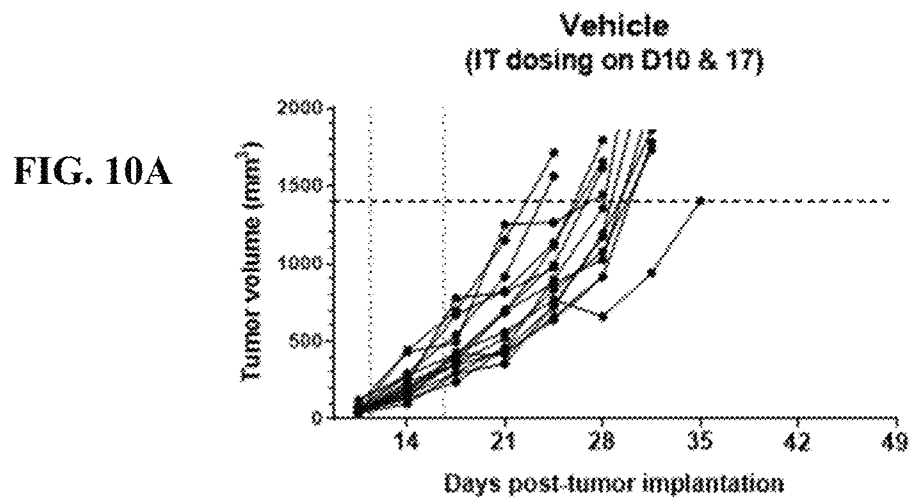
Figure 10B:
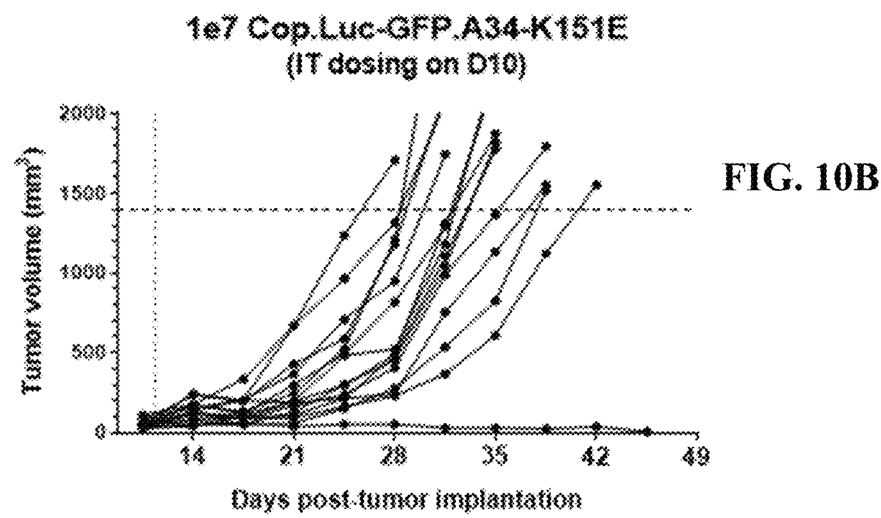
Figure 10C:
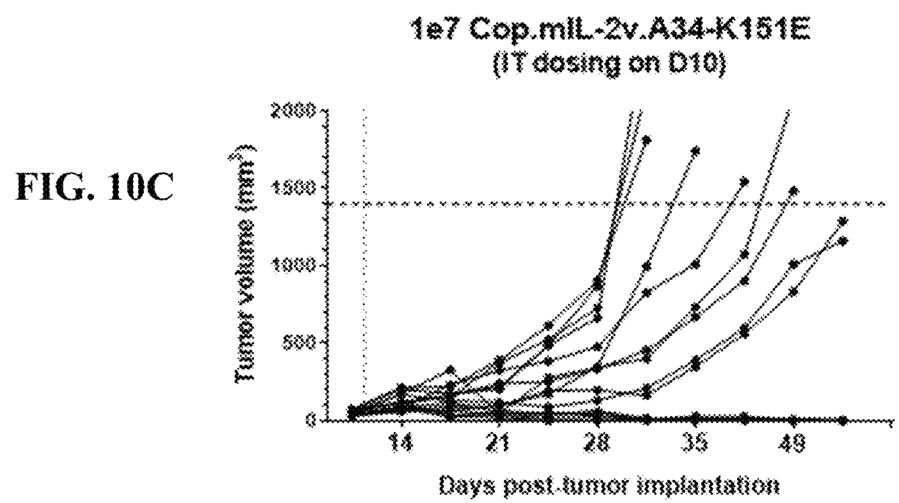
Figure 10D:
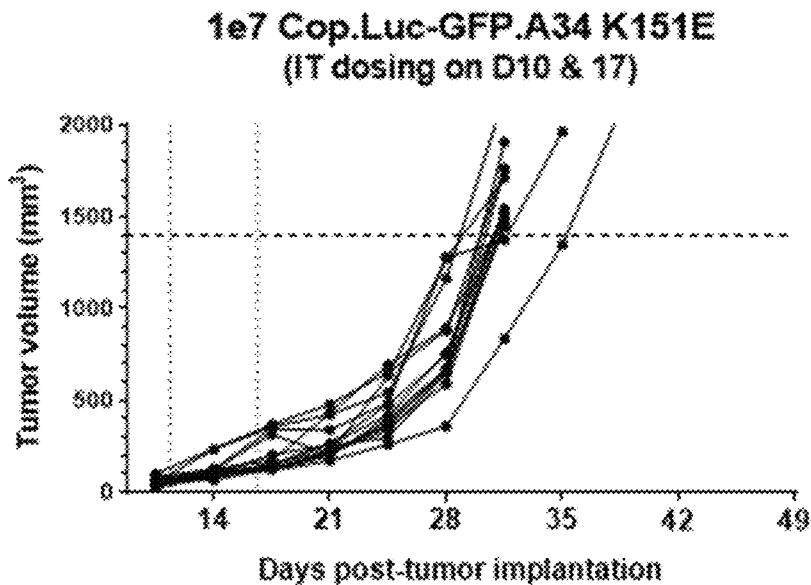
Figure 10E:
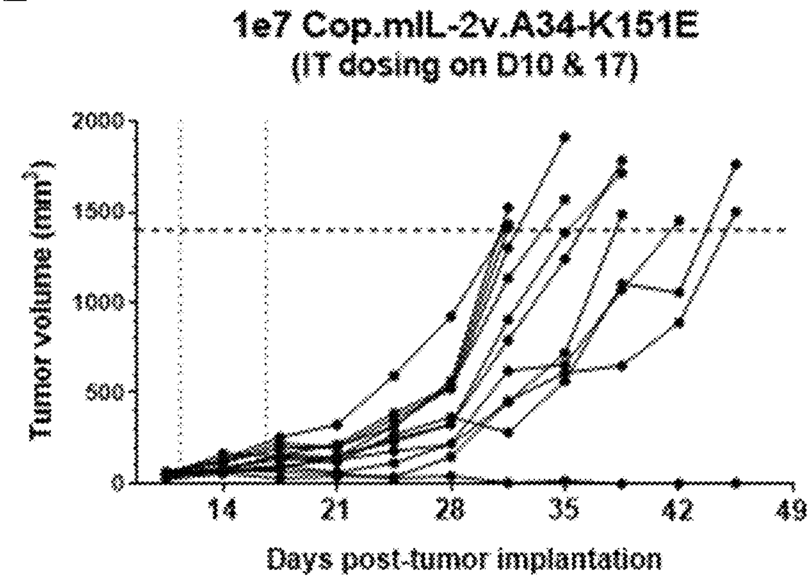
Figure 10F:
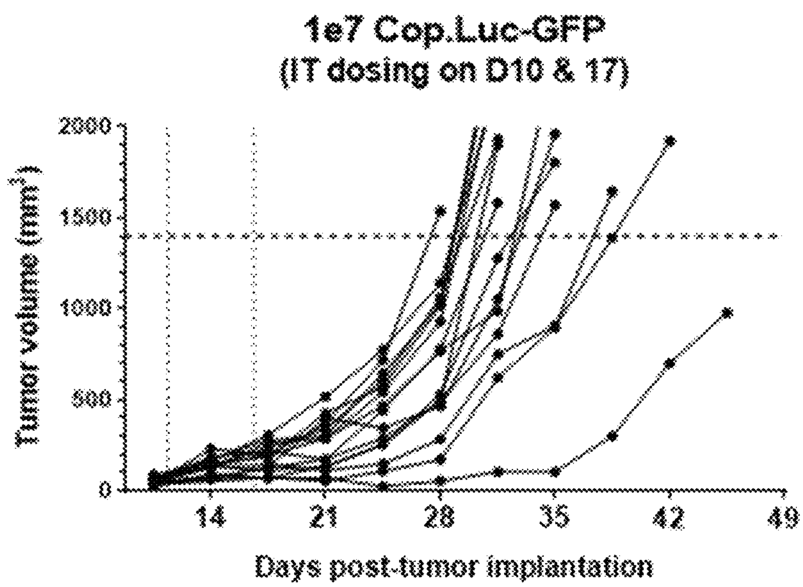
Figure 10G:
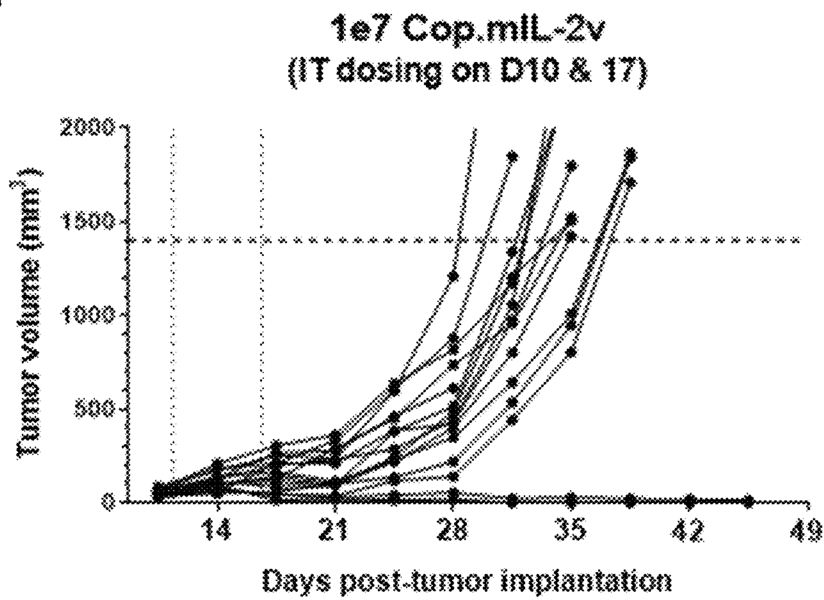
Figure 12A:
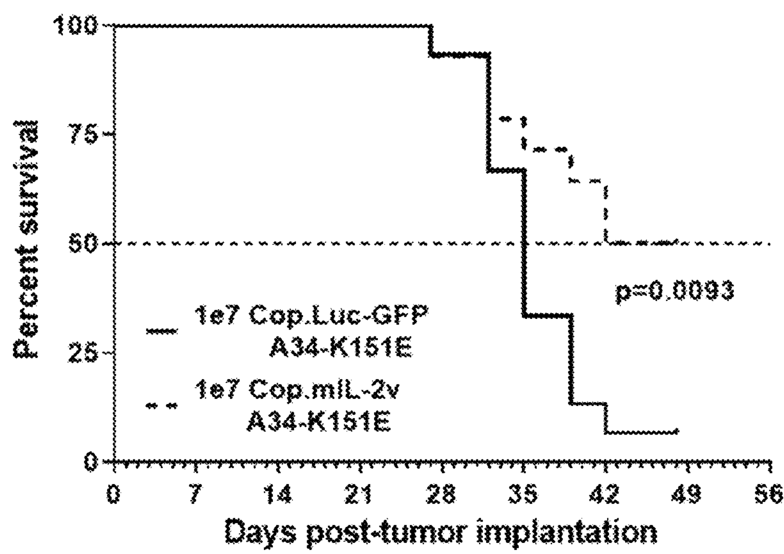
FIGS. 12A-12C depict survival of MC38 tumor-implanted C57BL/6 female mice following treatment with vehicle or virus on day 10 only (FIG. 12A) or days 10 and 17 (FIG. 12B and FIG. 12C) after implantation.
Figure 12B:
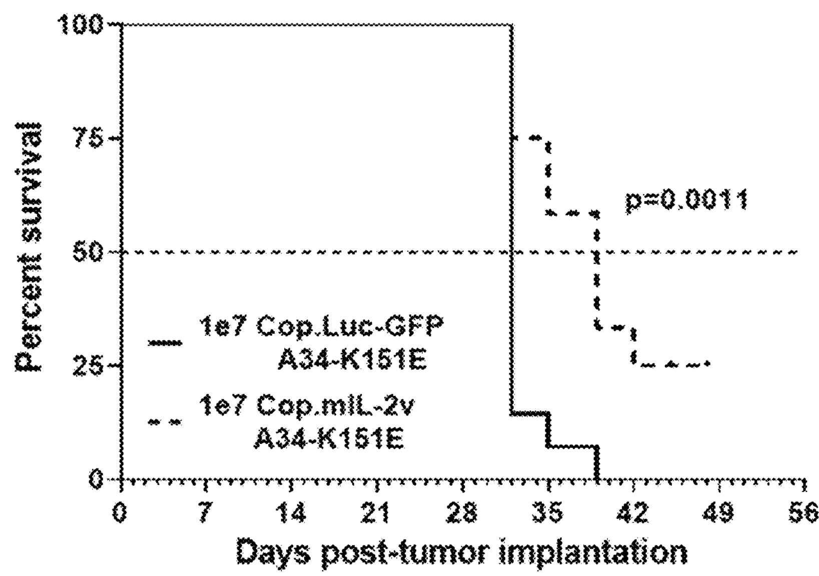
Figure 12C:
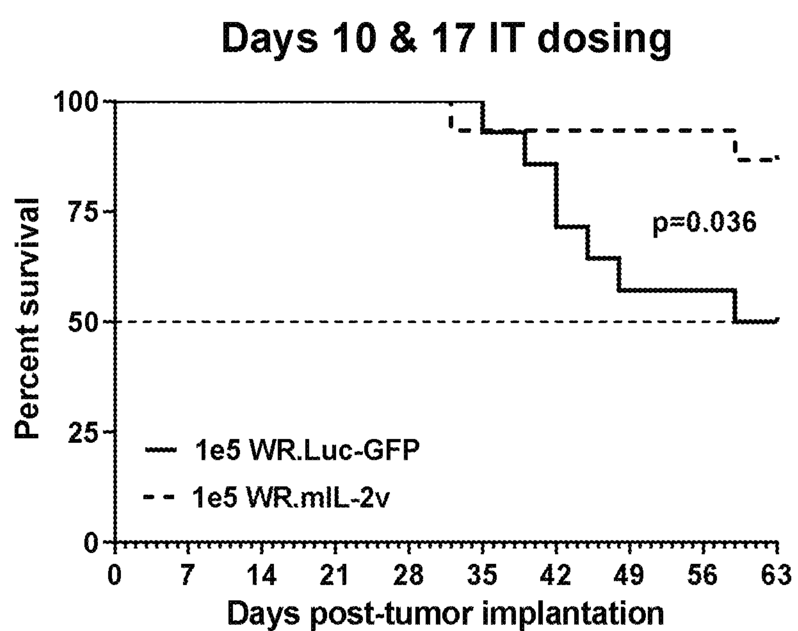

Groups of MC38 tumor-bearing C57BL/6 female mice, established as described in Example 1, were injected intratumorally on day 10 or days 10 and 17 post-tumor implantation with 60 μL vehicle or 60 μL vehicle containing 1e7 pfu of transgene-armed (reporter or mIL-2v) Cop vaccinia virus±the A34R K151E substitution, or 1e5 pfu of transgene-armed (reporter or mIL-2v) Western Reserve (WR) vaccinia virus. Tumor-bearing mice were observed daily, and both tumor volumes and body weights measured biweekly until mice were humanely sacrificed either due to i) tumor volume surpassing 1400 $mm^3$, ii) ≥20% body weight loss, or iii) severely diminished health status. Comparisons between tumor growth profiles of groups treated with vehicle only (FIG. 10A) or vaccinia viruses armed with either a Luciferase-GFP reporter (FIGS. 10F and 10H) or mIL-2v transgene (FIGS. 10G and 10I) showed strong early tumor growth inhibition effects that were initially associated with virus treatment regardless of transgene arming (FIG. 11, Table 2, ANCOVA results). However, the mIL-2v-armed Cop vaccinia virus carrying the A34R-K151E substitution (Cop.mIL-2v.A34R-K151E; VV27; FIGS. 10C and 10E) did produce an even greater inhibitory effect on tumor growth compared to its reporter transgene-armed comparator virus (Cop.Luc-GFP.A34R-K151E; FIGS. 10B and 10D) on multiple consecutive days starting at day 21 after tumor implant (FIG. 11, Table 2, ANCOVA results). Moreover, even though mIL-2v-driven effects on tumor growth inhibition were less pronounced in this example, statistically significant survival advantages attributable to mIL-2v-arming of either Cop (VV38) or WR (VV39) vaccinia viruses were evident between all reporter-armed and mIL-2v-armed vaccinia virus pair comparisons (FIGS. 12A-12C). Overall, these results demonstrate that improved anti-tumor efficacy associated with arming an oncolytic vaccinia virus with an IL-2v transgene is not limited to the Copenhagen strain, but appears extendable to other vaccinia virus strains such as Western Reserve.

FIGS. 10A-10I. Assessment of virotherapy-induced tumor growth inhibition on C57BL/6 female mice implanted SC with MC38 tumor cells. Tumor growth trajectories are shown for individual mice in groups treated intratumorally on day 10 only or days 10 and 17 post-tumor implantation. Treatment groups included injection with 60 μL vehicle only, 60 μL containing 1e7 pfu Cop vaccinia virus with or without the A34R-K151E substitution and armed with either a Luciferase-GFP reporter (Cop.Luc-GFP (F) or Cop.Luc-GFP.A34R-K151E (B and D)) or a mIL-2v (Cop mIL-2v (VV38) (G) or Cop.mIL-2v.A34R-K151E (VV27) (C and E)) transgene, or 60 μL containing 1e5 pfu WR vaccinia virus armed with either a Luciferase-GFP reporter (WR.Luc-GFP (H)) or a mIL-2v (WR.mIL-2v; VV39 (I)) transgene. Dashed vertical lines on each graph represent time points when mice received intratumoral injections of vehicle or virus. The dashed horizontal line on each graph represents the tumor volume threshold used as a criterion to remove animals from the study.

FIG. 11, Table 2. Statistical comparison of virotherapy-induced tumor growth inhibition using ANCOVA. Tumor volumes for individual mice in each group prior to vehicle/virus treatment (day 9 post-tumor implantation) or on multiple days after treatment were analyzed by ANCOVA to determine statistically significant inhibitory effects on tumor growth across various treatment groups. Columns show the statistical results (p values) of comparisons between specific treatment group pairs. Values in bold font represent comparative ANCOVA results where $p\leq0.05$. ND=not determined.

FIGS. 12A-12C. Survival of MC38 tumor-implanted C57BL/6 female mice following treatment with vehicle or virus on day 10 only (a) or days 10 and 17 (b, c) after implantation. Mice were designated as deceased on a daily basis upon reaching one or more criteria for humane sacrifice (tumor volume ≥1400 $mm^3$, body weight loss ≥20%, and/or severely diminished health status). The point of intersection between each group's curve and the vertical dashed line indicates the median (50%) survival threshold for group. P values on each graph represent the statistical results of Log-rank test (Mantel-Cox) comparisons between select virus groups.

Figure 13A:
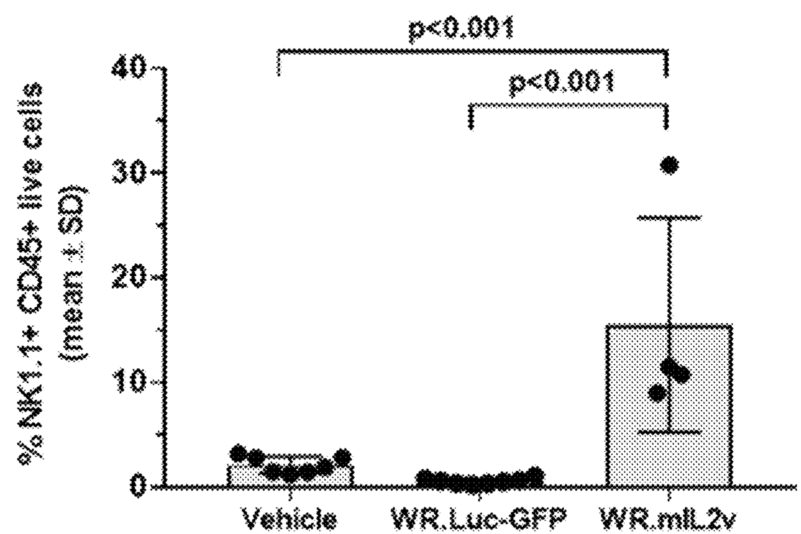
FIGS. 13A and 13B depict immunophenotype profiling of TIL after intratumoral virotherapy using transgene-armed Western Reserve (WR) vaccinia viruses.
Figure 13B:
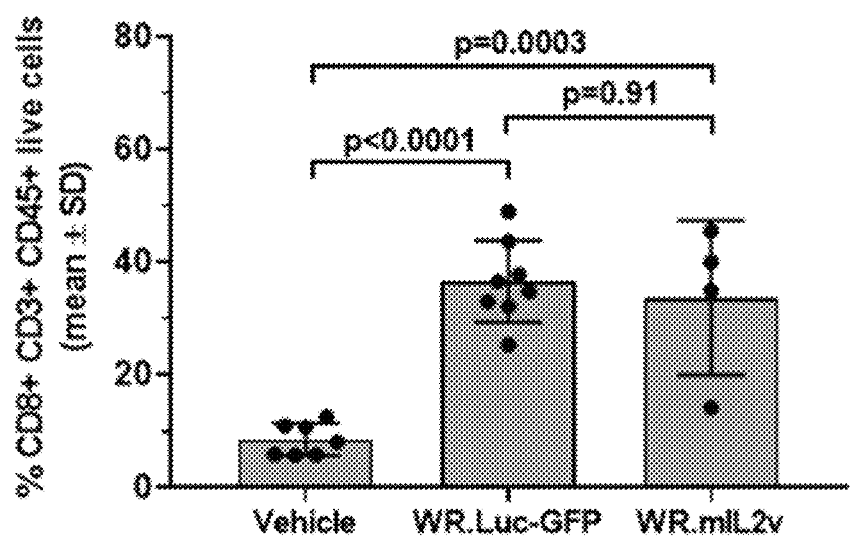
Figure 14C:
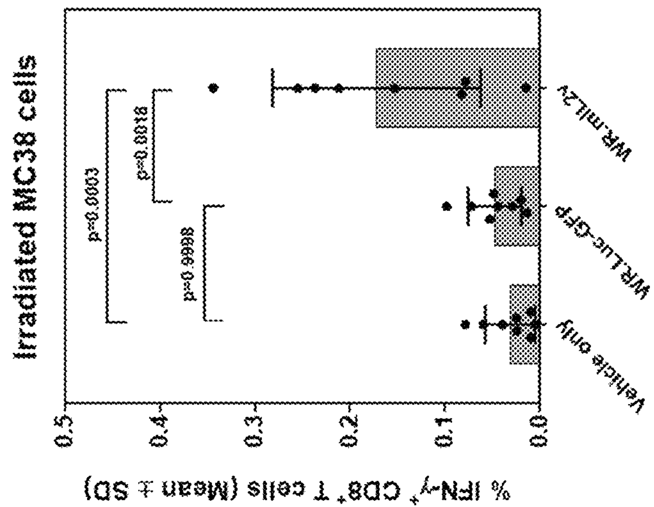
FIGS. 14A-14C depicts host cellular responses to vaccinia viral antigens and MC38 tumor antigens following initial virotherapy.
Figure 14B:
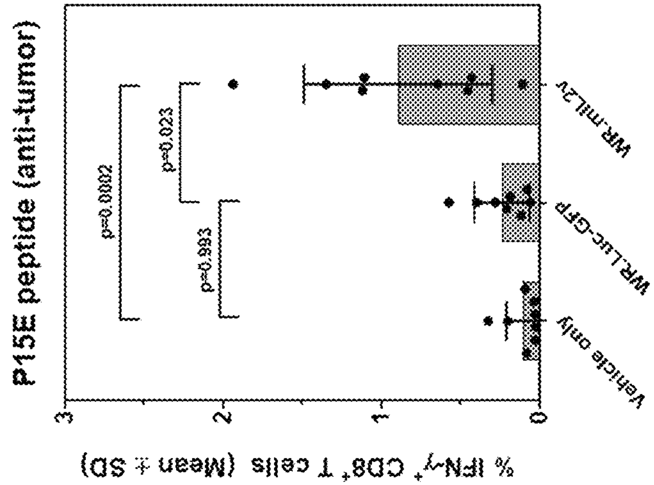
Figure 14A:
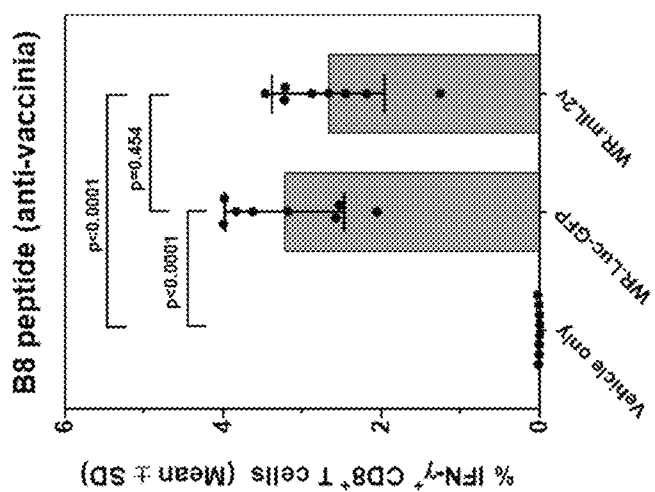

Cohorts of tumor-bearing mice from each treatment group of this study were additionally sacrificed to collect tumors and spleens to assess virus- and transgene-mediated changes in TIL populations and cellular immune responses, respectively. TIL isolated from tumors on day 17 post-tumor implant (day 7 post-treatment) were stained to enumerate specific immune cell types by flow cytometry. Consistent with data shown for the mIL-2v-armed Cop vaccinia virus (FIGS. 9A-9F), intratumoral treatment with a mIL-2v-armed WR vaccinia virus (WR.mIL-2v; VV39), and not a reporter transgene-armed comparator virus (WR.Luc-GFP), led to a statistically significant increase in NK cells among isolated TIL (FIG. 13A). In contrast, CD8+ TIL levels at this same time point appeared mostly sensitive to vaccinia virus treatment and not the presence or absence of the mIL-2v transgene (FIG. 13B). Given that a kinetic analysis of TIL populations only showed an early effect of mIL-2v-arming of Cop vaccinia virus on CD8+ TIL (FIGS. 9A-9F), mIL-2v-driven effects on CD8+ TIL could be particularly sensitive to the timing of analysis and dose of virus used to initiate treatment. Analyses of anti-vaccinia and anti-tumor immune responses induced by virotherapy with reporter and mIL-2v transgene-armed WR vaccinia viruses also produced results that were consistent with similar transgene-armed Cop vaccinia viruses (FIGS. 14A-14C). Specifically, intratumoral treatment with either WR.Luc-GFP or WR.mIL-2v elicited similar anti-vaccinia B5 peptide-specific CD8+ T cell responses that were statistically different from vehicle control treated animals 7-days following virotherapy. However, only treatment with WR.mIL-2v, and not WR.Luc-GFP, produced statistically significant CD8+ T cell responses to MC38 tumors using p15E peptide and irradiated MC38 tumor cell-specific readouts. As noted above, these results further demonstrate that anti-tumor effects resulting from viral delivery of an IL-2v transgene can be achieved using more than one strain of vaccinia.

Figure 15B:
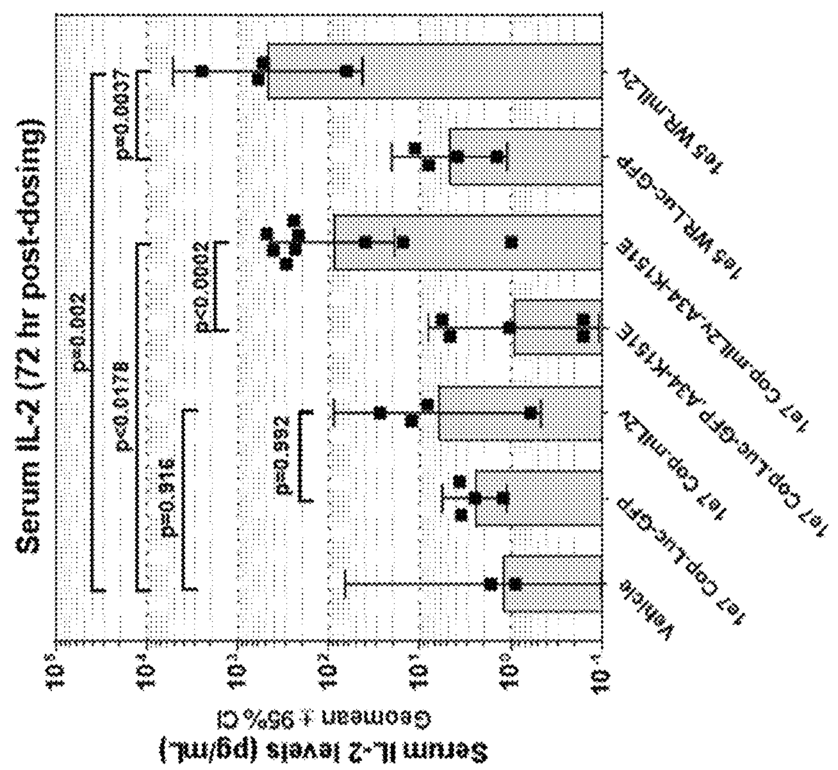
FIGS. 15A and 15B depicts IL-2 levels detected in sera collected from MC38 tumor-bearing C57BL/6 female mice 24 hr and 72 hr after IT injection with vehicle, transgene-armed Cop vaccinia viruses, or transgene-armed WR vaccinia viruses.
Figure 15A:
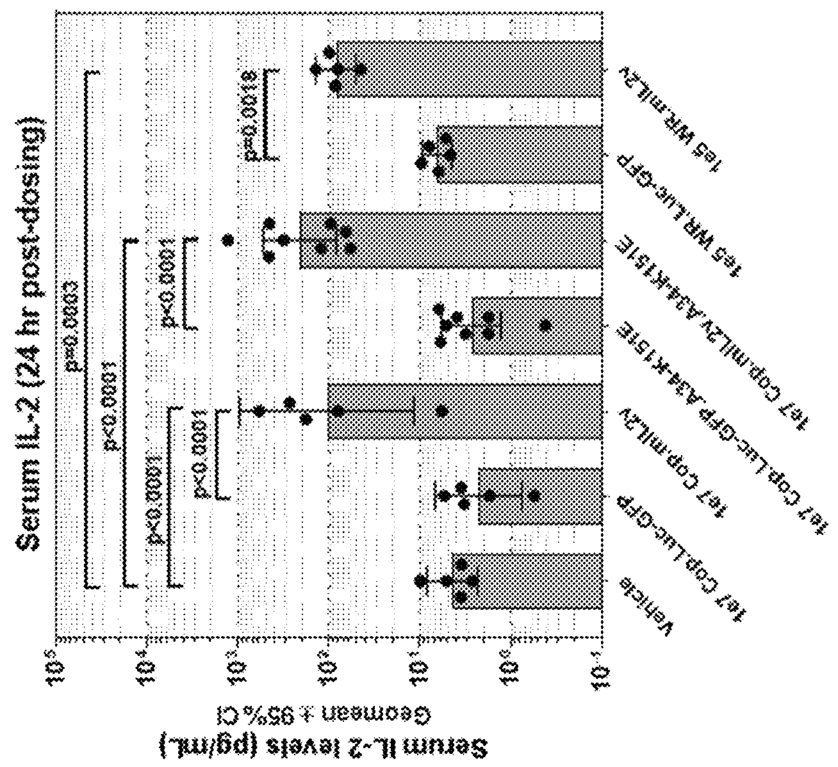
Figure 16A:
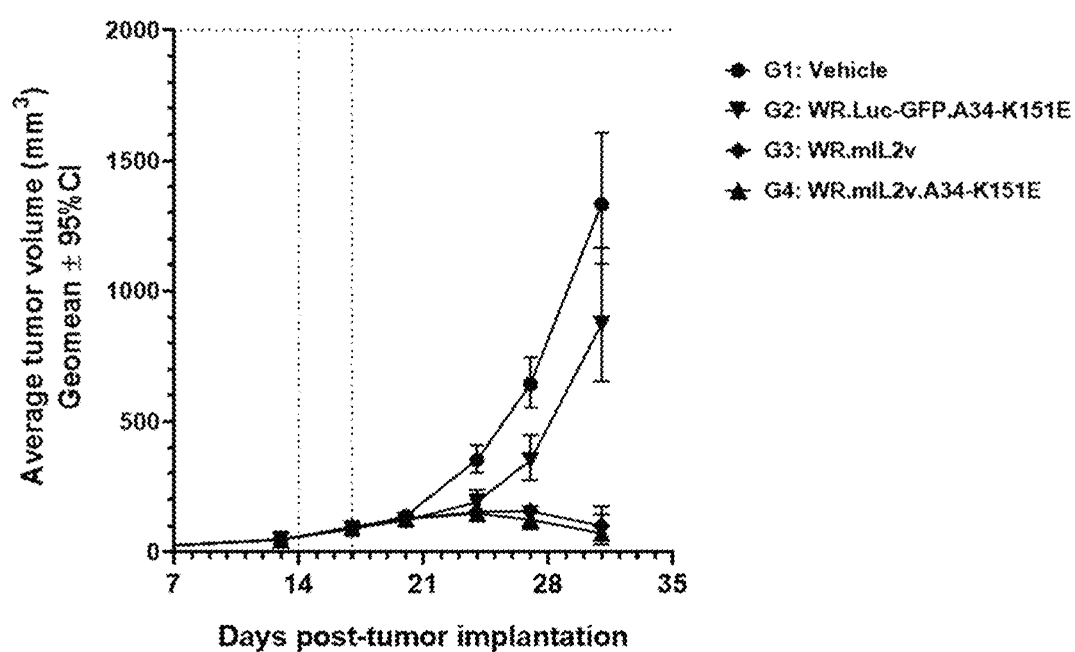
FIGS. 16A-16E depict an assessment of the effect of a recombinant oncolytic vaccinia virus of the present disclosure on tumor growth in vivo following intravenous (IV) delivery into C57BL/6 female mice implanted subcutaneously (SC) with LLC tumor cells.
Figure 16B:
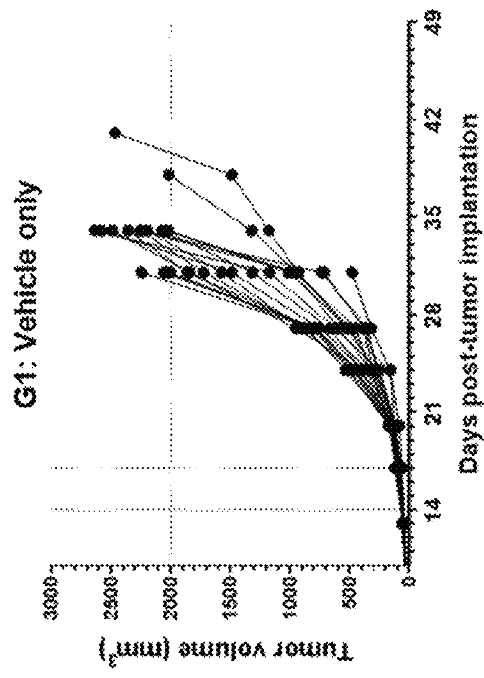
Figure 16C:
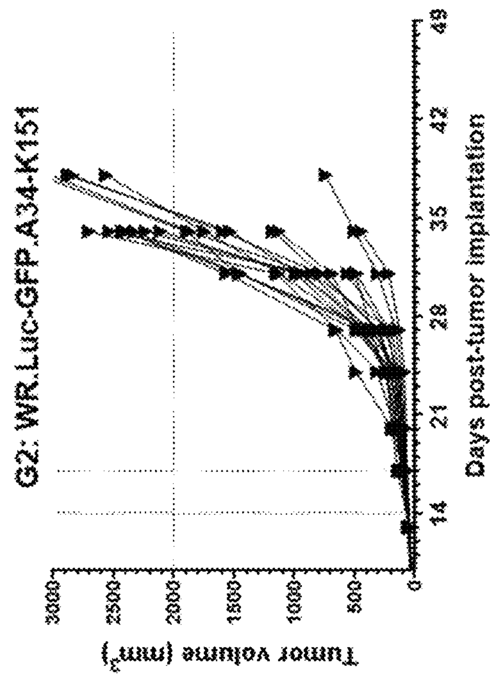
Figure 16D:
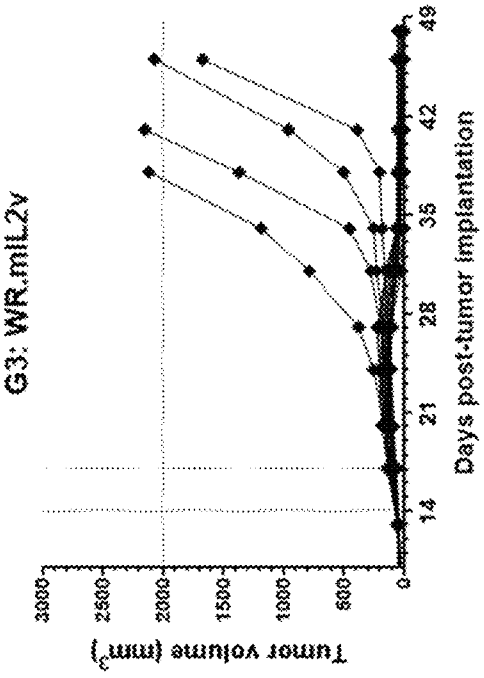
Figure 16E:
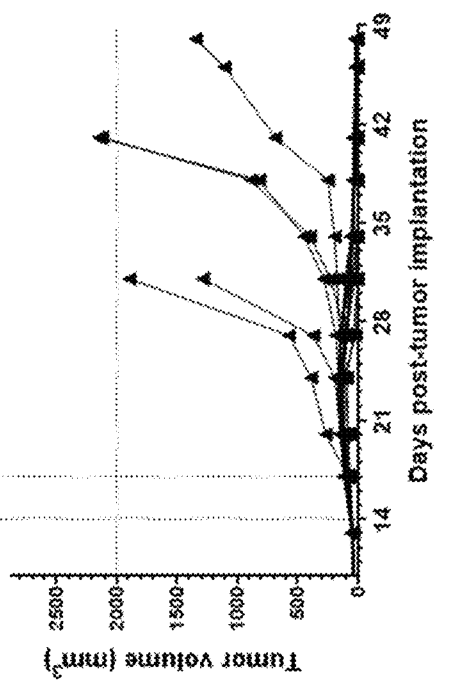

Sera collected from tumor-bearing mice at 24 and 72 hour time points following intratumoral treatment with vehicle or transgene-armed Cop and WR vaccinia virus were also analyzed to quantify circulating IL-2 levels by ELISA (FIGS. 15A and 15B). At the 24 hr post-dosing time point, all mIL-2v transgene-armed Cop and WR vaccinia virus treatment groups produced elevated serum levels of IL-2 that were on average statistically higher than vehicle and paired reporter transgene-armed virus treated groups (FIG. 15A, One-way ANOVA). A similar result was also observed at the 72 hr post-dosing time point (FIG. 15B), with the exception that mice treated with a mIL-2v transgene-armed Cop vaccinia virus without the A34R-K151E substitution (Cop.mIL-2v; VV38) no longer produced statistically elevated serum levels of IL-2 over the vehicle or paired reporter transgene-armed vaccinia virus (Cop.Luc-GFP). These data demonstrate that more than one vaccinia virus strain or variant can be utilized as a vector to deliver a functional IL-2v transgene.

FIGS. 13A-13B Immunophenotype profiling of TIL after intratumoral virotherapy using transgene-armed WR vaccinia viruses. TIL were isolated from MC38 tumor-bearing C57BL/6 female mice on day 17 post-tumor implant and then stained using a cocktail of fluorophore-labeled antibodies to quantify the frequency of NK cell and CD8+ T cell populations among total live CD45+ TIL by flow cytometry. Each graph shows the measured frequency of the indicated cell population 7-days following injection of 60 μL vehicle or 60 μL containing 1e5 pfu WR vaccinia virus armed with either a Luciferase-GFP reporter (WR.Luc-GFP) or a mIL-2v (WR.mIL-2v; VV39) transgene. Each symbol represents the value for an individual mouse, while bars represent group geometric mean. Error bars represent standard deviation. Statistical comparisons between groups were performed using one-way ANOVA; post-hoc comparisons between groups are reported on each graph as p values.

FIGS. 14A-14C. Host cellular responses to vaccinia viral antigens and MC38 tumor antigens following initial virotherapy. Splenocytes recovered at day 17 from C57BL/6 female mice implanted with MC38 tumor cells on day 0 and injected intratumorally with vehicle or transgene-armed WR vaccinia virus on day 10 were restimulated overnight in culture media +/− peptides derived from the vaccinia protein B8, a MuLV peptide expressed by MC38 cells (p15E), or γ-irradiated MC38 cells in 96-well culture plates containing media with Brefeldin A. After 15-19 hr, cells were harvested, stained for surface markers and viability, then fixed and permeabilized to stain for intracellular IFN-γ. The frequency of live CD8+ T cells producing IFN-γ in each sample were detected and enumerated by flow cytometry and are represented as mean % IFN-γ+CD8+ T cells per total live splenocytes. Each symbol represents the value for an individual mouse, while bars represent group geometric mean. Error bars represent standard deviation. Statistical comparisons between groups were performed using 1-way ANOVA; post-hoc comparisons between groups are reported on each graph as p values.

FIGS. 15A and 15B. IL-2 levels detected in sera collected from MC38 tumor-bearing C57BL/6 female mice 24 hr (A) and 72 hr (B) after intratumoral injection with vehicle, transgene-armed Cop vaccinia viruses, or transgene-armed WR vaccinia viruses. Each symbol represents the calculated IL-2 serum levels for an individual mouse, while bars represent group geometric mean (N=2-9/group). Error bars represent 95% confidence intervals. Statistical comparisons between groups were performed on log-transformed data using 1-way ANOVA; results are presented as p values.

Example 5 mIL-2v-Armed Vaccinia Virus Activity in Lewis Lung Carcinoma (LLC) Tumor-Bearing C57BL/6 Mice C57BL/6 female mice were implanted SC on the right flank with 1e5 LLC tumor cells. Thirteen days after tumor cell implantation, mice were randomized based on tumor volume into separate treatment groups (average tumor volume per group ~50 $mm^3$; N=20/group). On days 14 and 17 post-tumor cell implantation, mice were injected intravenously (IV) with 100 μL of vehicle only or vehicle containing 5e7 pfu transgene-armed (reporter or mIL-2v) WR vaccinia virus ±the A34R-K151E substitution. Tumor-bearing mice were observed daily, and both tumor volumes and body weights measured bi-weekly until mice were humanely sacrificed either due to i) tumor volume surpassing 2000 $mm^3$, ii) ≥20% body weight loss, iii) severely diminished health status, or iv) study termination.

Figure 18:
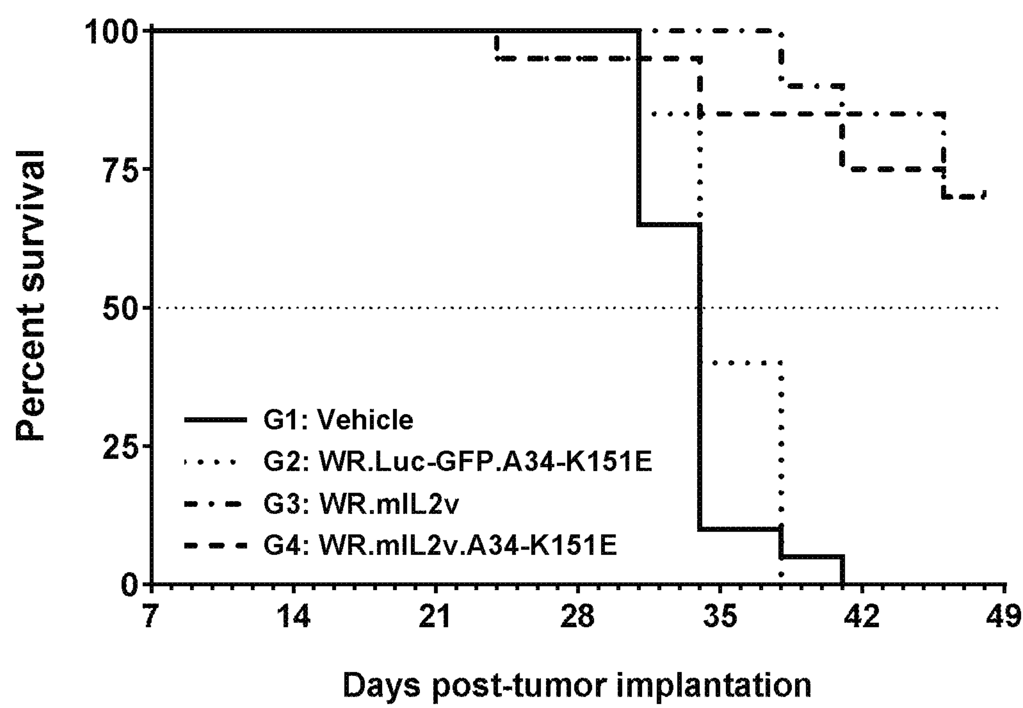
FIG. 18 depicts survival of LLC tumor-bearing C57BL/6 female mice following IV treatment with vehicle, or a recombinant oncolytic vaccinia virus of the present disclosure, on days 14 and 17 after SC tumor implantation.

Comparisons between tumor growth profiles of groups treated with vehicle only or WR vaccinia viruses containing either a Luc-GFP reporter or mIL-2v transgene showed an early phase of tumor growth inhibition associated with virus treatment regardless of transgene arming (FIGS. 16A-16E; and FIG. 17, which presents Table 4, ANCOVA results). At later time points, strong and continued statistically significant tumor growth inhibition was only associated with treatment using mIL-2v transgene-armed WR virus. This tumor growth inhibition was observed in mIL-2v transgene-armed WR viruses in both the presence and absence of the A34R-K151E substitution (FIGS. 16A-16E). With respect to survival, virotherapy with mIL-2v transgene-armed WR virus ±the A34R-K151E substitution also led to substantial and distinguishable increases in overall group survival as compared to either vehicle or reporter-containing WR virus treatment (FIG. 18). This outcome further extends the utility of IL-2v transgene-armed vaccinia virus treatment to another tumor type as well as use of IV delivery as an effective virotherapy option.

FIGS. 16A-16E. Assessment of virotherapy-induced tumor growth inhibition using IV delivery on C57BL/6 female mice implanted SC with LLC tumor cells. Tumor growth trajectories are shown for each treatment group up through day 31 post-tumor implantation (A) or for individual mice in each group until time of sacrifice or study termination (B). Treatment groups included injection with 100 μL of vehicle only, 100 μL of vehicle containing 5e7 pfu WR vaccinia virus ±the A34R-K151E substitution and armed with either a Luc-GFP reporter transgene (WR.Luc-GFP.A34R-K151E) or a mIL-2v transgene (WR.mIL-2 or WR.mIL-2v.A34R-K151E). Dashed vertical lines on each graph represent time points when mice received IV injections of vehicle or virus. The dashed horizontal line on each graph represents the tumor volume threshold used as a criterion to remove animals from the study.

FIG. 17 presents Table 4. Statistical comparison of virotherapy-induced tumor growth inhibition using ANCOVA for subcutaneous LLC tumor model study. Tumor volumes for individual mice in each group on multiple days after treatment were analyzed by ANCOVA to determine statistically significant inhibitory effects on tumor growth across various treatment groups. Columns show the statistical results (p values) of comparisons between specific treatment group pairs. Values in bold font represent comparative ANCOVA results where p values ≤0.05 were observed.

FIG. 18. Survival of LLC tumor-bearing C57BL/6 female mice following IV treatment with vehicle or virus on days 14 and 17 after SC tumor implantation. Mice were designated as deceased on a daily basis upon reaching one or more criteria for humane sacrifice (tumor volume ≥2000 $mm^3$, body weight loss ≥20%, and/or severely diminished health status). The point of intersection between each group's curve and the horizontal dashed line indicates the median (50%) survival threshold for the group. P values represent the statistical results of Log-rank test (Mantel-Cox) comparisons between select virus groups.

Figure 19B:
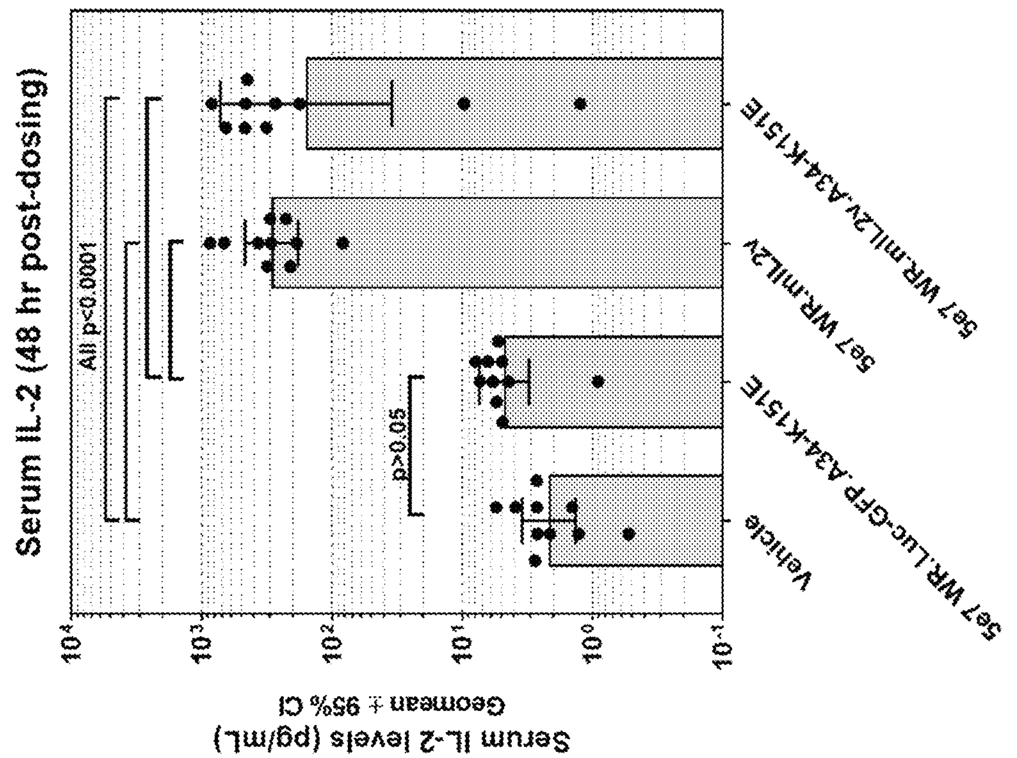
FIGS. 19A and 19B depicts IL-2 levels detected in sera collected from LLC tumor-bearing C57BL/6 female mice 24 hr and 48 hr after IV injection with vehicle or transgene-armed WR vaccinia viruses (recombinant oncolytic vaccinia virus of the present disclosure).
Figure 19A:
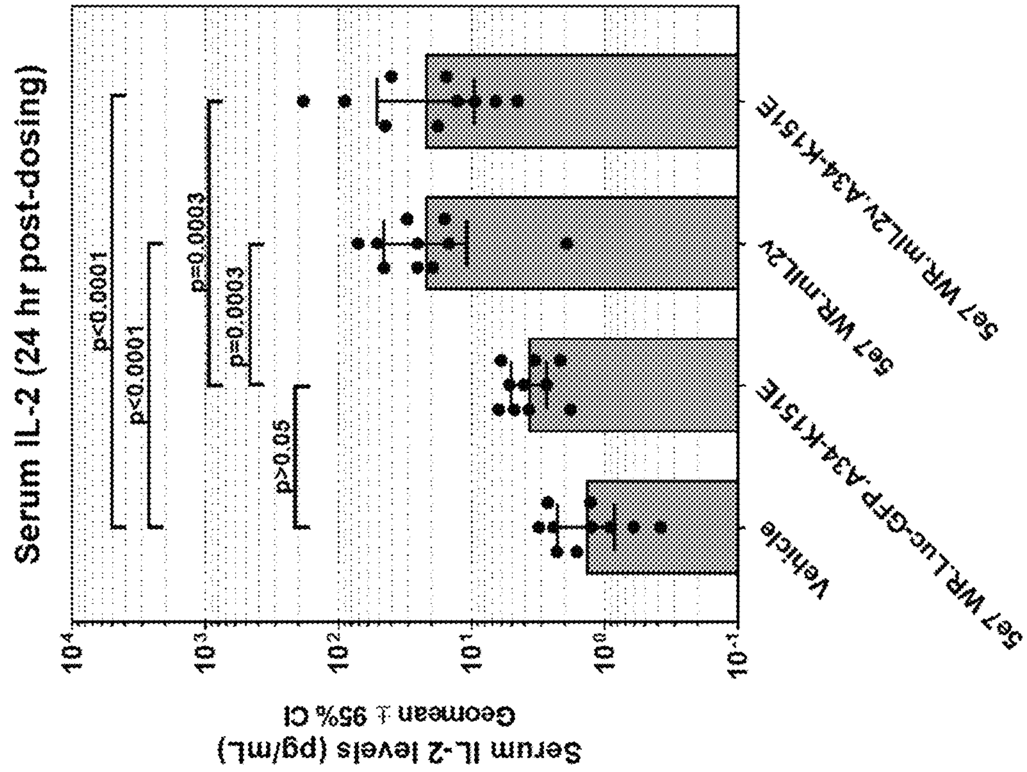

Sera collected from tumor-bearing mice at 24 and 48 hr time points following intratumoral treatment with vehicle or transgene-armed WR vaccinia viruses were also analyzed to quantify circulating IL-2 levels by ELISA. At both time points after dosing, mIL-2v transgene-armed WR viruses produced elevated serum levels of IL-2 that were on average statistically higher than either the vehicle or reporter transgene-containing WR virus treated groups (FIGS. 19A and 19B, One-way ANOVA). In addition to producing enhanced tumor growth inhibition and survival outcomes, the use of mIL-2v transgene-armed WR viruses with and without the A34R K151E substitution led to elevated serum IL-2 levels. These data lend support to the use of IL-2 quantitation in serum samples collected early after virotherapy as a potential biomarker for anti-tumor efficacy for IL-2v-expressing oncolytic Vaccinia viruses.

FIGS. 19A and 19B. IL-2 levels detected in sera collected from LLC tumor-bearing C57BL/6 female mice 24 hr (A) and 48 hr (B) after IV injection with vehicle or transgene-armed WR vaccinia viruses. Each symbol represents the IL-2 serum level detected by ELISA for an individual mouse, while bars represent the group geometric mean (N=10/group and time point). Different cohorts of mice from each group were bled at each designated time point. Statistical comparisons between groups were performed on log-transformed data using one-way ANOVA; results are presented as p values.

Example 6

Single vs. Repeated IV Virotherapy Using mIL-2v-Armed Vaccinia Viruses in MC38 or LLC Tumor-Bearing C57BL/6 Mice In a first set of experiments, C57BL/6 female mice were implanted SC on the right flank with 5e5 MC38 tumor cells. Ten days after tumor cell implantation, mice were randomized based on tumor volume into separate treatment groups (average tumor volume per group ~50 $mm^3$; N=15/group). On day 11 only or days 11, 12 and 13 post-tumor cell implantation, mice were injected IV with 100 μL of vehicle containing 5e7 pfu transgene-armed (reporter or mIL-2v) WR vaccinia virus ±the A34R-K151E substitution. Tumor-bearing mice were observed daily, and both tumor volume and body weight were measured bi-weekly until mice were humanely sacrificed either due to i) tumor volume surpassing 1400 $mm^3$, ii) ≥20% body weight loss, iii) severely diminished health status or iv) study termination.

Figure 20A:
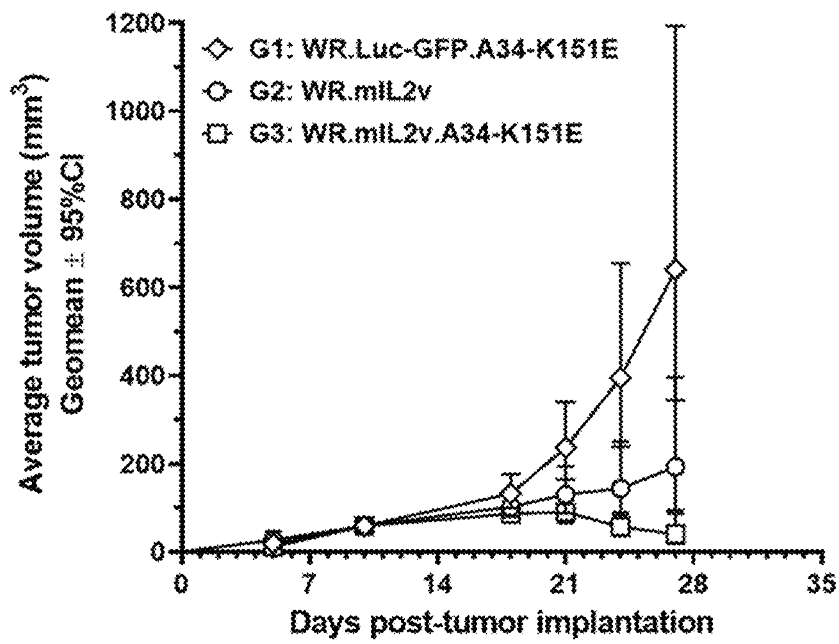
FIGS. 20A-20H depict an assessment of a recombinant oncolytic vaccinia virus of the present disclosure on tumor growth in vivo using single (day 11 only) or repeated (days 11, 12 and 13) IV virus delivery into C57BL/6 female mice implanted SC with MC38 tumor cells.
Figure 20B:
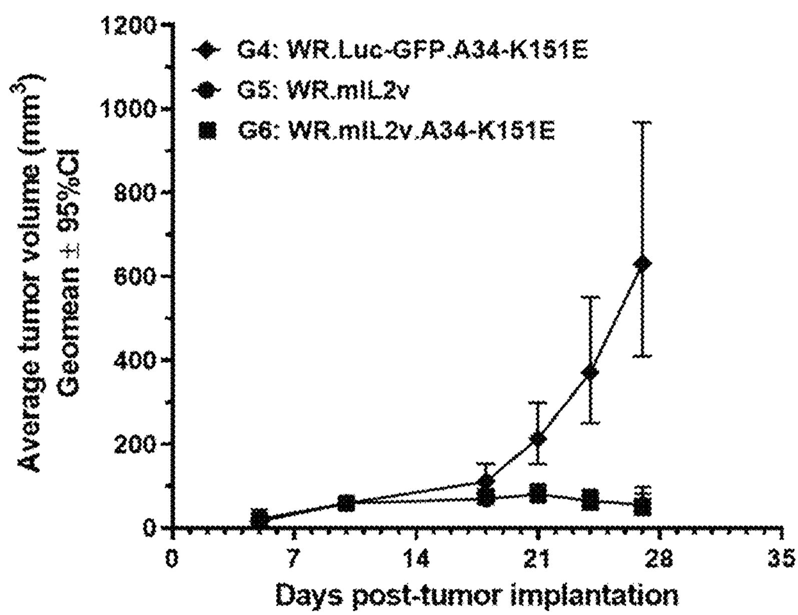
Figure 20C:
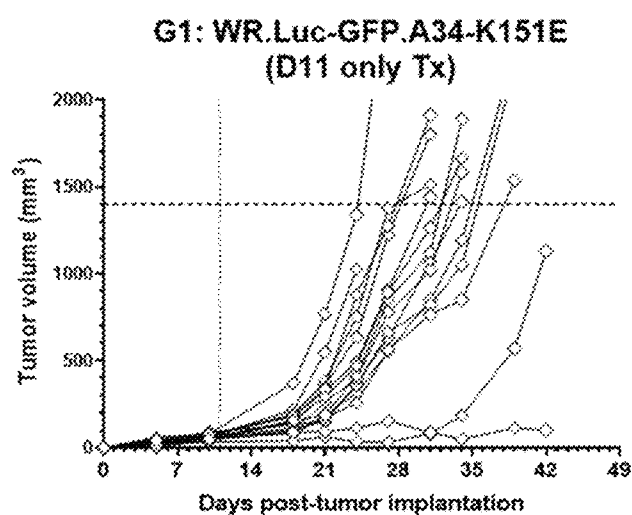
Figure 20D:
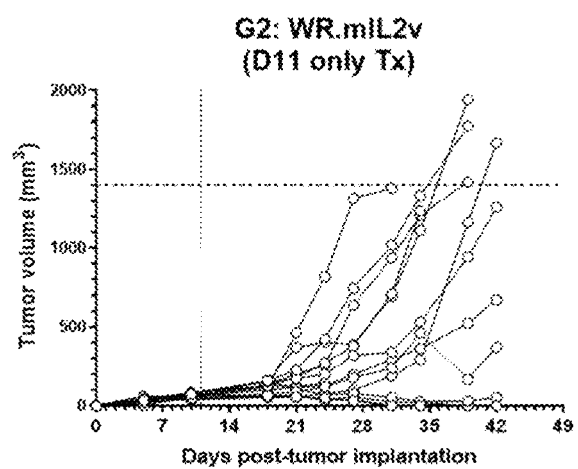
Figure 20E:
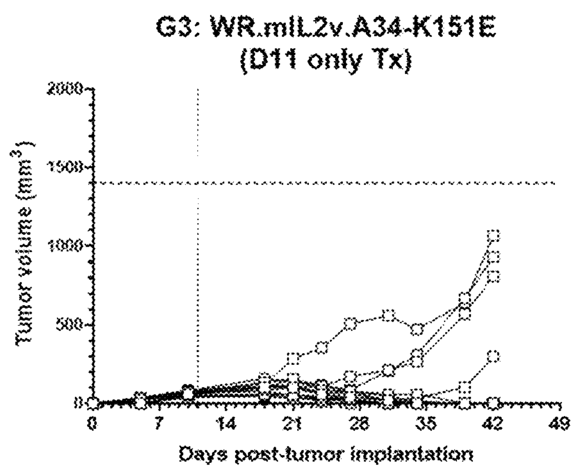
Figure 20F:
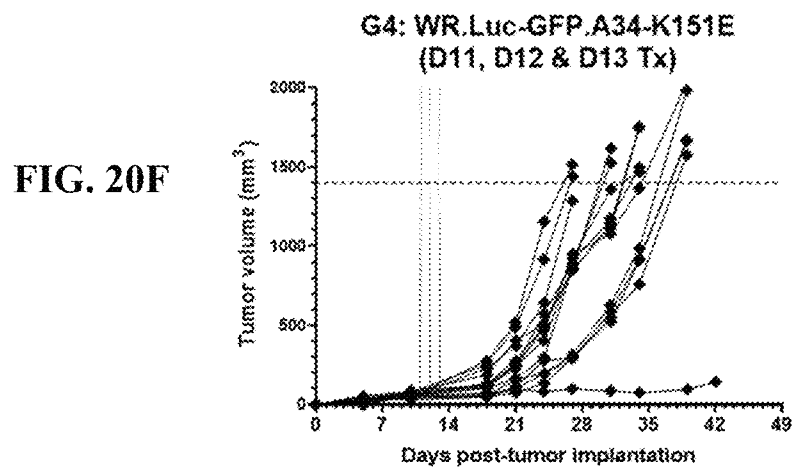
Figure 20G:
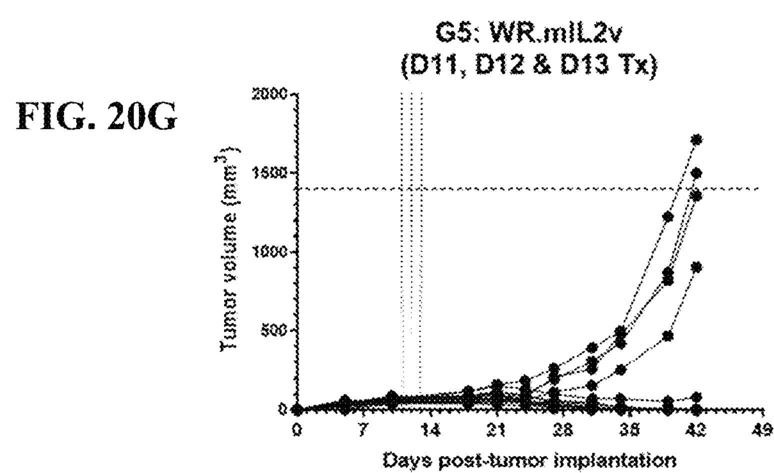
Figure 20H:
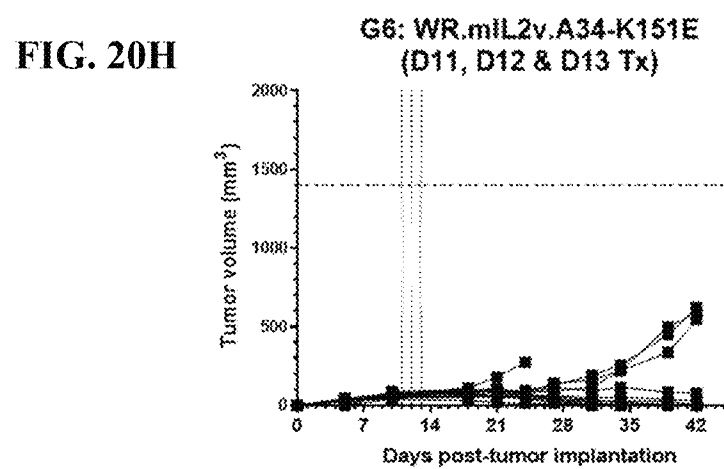
Figure 22A:
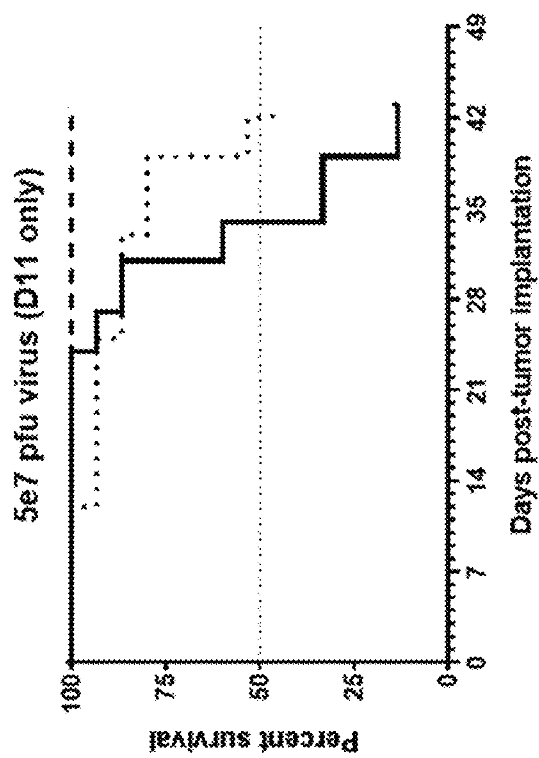
FIGS. 22A-22D depict survival of MC38 tumor-bearing C57BL/6 female mice following IV treatment with vehicle or virus (e.g., recombinant oncolytic vaccinia virus of the present disclosure) on day 11 only or days 11, 12 and 13 after SC tumor implantation.
Figure 22B:
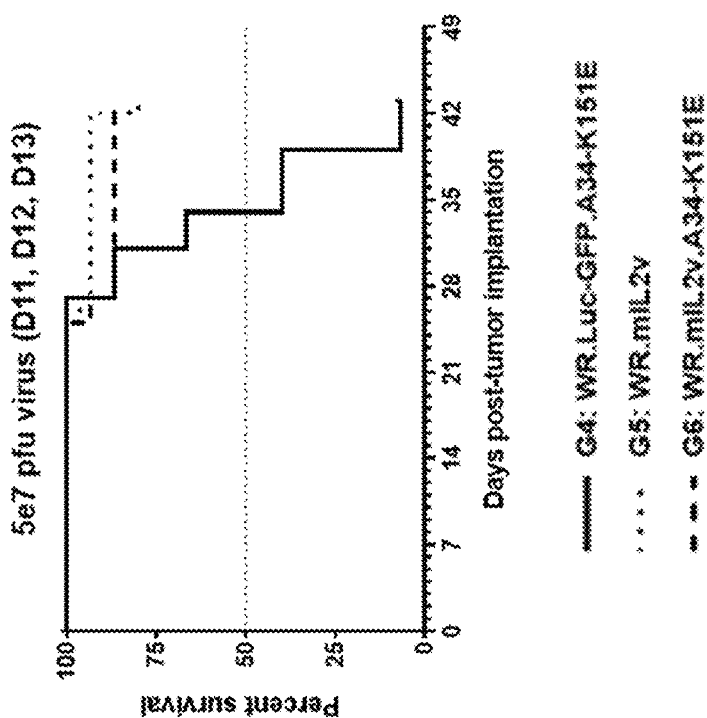
Figure 22C:
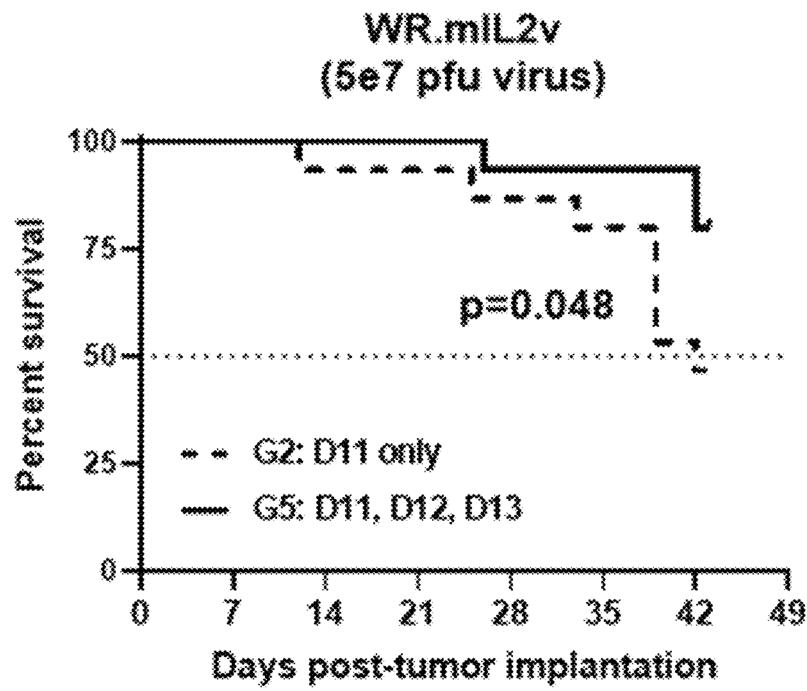
Figure 22D:
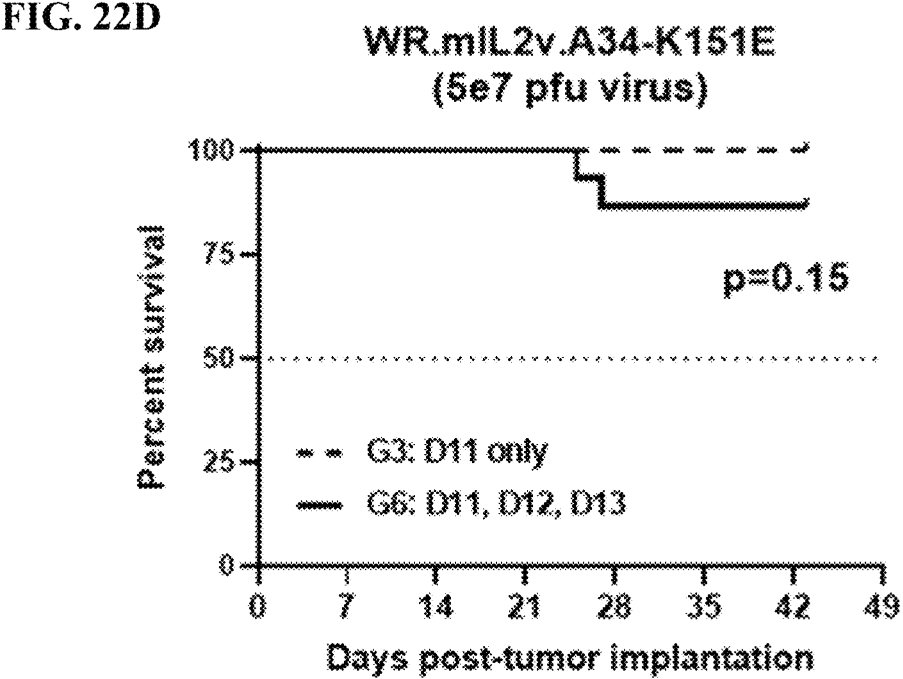

Analysis of tumor growth profiles, shown as group averages for each test virus and dosing schedule (FIGS. 20A and 20B) or as individual mice within each test group (FIGS. 20C-20H), revealed several important findings. First, IV administration of mIL-2v transgene-armed WR viruses (either WR.mIL-2v or WR.mIL-2v.A34R-K151E in this case) led to statistically significant inhibition of MC38 tumor growth compared to reporter transgene-armed WR virus treatment (FIG. 21, which presents Table 5, ANCOVA results). This tumor growth inhibition was observed for mIL-2v transgene-armed WR viruses in both the presence and absence of the A34R K151E substitution and using either single or repeat IV dosing (FIGS. 20C-2H; and FIG. 21, which presents Table 5, ANCOVA results).

Survival results for the same test viruses and dosing schedule groups showed very similar outcomes as those reported above for tumor growth inhibition. This included statistically superior group survival associated with either single or repeat IV dosing of mIL-2v transgene-armed WR viruses in the presence or absence of the A34R-K151E substitution compared to the corresponding Luc-GFP reporter-armed WR viruses (FIGS. 22A-22D). Overall, IV delivery of mIL-2v transgene-armed WR viruses proved to be an effective anti-tumor therapy in the MC38 SC tumor model and demonstrated the potency of even a single therapeutic administration of virus.

Sera were also collected from MC38 tumor-bearing mice in each test group at 24 hr (day 12), 48 hr (day 13) and 72 hr (day 14) after the first IV virus dose for assessment of circulating IL-2 levels. Consistent with other studies where mIL-2v transgene-armed viruses were tested, elevated and statistically significant serum levels of IL-2 were detected in all test groups where mIL-2v transgene-armed WR virus was administered (FIG. 23; and Table 6 (presented in FIG. 24), 2-way ANOVA results). Regardless of the virus dosing schedule or mIL-2v transgene-armed WR virus variant tested, equivalent IL-2 levels were detected across mIL-2v transgene-armed virus groups at each respective time point with levels increasing similarly over time. This suggests that the initial IV dose of mIL-2v-armed WR virus is responsible for the majority of IL-2 released into the blood following dosing.

FIGS. 20A-20H. Assessment of virotherapy-induced tumor growth inhibition using single (day 11 only) or repeated (days 11, 12 and 13) IV virus delivery on C57BL/6 female mice implanted SC with MC38 tumor cells. Tumor growth trajectories are shown for each treatment as group averages up through day 27 post-tumor implantation (A-B) or for individual mice in each group until time of sacrifice or study termination C-H). Test viruses included a Luc-GFP reporter transgene-armed WR virus carrying the A34R-K151E substitution (WR.Luc-GFP.A34R-K151E) and mIL-2v transgene-armed WR vaccinia virus ±the A34R-K151E (WR.mIL-2 and WR.mIL-2v.A34R-K151E). Dashed vertical lines on each graph represent time points when mice received IV injections of virus. The dashed horizontal line on each graph represents the tumor volume threshold used as a criterion to remove animals from the study.

FIG. 21 presents Table 5. Statistical comparison of virotherapy-induced tumor growth inhibition using ANCOVA for subcutaneous MC38 tumor model study. Tumor volumes for individual mice in each group on multiple days after treatment were analyzed by ANCOVA to determine statistically significant inhibitory effects on tumor growth across various treatment groups. Columns show the statistical results (p values) of comparisons between specific treatment group pairs. Values in bold font represent comparative ANCOVA results where p values ≤0.05 were observed.

FIGS. 22A-22D. Survival of MC38 tumor-bearing C57BL/6 female mice following IV treatment with Luc-GFP reporter or mIL-2v transgene-armed WR vaccinia virus on day 11 only (A) or days 11, 12 and 13 (B) after SC tumor implantation. Survival comparisons between groups treated with mIL-2v transgene-armed WR vaccinia without the A34R-K151E substitution on day 11 vs. days 11, 12 and 13 (C) or with mIL-2v transgene-armed WR vaccinia virus with the A34R-K151E substitution on day 11 vs. days 11, 12 and 13 (D) are also shown. Mice were designated on a daily basis as deceased upon reaching one or more criteria for humane sacrifice (tumor volume ≥1400 $mm^3$, body weight loss ≥20%, and/or severely diminished health status). The point of intersection between each group's curve and the horizontal dashed line indicates the median (50%) survival threshold for the group. P values represent the statistical results of Log-rank test (Mantel-Cox) comparisons between select virus groups.

Figure 23:
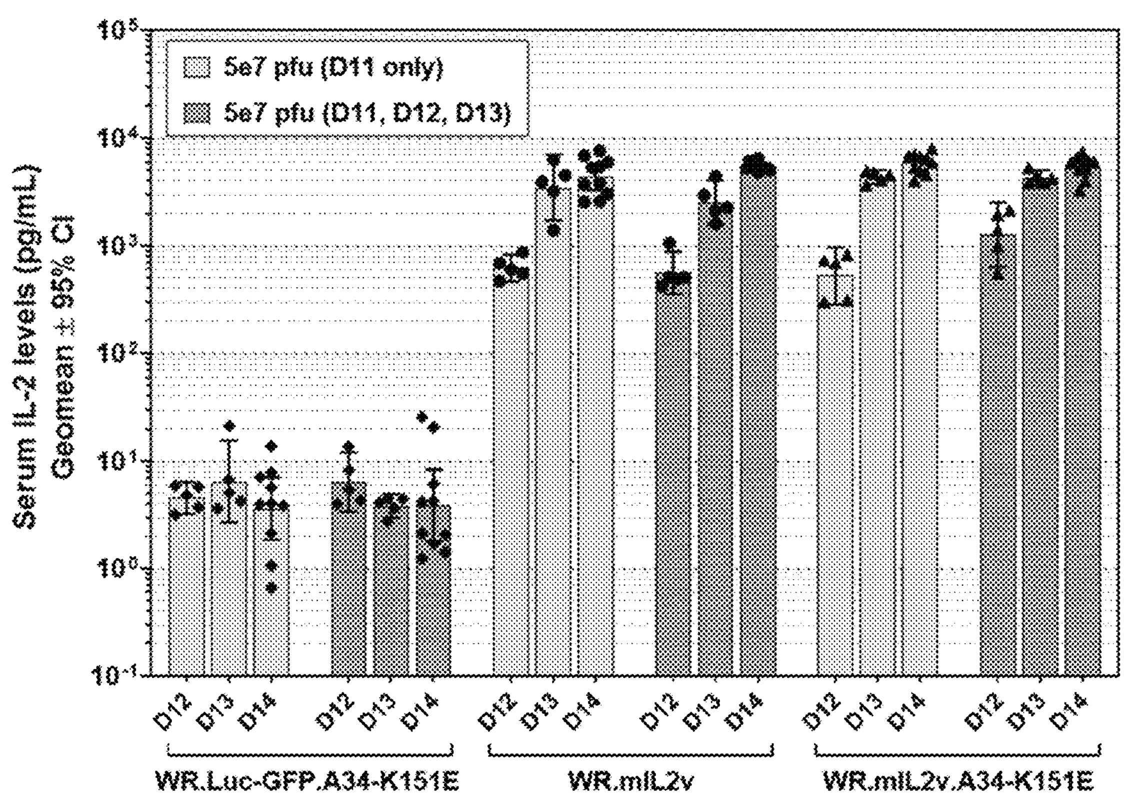
FIG. 23 depicts IL-2 levels detected in sera collected from MC38 tumor-bearing C57BL/6 female mice 24 hr (day 12), 48 hr (day 13) and 72 hr (day 14) after initial IV injection with 5e7 pfu reporter or mIL-2v transgene-armed WR vaccinia viruses.

FIG. 23. IL-2 levels detected in sera collected from MC38 tumor-bearing C57BL/6 female mice 24 hr (day 12), 48 hr (day 13) and 72 hr (day 14) after initial IV injection with 5e7 pfu reporter or mIL-2v transgene-armed WR vaccinia viruses. Each symbol represents IL-2 serum levels detected in an individual mouse, while bars represent the group geometric means (N=5/group and time point). Statistical comparisons between groups and time points were performed on log-transformed data using a two-way ANOVA and are presented in Table 6 (FIG. 24).

FIG. 24 presents Table 6. Statistical comparison of IL-2 levels detected in sera collected from groups of MC38 tumor-bearing mice given one or three separate IV doses of Luc-GFP reporter or mIL-2v transgene-armed WR virus. IL-2 levels for each treatment group were compared across three different sample time points using a 2-way ANOVA statistical analysis. Columns show the statistical results (p values) of comparisons between specific treatment group pairs.

In a second set of experiments, C57BL/6 female mice were implanted SC on the right flank with 1e5 LLC tumor cells. Thirteen days after tumor cell implantation, mice were randomized based on tumor volume into separate treatment groups (average tumor volume per group ~50 $mm^3$; N=25/group). On day 14 only, days 14 and 15, or days 14 and 17 post-tumor cell implantation, mice were injected IV with 100 μL of vehicle containing 5e7 pfu reporter transgene-armed or mIL-2v transgene-armed WR vaccinia viruses carrying the A34R-K151E substitution. Tumor-bearing mice were observed daily, and both tumor volume and body weight were measured bi-weekly until mice were humanely sacrificed either due to i) tumor volume surpassing 2000 $mm^3$, ii) ≥20% body weight loss, iii) severely diminished health status or iv) study termination.

Figure 25D:
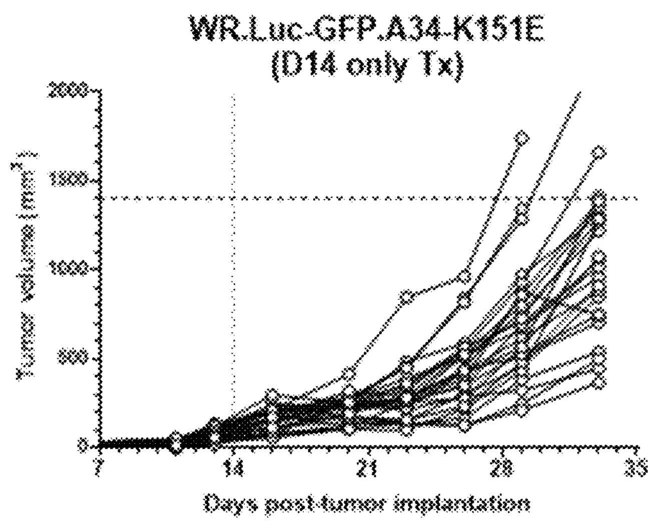
Figure 25E:
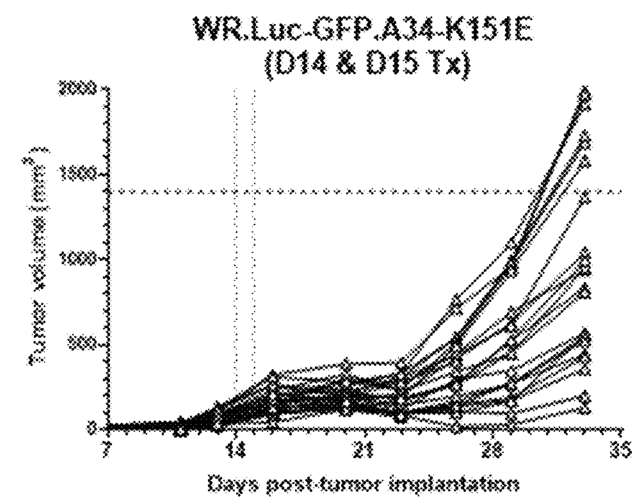
Figure 25F:
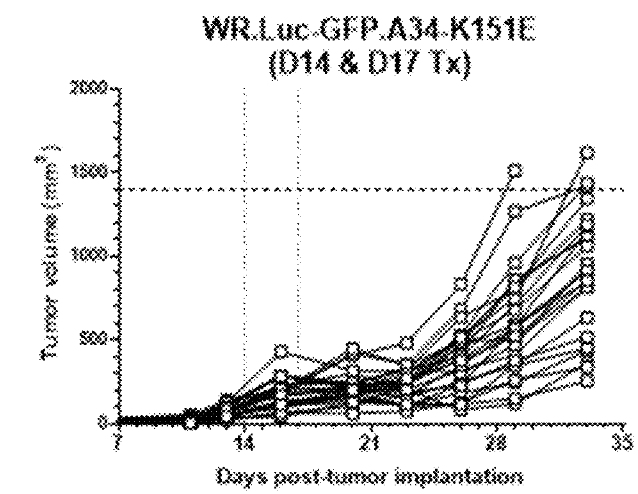
Figure 25G:
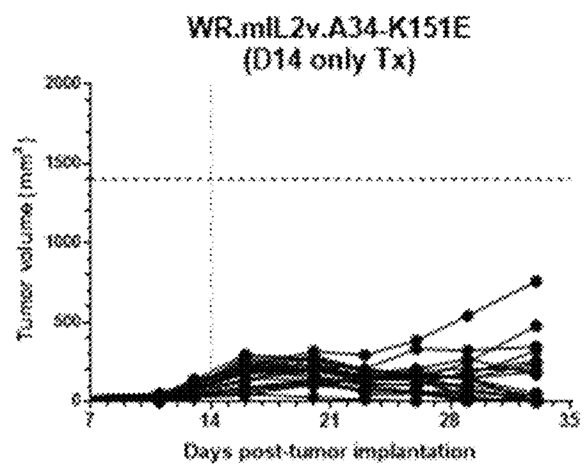
Figure 25H:
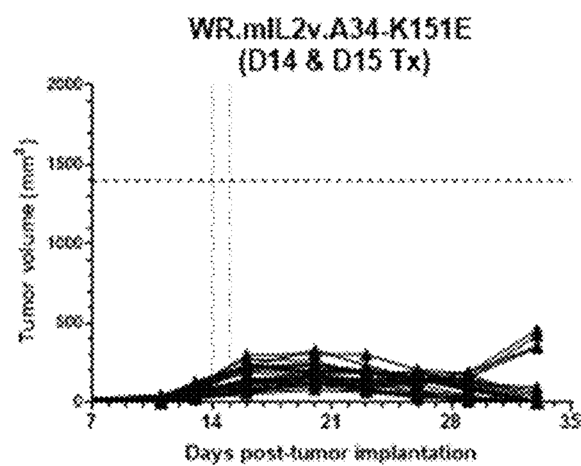
Figure 25I:
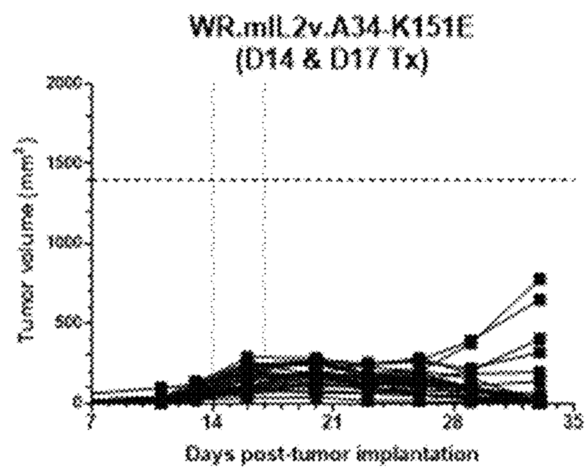

Direct comparison of average tumor growth profiles representing virus groups tested on the same dosing schedule (FIGS. 25A-25C) clearly revealed a superior anti-tumor effect associated with arming vaccinia virus with the mIL-2v transgene (Table 7 (FIG. 26), ANCOVA results) using either single or repeat IV dosing. Furthermore, IL-2 levels in sera collected from animals in each test group at 24 hr (day 15), 48 hr (day 16) and 96 hr (day 18) after the first IV virus dose again demonstrated that both single and repeat administration of mIL-2v-armed WR virus was able to produce persisting IL-2 levels (FIG. 27 and Table 8 (FIG. 28), 2-way ANOVA results).

FIGS. 25A-25I. Assessment of virotherapy-induced tumor growth inhibition using IV delivery on C57BL/6 female mice implanted SC with LLC tumor cells. Tumor growth trajectories are shown for each treatment group (A-C) or for individual mice (D-I) up through study termination at day 33 post-tumor implantation. Treatment groups included injection with 100 μL of vehicle only, 100 μL of vehicle containing 5e7 pfu WR vaccinia virus with the A34R-K151E substitution and armed with either a Luc-GFP reporter transgene (WR.Luc-GFP.A34R-K151E) or mIL-2v transgene (WR.mIL-2.A34R-K151E). Dashed vertical lines on each graph represent time points when mice received IV injections of vehicle or virus. The dashed horizontal line on each graph represents the tumor volume threshold used as a criterion to remove animals from the study.

FIG. 26 presents Table 7. Statistical comparison of virotherapy-induced tumor growth inhibition using ANCOVA for subcutaneous LLC tumor model study. Tumor volumes for individual mice in each group on multiple days after treatment were analyzed by ANCOVA to determine statistically significant inhibitory effects on tumor growth across various treatment groups. Columns show the statistical results (p values) of comparisons between specific treatment group pairs. Values in bold font represent comparative ANCOVA results where p values ≤0.05 were observed.

Figure 27:
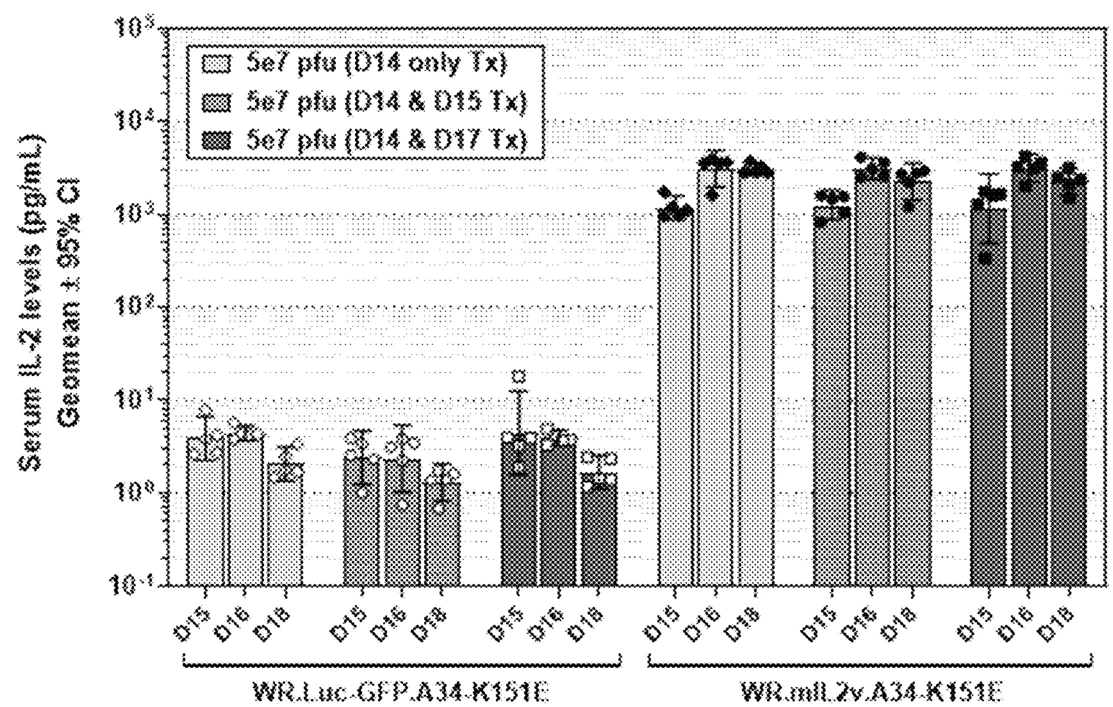
FIG. 27 depicts IL-2 levels detected in sera collected from LLC tumor-bearing C57BL/6 female mice 24 hr (day 15), 48 hr (day 16) and 96 hr (day 18) after initial IV injection with 5e7 pfu reporter or mIL-2v transgene-armed WR vaccinia virus (WR.Luc-GFP.A34R-K151E and WR.mIL-2v.A34R-K151E, respectively).
Figure 29A:
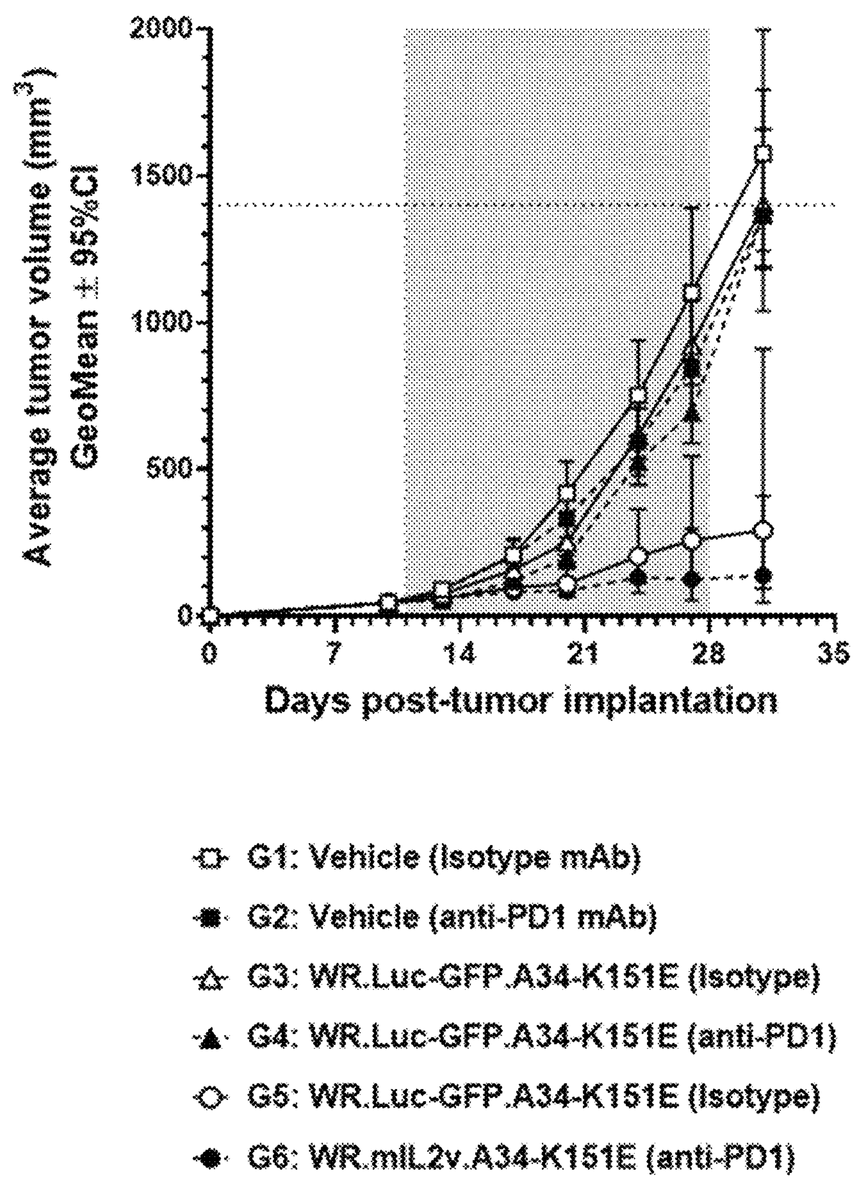

FIG. 27. IL-2 levels detected in sera collected from LLC tumor-bearing C57BL/6 female mice 24 hr (day 15), 48 hr (day 16) and 96 hr (day 18) after initial IV injection with 5e7 pfu reporter or mIL-2v transgene-armed WR vaccinia virus (WR.Luc-GFP.A34R-K151E and WR.mIL-2v.A34R-K151E, respectively). Each symbol represents IL-2 serum levels detected in an individual mouse, while bars represent the group geometric means (N=5/group and time point). Statistical comparisons between groups and time points were performed on log-transformed data using a two-way ANOVA and are presented in Table 8 (FIG. 28).

FIG. 28 presents Table 8. Statistical comparison of IL-2 levels detected in sera collected from groups of LLC tumor-bearing mice given one, two or three separate IV doses of Luc-GFP reporter or mIL-2v transgene-armed WR virus. IL-2 levels for each treatment group were compared across three different sample time points using a 2-way ANOVA statistical analysis. Columns show the statistical results (p values) of comparisons between specific treatment group pairs.

Example 7

Combination Use of mIL-2v-Armed Vaccinia Virus Virotherapy with Checkpoint Inhibition Immunotherapy in MC38 Tumor-Bearing C57BL/6 Mice C57BL/6 female mice were implanted SC on the right flank with 5e5 MC38 tumor cells. Ten days after tumor cell implantation, mice were randomized based on tumor volume into separate treatment groups (average tumor volume per group ~50 $mm^3$; N=15/group). On day 11 post-tumor cell implantation, mice were injected IV with 100 μL of vehicle only or vehicle containing a suboptimal dose (1e7 pfu) of reporter or mIL-2v transgene-armed WR vaccinia virus carrying the A34R-K151E substitution. Concurrent with IV injection of vehicle or virus, mice in each test group were also given a SC injection of 200 μg mouse anti-mouse PD1 antagonist or isotype control monoclonal antibody (mAb). Repeat injections of each mAb were continued on a biweekly basis up through day 28 post-tumor cell implantation. Tumor-bearing mice were observed daily, and both tumor volume and body weight were measured bi-weekly until mice were humanely sacrificed either due to i) tumor volume surpassing 1400 $mm^3$, ii) ≥20% body weight loss, iii) severely diminished health status, or iv) study termination.

A comparison of tumor growth kinetics between groups treated with vehicle and either isotype or anti-PD1 mAb showed similar tumor progression results regardless of the addition of anti-PD1 mAb therapy (FIGS. 29A-29G; and Table 9 (FIG. 30), ANCOVA results). By contrast, groups of mice treated with the Luc-GFP reporter transgene-armed WR virus not only showed early tumor growth inhibition compared to vehicle treatment, but anti-PD1 mAb therapy was able to further improve the tumor growth inhibition induced by the WR.Luc-GFP.A34R-K151E virus across multiple time points (Table 9 (FIG. 30), ANCOVA results for G3 vs. G4). An even more substantial tumor growth inhibition effect, though, including multiple full regressions, was observed when MC38 tumor-bearing mice where treated with the mIL-2v transgene-armed WR virus (WR.mIL-2v.A34R-K151E). Moreover, combining anti-PD1 mAb therapy with use of the WR.mIL-2v.A34R-K151E virus led to both extended and enhanced tumor growth inhibition effects compared to the same virus combined with the isotype control mAb (Table 9 (FIG. 30), ANCOVA results for G5 vs. G6).

Figure 31A:
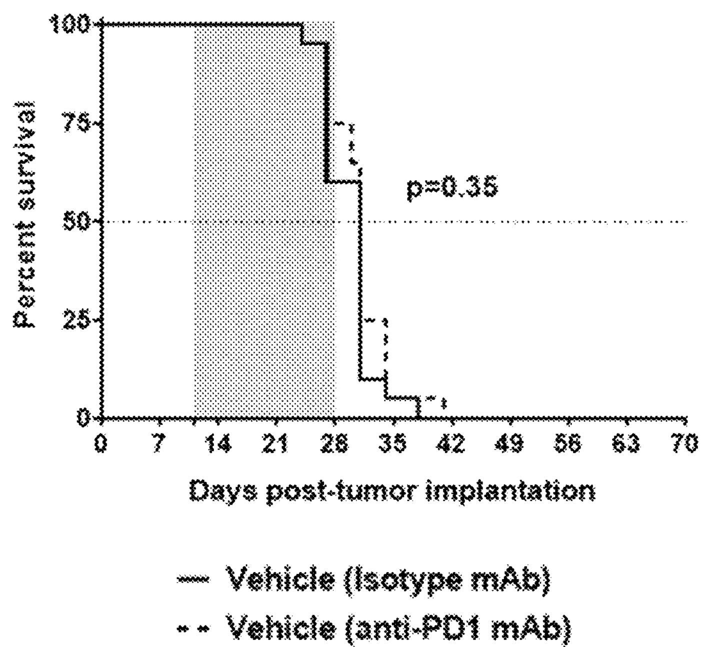
FIGS. 31A-31C depicts survival of MC38 tumor-bearing C57BL/6 female mice following IV treatment with vehicle or virus (e.g., a recombinant oncolytic vaccinia virus of the present disclosure) on day 11 post-tumor implantation together with either biweekly isotype or anti-PD1 monoclonal antibody (mAb) SC injections.
Figure 31B:
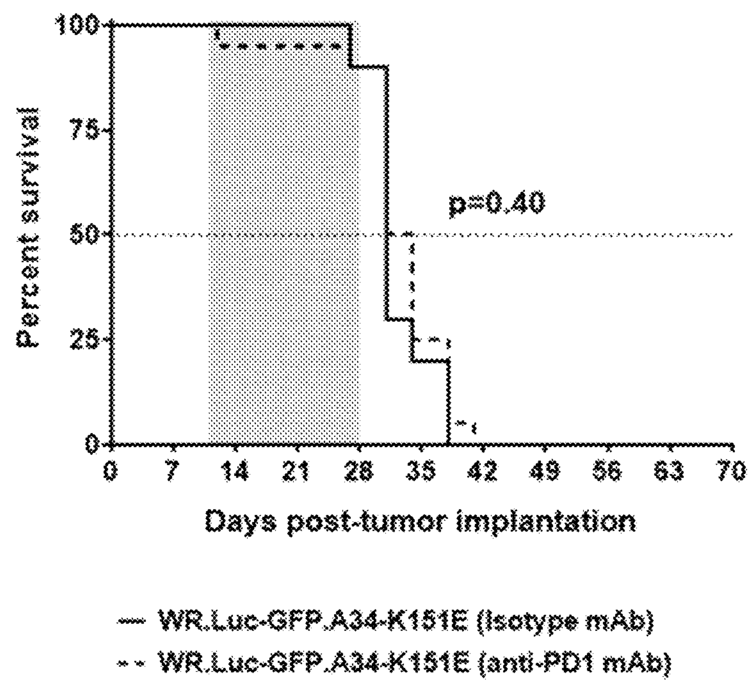
Figure 31C:
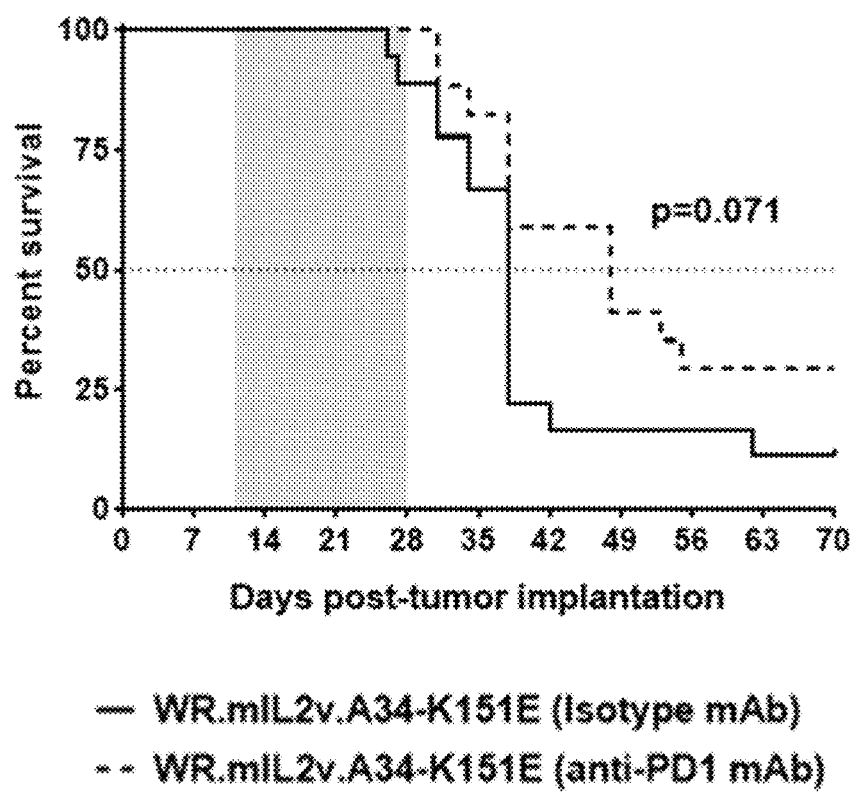

A further analysis of overall survival comparing the effect of combining isotype or anti-PD1 mAb therapy on top of vehicle or virus treatment failed to show that anti-PD1 mAb therapy provided a statistically significant survival advantage. However, a strong trend toward improving the survival benefit associated with use of a suboptimal therapeutic dose of WR.mIL-2v.A34R-K151E was observed (FIGS. 31A-31C). Overall, these results indicate that combining an IL-2v transgene-armed vaccinia virus with checkpoint inhibition therapy is a clinical strategy to treat various human cancers.

FIGS. 29A-29G. Assessment of IV virotherapy combined with checkpoint inhibitor therapy on tumor growth inhibition in C57BL/6 female mice implanted SC with MC38 tumor cells. Tumor growth trajectories are shown for each treatment group up through day 31 post-tumor implantation (A) or for individual mice in each group up through study termination (B-G). Treatment groups included injection with 100 μL of vehicle only, 100 μL of vehicle containing 1e7 pfu WR vaccinia virus with the A34R-K151E substitution and armed with either a Luc-GFP reporter transgene (WR.Luc-GFP.A34R-K151E) or mIL-2v transgene (WR.mIL-2.A34R-K151E). Additionally, test groups of animals were co-administered biweekly SC injection of either an isotype or anti-PD1 mAb. Dashed vertical lines on each graph represents the time point when mice received an IV injection of vehicle or virus. Shaded areas represent the time frame when either isotype or anti-PD1 mAb was administered on a biweekly schedule. The dashed horizontal line on each graph represents the tumor volume threshold used as a criterion to remove animals from the study.

FIG. 30 presents Table 9. Statistical comparison of virotherapy plus isotype or anti-PD1 mAb treatment on tumor growth inhibition using ANCOVA for subcutaneous MC38 tumor model study. Tumor volumes for individual mice in each group on multiple days after treatment were analyzed by ANCOVA to determine statistically significant inhibitory effects on tumor growth across various treatment groups. Columns show the statistical results (p values) of comparisons between specific treatment group pairs. Values in bold font represent comparative ANCOVA results where p values ≤0.05 were observed.

FIGS. 31A-31C. Survival of MC38 tumor-bearing C57BL/6 female mice following IV treatment with vehicle (A) or virus on day 11 post-tumor implantation together with either biweekly isotype or anti-PD1 mAb SC injections (B-C). Mice were designated as deceased on a daily basis upon reaching one or more criteria for humane sacrifice (tumor volume ≥1400 $mm^3$, body weight loss ≥20%, and/or severely diminished health status). The point of intersection between each group's curve and the horizontal dashed line indicates the median (50%) survival threshold for group. P values represent the statistical results of Log-rank test (Mantel-Cox) comparisons between select virus groups.

Example 8

Figure 32A:
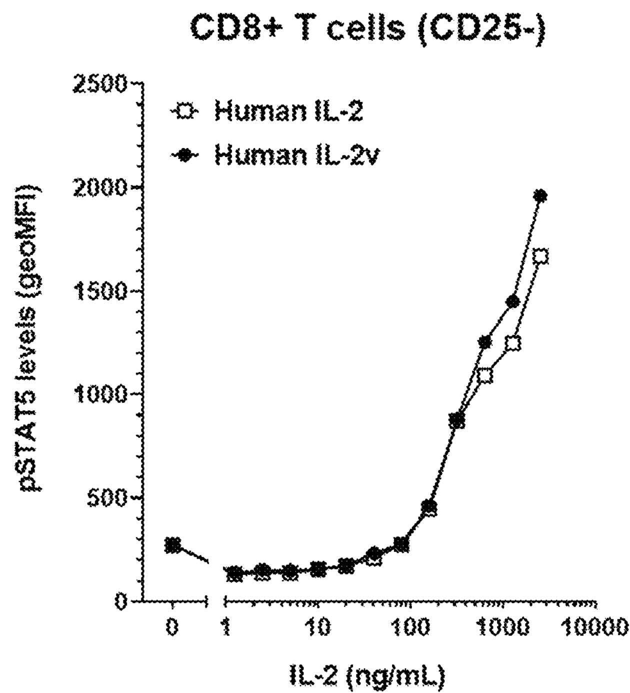
FIGS. 32A and 32B depict a comparison of pSTAT5 induction in (A) CD25− and (B) CD25+ subsets of murine splenocytes following stimulation with either human IL-2 or human IL-2v.
Figure 32B:
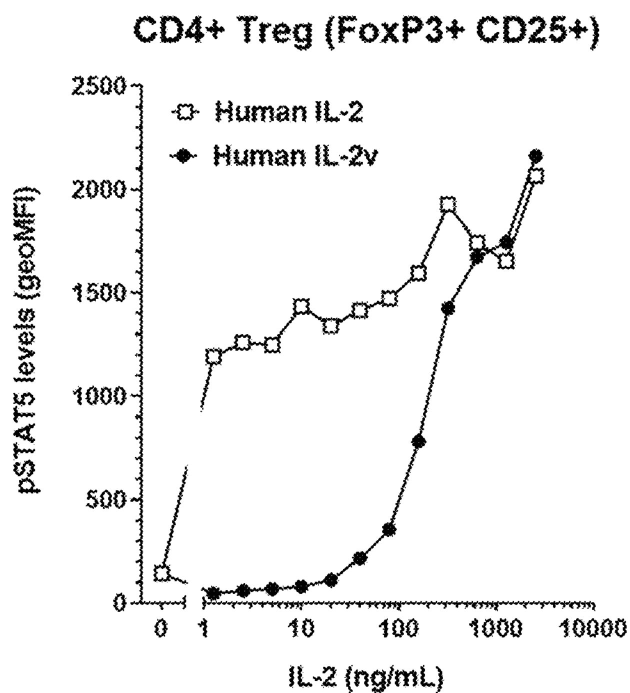

Activity Assessment of hIL-2v Protein Produced from Cells Infected with hIL-2v Transgene-Armed Cop Vaccinia Virus hIL-2v protein expressed and released from HeLa cells infected with a hIL-2v transgene-armed Cop vaccinia virus was evaluated to assess its biological activity on lymphocyte subsets expressing different forms of the IL-2 receptor (IL-2R) complex. An initial intracellular signaling event associated with productive triggering of the IL-2R on cells is the phosphorylation of the STATS protein, which can be detected with phospho-specific antibodies and used as an indirect measure of IL-2 activity. To demonstrate hIL-2v protein produced in human cells retains normal biological activity on cells expressing the intermediate-affinity IL-2R (e.g., resting CD8+ T cells (CD25−)), but also shows a loss of preferential binding to cells expressing the high-affinity IL-2R (e.g., CD25+ CD4+ Treg cells), freshly isolated murine splenocytes were stimulated with increasing protein concentrations of hIL-2v or wild-type recombinant hIL-2 (FIGS. 32A-B). After stimulation for 15 minutes at 37° C., splenocytes were fixed, permeabilized and then stained to detect phospho-STATS (pSTAT5) as well as delineate specific lymphocyte populations.

The results showed that the hIL-2v protein produced by HeLa cells infected with Cop.hIL2v.A34-K151E was equally effective compared to wild-type hIL-2 at inducing increased pSTAT5 levels in resting CD8+ T cells (FIG. 32A). In contrast, the same hIL-2v protein product was found to be less potent than wild-type hIL-2 by several logs at inducing increased pSTAT5 levels in CD25+ CD4+ Treg cells (FIG. 32B). The shift in the pSTAT5 curve in FIG. 32B indicates the hIL-2v protein demonstrated a >95% difference in biological activity compared to wild-type hIL-2. These data are consistent with the expected ability of hIL-2v produced in human cells to be comparable to wild-type hIL-2 at stimulating cells expressing the intermediate-affinity IL-2R, but only weakly active on cells expressing the high-affinity IL-2Rα (i.e. CD25).

FIGS. 32A and 32B. Comparison of pSTAT5 induction in CD25− and CD25+ subsets of murine splenocytes following stimulation with either hIL-2 or hIL-2v. IL-2 activity was assessed using the measurement of intracellular pSTAT5 levels as a readout for productive IL-2R-mediated signaling. Splenocytes were additionally stained with antibodies to cell surface markers (CD3, CD4, CD8, and CD25) and an intracellular protein (FoxP3) to delineate various subsets of murine lymphocytes expressing different IL-2R complexes. Graphs show changes in geometric mean fluorescence intensity (geoMFI) values representative of intracellular staining of pSTAT5 (y-axis) in response to increasing treatment concentrations of hIL-2 or hIL-2v protein (x-axis).

Example 9

Differential Biological Effects of Wild-Type hIL-2 and hIL-2v Expression from Transgene-Armed Vaccinia Viruses Following IV Administration The biological activity of hIL-2 and hIL-2v proteins were compared in vivo by assessing serum levels of cytokines released in response to IV administration of transgene-armed vaccinia viruses. C57BL/6 female mice were implanted SC on the right flank with 2.5e5 B16F10 tumor cells. Ten days after tumor cell implantation, mice were randomized based on tumor volume into separate treatment groups (average tumor volume per group ~30 $mm^3$: N=10/group). On day 12 post-tumor cell implantation, mice were injected IV with 100 μL vehicle only or 100 μL vehicle containing 5e7 pfu transgene-armed, either WR.Luc-2A-GFP reporter transgene (VV3), WR.hIL-2 (VV99) or WR.hIL-2v (VV100) vaccinia virus. Tumor-bearing mice were bled 72 hours after treatment to collect serum for the analysis of hIL-2 and hIL-2v levels as well as several mouse inflammatory response cytokines.

Average serum cytokine levels were measured and compared for each treatment group. Significant findings associated with virotherapy and with the form of hIL-2 or IL-2v expressed by the transgene-armed WR vaccinia viruses were observed (Table 10 (FIG. 33A). (1) IV administered virotherapy with transgene-armed WR vaccinia viruses induced statistical increases in multiple proinflammatory cytokines regardless of the virus transgene payload. This included observed increases in IL-1β, IL-6, IL-10, IL-12p70, IFN-γ and TNF-α associated with virus treatment over vehicle treatment alone (Table 10 (FIG. 33A). (2) B16F10 tumor-bearing mice injected with hIL-2 or hIL-2v transgene-armed WR vaccinia virus were each able to produce detectable hIL-2 and hIL-2v levels, respectively, in the serum and the average measured levels were similar (Table 10 (FIG. 33A). (3) IV administration of hIL-2 but not hIL-2v or reporter transgene-armed WR vaccinia virus caused a further significant elevation in several proinflammatory mouse cytokines, including IL-1β, IL-6, IL-10, IL-12p70, IFN-γ and TNF-α (Table 10 (FIG. 33A). Fold increases in cytokine levels over vehicle treatment for each virus treatment and the percent reduction in proinflammatory cytokine levels associated with use of WR hIL-2v in place of WR hIL-2 were further calculated (Table 11 (FIG. 33B). (4) The findings indicate that the hIL-2v protein produced in vivo from the hIL-2v transgene-armed WR vaccinia virus displayed different biological activities as compared to wild-type hIL-2, likely resulting from a reduced ability of IL-2v to trigger signaling through CD25, that ultimately results in reduced proinflammatory responses.

FIGS. 33A-33B presents Table 10 and Table 11. (A) Serum cytokine levels were measured 72-hr following intravenous treatment of B16F10 tumor-bearing C57BL/6 mice with vehicle or transgene-armed WR vaccinia viruses. Statistical comparisons between cytokine levels detected for each group were performed using a one-way ANOVA with a Tukey's post-hoc multiple group comparison test. Each column shows mean serum cytokine levels (N=10/test group) for the designated cytokine with post-hoc comparison p values displayed below each in parentheses. (B) Fold increase in serum cytokine levels over vehicle treatment and percent reduction in proinflammatory cytokine levels associated with use of WR hIL-2v in place of WR hIL-2 are shown.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A replication-competent, recombinant oncolytic vaccinia virus comprising, in its genome, a nucleotide sequence encoding a variant interleukin 2 (IL-2v) polypeptide comprising the amino acid sequence of SEQ ID NO:9, wherein the nucleotide sequence encoding the variant IL-2v polypeptide comprises the nucleotide sequence of SEQ ID NO:10, SEQ ID NO:11, or SEQ ID NO:12.

2. The vaccinia virus of claim 1, wherein the vaccinia virus comprises a modification to render the vaccinia thymidine kinase deficient.

3. The vaccinia virus of claim 2, wherein the modification results in a lack of J2R expression and/or function.

4. The vaccinia virus of claim 1, wherein the vaccinia virus is a Copenhagen strain vaccinia virus.

5. The vaccinia virus of claim 1, wherein the vaccinia virus is a Western Reserve strain vaccinia virus.

6. The vaccinia virus of claim 1, wherein the vaccinia virus comprises an A34R gene comprising a K151E substitution.

7. A composition comprising:

a) the vaccinia virus of claim 1; and b) a pharmaceutically acceptable excipient.

8. The replication-competent, recombinant oncolytic vaccinia virus of claim 1, wherein the nucleotide sequence encoding the variant interleukin 2 polypeptide comprises the nucleotide sequence of SEQ ID NO:10 or SEQ ID NO:12, and wherein the vaccinia virus is a Copenhagen strain vaccinia virus, is vaccinia thymidine kinase deficient, and comprises an A34R gene comprising a K151E substitution.

9. The replication-competent, recombinant oncolytic vaccinia virus of claim 8, wherein the nucleotide sequence encoding the variant interleukin-2 polypeptide comprises the nucleotide sequence of SEQ ID NO:10.

* * * * *

SEQUENCE LISTING

```
<160> NUMBER OF SEQ ID NOS: 24

<210> SEQ ID NO 1
<211> LENGTH: 133
<212> TYPE: PRT
<213> ORGANISM: Homo sapiens
```

<400> SEQUENCE: 1

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130
```

<210> SEQ ID NO 2
<211> LENGTH: 507
<212> TYPE: DNA
<213> ORGANISM: Artificial Sequence
<220> FEATURE:
<223> OTHER INFORMATION: Synthetic nucleotide

<400> SEQUENCE: 2

```
atgtacagca tgcagctggc cagctgcgtg acactgaccc tcgtgctgct ggtgaacagc     60

gctcctacct cctccagcac cagcagcagc accgctgagg cccagcagca gcagcagcaa    120

cagcaacagc agcaacaaca tttagaacag ctgctgatgg atttacaaga actgctgtct    180

cgtatggaga actatcgtaa tttaaagctg cctcgtatgc tgaccgccaa gttcgcttta    240

cccaagcaag ctacagagct gaaggattta cagtgtttag aggacgagct gggccctctg    300

aggcatgtgc tggacggcac ccagagcaag agcttccagc tggaggacgc cgagaacttt    360

atcagcaaca ttcgtgtgac cgtggtgaag ctgaagggca gcgacaacac cttcgagtgc    420

cagttcgacg acgagagcgc cacagtggtg gactttttaa gaaggtggat cgccttctgc    480

cagtccatca tcagcaccag cccccag                                        507
```

<210> SEQ ID NO 3
<211> LENGTH: 169
<212> TYPE: PRT
<213> ORGANISM: Artificial Sequence
<220> FEATURE:
<223> OTHER INFORMATION: Synthetic polypeptide

<400> SEQUENCE: 3

```
Met Tyr Ser Met Gln Leu Ala Ser Cys Val Thr Leu Thr Leu Val Leu
1               5                   10                  15

Leu Val Asn Ser Ala Pro Thr Ser Ser Ser Thr Ser Ser Ser Thr Ala
            20                  25                  30

Glu Ala Gln Gln Gln Gln Gln Gln Gln Gln Gln Gln Gln Gln His Leu
        35                  40                  45

Glu Gln Leu Leu Met Asp Leu Gln Glu Leu Leu Ser Arg Met Glu Asn
    50                  55                  60
```

```
Tyr Arg Asn Leu Lys Leu Pro Arg Met Leu Thr Ala Lys Phe Ala Leu
65                  70                  75                  80

Pro Lys Gln Ala Thr Glu Leu Lys Asp Leu Gln Cys Leu Glu Asp Glu
                85                  90                  95

Leu Gly Pro Leu Arg His Val Leu Asp Gly Thr Gln Ser Lys Ser Phe
            100                 105                 110

Gln Leu Glu Asp Ala Glu Asn Phe Ile Ser Asn Ile Arg Val Thr Val
        115                 120                 125

Val Lys Leu Lys Gly Ser Asp Asn Thr Phe Glu Cys Gln Phe Asp Asp
    130                 135                 140

Glu Ser Ala Thr Val Val Asp Phe Leu Arg Arg Trp Ile Ala Phe Cys
145                 150                 155                 160

Gln Ser Ile Ile Ser Thr Ser Pro Gln
                165
```

<210> SEQ ID NO 4
<211> LENGTH: 1962
<212> TYPE: DNA
<213> ORGANISM: Artificial Sequence
<220> FEATURE:
<223> OTHER INFORMATION: Synthetic nucleotide

<400> SEQUENCE: 4

```
gattacgacg tgctaatcta gcgtgtgaag acgataaatt aatgatctat ggattaccat     60

ggatgacaac tcaaacatct gcgttatcaa taaatagtaa accgatagtg tataaagatt    120

gtgcaaagct tttgcgatca ataaatggat cacaaccagt atctcttaac gatgttcttc    180

gcagatgatg attcattttt taagtatttg gctagtcaag atgatgaatc ttcattatct    240

gatatattgc aaatcactca atatctagac tttctgttat tattattgat ccaatcaaaa    300

aataaattag aagccgtggg tcattgttat gaatctcttt cagaggaata cagacaattg    360

acaaaattca cagactctca agattttaaa aaactgttta acaaggtccc tattgttaca    420

gatggaaggg tcaaacttaa taaaggatat ttgttcgact ttgtgattag tttgatgcga    480

ttcaaaaaag aatcctctct agctaccacc gcaatagatc ctattagata catagatcct    540

cgtcgcgata tcgcattttc taacgtgatg gatatattaa agtcgaataa agtgaacaat    600

aattaattct ttattgtcat catgaacggg cgcgcctata aaaattgaaa ttttattttt    660

tttttttgga atataaatat ccctatcagt gatagagatc tccctatcag tgatagagag    720

ccaccatgta cagcatgcag ctggccagct gcgtgacact gaccctcgtg ctgctggtga    780

acagcgctcc tacctcctcc agcaccagca gcagcaccgc tgaggcccag cagcagcagc    840

agcaacagca acagcagcaa caacatttag aacagctgct gatggattta caagaactgc    900

tgtctcgtat ggagaactat cgtaatttaa agctgcctcg tatgctgacc gccaagttcg    960

ctttacccaa gcaagctaca gagctgaagg atttacagtg tttagaggac gagctgggcc   1020

ctctgaggca tgtgctggac ggcacccaga gcaagagctt ccagctggag gacgccgaga   1080

actttatcag caacattcgt gtgaccgtgg tgaagctgaa gggcagcgac aacaccttcg   1140

agtgccagtt cgacgacgag agcgccacag tggtggactt tttaagaagg tggatcgcct   1200

tctgccagtc catcatcagc accagccccc agtaatgagc gatcgcgtgt agaaagtgtt   1260

acatcgactc ataatattat attttttatc taaaaaacta aaaataaaca ttgattaaat   1320

tttaatataa tacttaaaaa tggatgttgt gtcgttagat aaaccgttta tgtattttga   1380

ggaaattgat aatgagttag attacgaacc agaaagtgca aatgaggtcg caaaaaaact   1440
```

```
gccgtatcaa ggacagttaa aactattact aggagaatta ttttttctta gtaagttaca   1500

gcgacacggt atattagatg gtgccaccgt agtgtatata ggatcggctc ctggtacaca   1560

tatacgttat ttgagagatc atttctataa tttaggaatg attatcaaat ggatgctaat   1620

tgacggacgc catcatgatc ctattctaaa tggattgcgt gatgtgactc tagtgactcg   1680

gttcgttgat gaggaatatc tacgatccat caaaaaacaa ctgcatcctt ctaagattat   1740

tttaatttct gatgtaagat ccaaacgagg aggaaatgaa cctagtacgg cggatttact   1800

aagtaattac gctctacaaa atgtcatgat tagtatttta aaccccgtgg catctagtct   1860

taaatggaga tgcccgtttc cagatcaatg gatcaaggac ttttatatcc cacacggtaa   1920

taaaatgtta caacctttg ctccttcata ttcagctgaa at                       1962
```

<210> SEQ ID NO 5
<211> LENGTH: 1954
<212> TYPE: DNA
<213> ORGANISM: Artificial Sequence
<220> FEATURE:
<223> OTHER INFORMATION: Synthetic nucleotide

<400> SEQUENCE: 5

```
gattacgacg tgctaatcta gcgtgtgaag acgataaatt aatgatctat ggattaccat     60

ggatgacaac tcaaacatct gcgttatcaa taaatagtaa accgatagtg tataaagatt    120

gtgcaaagct tttgcgatca ataaatggat cacaaccagt atctcttaac gatgttcttc    180

gcagatgatg attcattttt taagtatttg gctagtcaag atgatgaatc ttcattatct    240

gatatattgc aaatcactca atatctagac tttctgttat tattattgat ccaatcaaaa    300

aataaattag aagccgtggg tcattgttat gaatctcttt cagaggaata cagacaattg    360

acaaaattca cagactttca agattttaaa aaactgttta acaaggtccc tattgttaca    420

gatggaaggg tcaaacttaa taaaggatat ttgttcgact ttgtgattag tttgatgcga    480

ttcaaaaaag aatcctctct agctaccacc gcaatagatc ctgttagata catagatcct    540

cgtcgcaata tcgcattttc taacgtgatg gatatattaa agtcgaataa agtgaacaat    600

aattaattct ttattgtcat catgaacgta taaaaattga aattttattt tttttttttg    660

gaatataaat atccctatca gtgatagaga tctccctatc agtgatagag agccaccatg    720

tacagcatgc agctggccag ctgcgtgaca ctgaccctcg tgctgctggt gaacagcgct    780

cctacctcct ccagcaccag cagcagcacc gctgaggccc agcagcagca gcagcaacag    840

caacagcagc aacaacattt agaacagctg ctgatggatt tacaagaact gctgtctcgt    900

atggagaact atcgtaattt aaagctgcct cgtatgctga ccgccaagtt cgctttaccc    960

aagcaagcta cagagctgaa ggatttacag tgtttagagg acgagctggg ccctctgagg   1020

catgtgctgg acggcaccca gagcaagagc ttccagctgg aggacgccga gaactttatc   1080

agcaacattc gtgtgaccgt ggtgaagctg aagggcagcg acaacacctt cgagtgccag   1140

ttcgacgacg agagcgccac agtggtggac tttttaagaa ggtggatcgc cttctgccag   1200

tccatcatca gcaccagccc ccagtaatga gcgatcgcgt gtagaaagtg ttacatcgac   1260

tcataatatt atatttttta tctaaaaaac taaaaataaa cattgattaa attttaatat   1320

aatacttaaa aatggatgtt gtgtcgttag ataaaccgtt tatgtatttt gaggaaattg   1380

ataatgagtt agattacgaa ccagaaagtg caaatgaggt cgcaaaaaaa ctgccgtatc   1440

aaggacagtt aaaactatta ctaggagaat tattttttct tagtaagtta cagcgacacg   1500

gtatattaga tggtgccacc gtagtgtata taggatctgc tcccggtaca catatacgtt   1560
```

```
atttgagaga tcatttctat aatttaggag tgatcatcaa atggatgcta attgacggcc   1620

gccatcatga tcctatttta aatggattgc gtgatgtgac tctagtgact cggttcgttg   1680

atgaggaata tctacgatcc atcaaaaaac aactgcatcc ttctaagatt attttaattt   1740

ctgatgtgag atccaaacga ggaggaaatg aacctagtac ggcggattta ctaagtaatt   1800

acgctctaca aaatgtcatg attagtattt taaaccccgt ggcgtctagt cttaaatgga   1860

gatgcccgtt tccagatcaa tggatcaagg acttttatat cccacacggt aataaaatgt   1920

tacaaccttt tgctccttca tattcagctg aaat                                1954
```

<210> SEQ ID NO 6
<211> LENGTH: 5869
<212> TYPE: DNA
<213> ORGANISM: Artificial Sequence
<220> FEATURE:
<223> OTHER INFORMATION: Synthetic nucleotide

<400> SEQUENCE: 6

```
tgcattaatg aatcggccaa cgcgcgggga gaggcggttt gcgtattggg cgctcttccg     60

cttcctcgct cactgactcg ctgcgctcgg tcgttcggct gcggcgagcg gtatcagctc    120

actcaaaggc ggtaatacgg ttatccacag aatcagggga taacgcagga aagaacatgt    180

gagcaaaagg ccagcaaaag gccaggaacc gtaaaaaggc cgcgttgctg gcgtttttcc    240

ataggctccg cccccctgac gagcatcaca aaaatcgacg ctcaagtcag aggtggcgaa    300

acccgacagg actataaaga taccaggcgt ttccccctgg aagctccctc gtgcgctctc    360

ctgttccgac cctgccgctt accggatacc tgtccgcctt tctcccttcg ggaagcgtgg    420

cgctttctca tagctcacgc tgtaggtatc tcagttcggt gtaggtcgtt cgctccaagc    480

tgggctgtgt gcacgaaccc cccgttcagc ccgaccgctg cgccttatcc ggtaactatc    540

gtcttgagtc caacacggta agacacgact tatcgccact ggcagcagcc actggtaaca    600

ggattagcag agcgaggtat gtaggcggtg ctacagagtt cttgaagtgg tggcctaact    660

acggctacac tagaagaaca gtatttggta tctgcgctct gctgaagcca gttaccttcg    720

gaaaaagagt tggtagctct tgatccggca aacaaaccac cgctggtagc ggtggttttt    780

ttgtttgcaa gcagcagatt acgcgcagaa aaaaaggatc tcaagaagat cctttgatct    840

tttctacggg gtctgacgct cagtggaacg aaaactcacg ttaagggatt ttggtcatga    900

gattatcaaa aaggatcttc acctagatcc ttttaaatta aaaatgaagt tttaaatcaa    960

tctaaagtat atatgagtaa acttggtctg acagttacca atgcttaatc agtgaggcac   1020

ctatctcagc gatctgtcta tttcgttcat ccatagttgc ctgactcggc gtaatgctct   1080

gccagtgtta caaccaatta accaattctg attagaaaaa ctcatcgagc atcaaatgaa   1140

actgcaattt attcatatca ggattatcaa taccatattt ttgaaaaagc cgtttctgta   1200

atgaaggaga aaactcaccg aggcagttcc ataggatggc aagatcctgg tatcggtctg   1260

cgattccgac tcgtccaaca tcaatacaac ctattaattt cccctcgtca aaaataaggt   1320

tatcaagtga gaaatcacca tgagtgacga ctgaatccgg tgagaatggc aaaagcttat   1380

gcatttcttt ccagacttgt tcaacaggcc agccattacg ctcgtcatca aaatcactcg   1440

catcaaccaa accgttattc attcgtgatt gcgcctgagc gagacgaaat acgcgatcac   1500

tgttaaaagg acaattacaa acaggaatca aatgcaaccg gcgcaggaac actgccagcg   1560

catcaacaat attttcacct gaatcaggat attcttctaa tacctggaat gctgttttcc   1620
```

-continued

```
cggggatcgc agtggtgagt aaccatgcat catcaggagt acggataaaa tgcttgatgg   1680
tcggaagagg cataaattcc gtcagccagt ttagtctgac catctcatct gtaacatcat   1740
tggcaacgct acctttgcca tgtttcagaa acaactctgg cgcatcgggc ttcccataca   1800
atcgatagat tgtcgcacct gattgcccga cattatcgcg agcccattta tacccatata   1860
aatcagcatc catgttggaa tttaatcgcg gcctcgagca agacgtttcc cgttgaatat   1920
ggctcataac accccttgta ttactgttta tgtaagcaga caggtcgacg aattcgatta   1980
cgacgtgcta atctagcgtg tgaagacgat aaattaatga tctatggatt accatggatg   2040
acaactcaaa catctgcgtt atcaataaat agtaaaccga tagtgtataa agattgtgca   2100
aagcttttgc gatcaataaa tggatcacaa ccagtatctc ttaacgatgt tcttcgcaga   2160
tgatgattca tttttaagt atttggctag tcaagatgat gaatcttcat tatctgatat   2220
attgcaaatc actcaatatc tagactttct gttattatta ttgatccaat caaaaaataa   2280
attagaagcc gtgggtcatt gttatgaatc tctttcagag gaatacagac aattgacaaa   2340
attcacagac tctcaagatt ttaaaaaact gtttaacaag gtccctattg ttacagatgg   2400
aagggtcaaa cttaataaag gatatttgtt cgactttgtg attagtttga tgcgattcaa   2460
aaaagaatcc tctctagcta ccaccgcaat agatcctatt agatacatag atcctcgtcg   2520
cgatatcgca ttttctaacg tgatggatat attaaagtcg aataaagtga acaataatta   2580
attctttatt gtcatcatga acgggcgcgc ctataaaaat tgaaatttta tttttttttt   2640
ttggaatata aatatcccta tcagtgatag agatctccct atcagtgata gagagccacc   2700
atggaagatg ccaaaaacat taagaagggc ccagcgccat tctacccact cgaagacggg   2760
accgccggcg agcagctgca caaagccatg aagcgctacg ccctggtgcc cggcaccatc   2820
gcctttaccg acgcacatat cgaggtggac attacctacg ccgagtactt cgagatgagc   2880
gttcggctgg cagaagctat gaagcgctat gggctgaata caaaccatcg gatcgtggtg   2940
tgcagcgaga atagcttgca gttcttcatg cccgtgttgg gtgccctgtt catcggtgtg   3000
gctgtggccc cagctaacga catctacaac gagcgcgagc tgctgaacag catgggcatc   3060
agccagccca ccgtcgtatt cgtgagcaag aaagggctgc aaaagatcct caacgtgcaa   3120
aagaagctac cgatcataca aaagatcatc atcatggata gcaagaccga ctaccagggc   3180
ttccaaagca tgtacacctt cgtgacttcc catttgccac ccggcttcaa cgagtacgac   3240
ttcgtgcccg agagcttcga ccgggacaaa accatcgccc tgatcatgaa cagtagtggc   3300
agtaccggat tgcccaaggg cgtagcccta ccgcaccgca ccgcttgtgt ccgattcagt   3360
catgcccgcg accccatctt cggcaaccag atcatccccg acaccgctat cctcagcgtg   3420
gtgccatttc accacggctt cggcatgttc accacgctgg gctacttgat ctgcggcttt   3480
cgggtcgtgc tcatgtaccg cttcgaggag gagctattct tgcgcagctt gcaagactat   3540
aagattcaat ctgccctgct ggtgcccaca ctatttagct tcttcgctaa gagcactctc   3600
atcgacaagt acgacctaag caacttgcac gagatcgcca gcggcggggc gccgctcagc   3660
aaggaggtag gtgaggccgt ggccaaacgc ttccacctac caggcatccg ccagggctac   3720
ggcctgacag aaacaaccag cgccattctg atcacccccg aaggggacga caagcctggc   3780
gcagtaggca aggtggtgcc cttcttcgag gctaaggtgg tggacttgga caccggtaag   3840
acactgggtg tgaaccagcg cggcgagctg tgcgtccgtg gccccatgat catgagcggc   3900
tacgttaaca accccgaggc tacaaacgct ctcatcgaca aggacggctg gctgcacagc   3960
ggcgacatcg cctactggga cgaggacgag cacttcttca tcgtggaccg gctgaagagc   4020
```

```
ctgatcaaat acaagggcta ccaggtagcc ccagccgaac tggagagcat cctgctgcaa   4080

caccccaaca tcttcgacgc cggggtcgcc ggcctgcccg acgacgatgc cggcgagctg   4140

cccgccgcag tcgtcgtgct ggaacacggt aaaaccatga ccgagaagga gatcgtggac   4200

tatgtggcca gccaggttac aaccgccaag aagctgcgcg gtggtgttgt gttcgtggac   4260

gaggtgccta aaggactgac cggcaagttg gacgcccgca agatccgcga gattctcatt   4320

aaggccaaga agggcggcaa gatcgccgtg ggatcccaga ccctgaactt tgatctgctg   4380

aaactggcag gcgatgtgga aagcaaccca ggcccaatgg tgagcaaggg cgaggagctg   4440

ttcaccgggg tggtgcccat cctggtcgag ctggacggcg acgtaaacgg ccacaagttc   4500

agcgtgtccg gcgagggcga gggcgatgcc acctacggca agctgaccct gaagttcatc   4560

tgcaccaccg gcaagctgcc cgtgccctgg cccaccctcg tgaccaccct gacctacggc   4620

gtgcagtgct tcagccgcta ccccgaccac atgaagcagc acgacttctt caagtccgcc   4680

atgcccgaag gctacgtcca ggagcgcacc atcttcttca aggacgacgg caactacaag   4740

acccgcgccg aggtgaagtt cgagggcgac accctggtga accgcatcga gctgaagggc   4800

atcgacttca aggaggacgg caacatcctg gggcacaagc tggagtacaa ctacaacagc   4860

cacaacgtct atatcatggc cgacaagcag aagaacggca tcaaggtgaa cttcaagatc   4920

cgccacaaca tcgaggacgg cagcgtgcag ctcgccgacc actaccagca gaacaccccc   4980

atcggcgacg gccccgtgct gctgcccgac aaccactacc tgagcaccca gtccgccctg   5040

agcaaagacc ccaacgagaa gcgcgatcac atggtcctgc tggagttcgt gaccgccgcc   5100

gggatcactc tcggcatgga cgagctgtac aagtaatgag cgatcgcgtg tagaaagtgt   5160

tacatcgact cataatatta tattttttat ctaaaaaact aaaaataaac attgattaaa   5220

ttttaatata atacttaaaa atggatgttg tgtcgttaga taaaccgttt atgtattttg   5280

aggaaattga taatgagtta gattacgaac cagaaagtgc aaatgaggtc gcaaaaaaac   5340

tgccgtatca aggacagtta aaactattac taggagaatt atttttttctt agtaagttac   5400

agcgacacgg tatattagat ggtgccaccg tagtgtatat aggatcggct cctggtacac   5460

atatacgtta tttgagagat catttctata atttaggaat gattatcaaa tggatgctaa   5520

ttgacggacg ccatcatgat cctattctaa atggattgcg tgatgtgact ctagtgactc   5580

ggttcgttga tgaggaatat ctacgatcca tcaaaaaaca actgcatcct tctaagatta   5640

ttttaatttc tgatgtaaga tccaaacgag gaggaaatga acctagtacg gcggatttac   5700

taagtaatta cgctctacaa aatgtcatga ttagtatttt aaaccccgtg gcatctagtc   5760

ttaaatggag atgcccgttt ccagatcaat ggatcaagga cttttatatc ccacacggta   5820

ataaaatgtt acaacctttt gctccttcat attcagctga aatgaattc              5869
```

<210> SEQ ID NO 7
<211> LENGTH: 3943
<212> TYPE: DNA
<213> ORGANISM: Artificial Sequence
<220> FEATURE:
<223> OTHER INFORMATION: Synthetic nucleotide

<400> SEQUENCE: 7

```
tgcattaatg aatcggccaa cgcgcgggga gaggcggttt gcgtattggg cgctcttccg     60

cttcctcgct cactgactcg ctgcgctcgg tcgttcggct gcggcgagcg gtatcagctc    120

actcaaaggc ggtaatacgg ttatccacag aatcagggga taacgcagga aagaacatgt    180
```

```
gagcaaaagg ccagcaaaag gccaggaacc gtaaaaaggc cgcgttgctg gcgtttttcc    240
ataggctccg cccccctgac gagcatcaca aaaatcgacg ctcaagtcag aggtggcgaa    300
acccgacagg actataaaga taccaggcgt ttccccctgg aagctccctc gtgcgctctc    360
ctgttccgac cctgccgctt accggatacc tgtccgcctt tctcccttcg ggaagcgtgg    420
cgctttctca tagctcacgc tgtaggtatc tcagttcggt gtaggtcgtt cgctccaagc    480
tgggctgtgt gcacgaaccc cccgttcagc ccgaccgctg cgccttatcc ggtaactatc    540
gtcttgagtc caacacggta agacacgact tatcgccact ggcagcagcc actggtaaca    600
ggattagcag agcgaggtat gtaggcggtg ctacagagtt cttgaagtgg tggcctaact    660
acggctacac tagaagaaca gtatttggta tctgcgctct gctgaagcca gttaccttcg    720
gaaaaagagt tggtagctct tgatccggca aacaaaccac cgctggtagc ggtggttttt    780
ttgtttgcaa gcagcagatt acgcgcagaa aaaaaggatc tcaagaagat cctttgatct    840
tttctacggg gtctgacgct cagtggaacg aaaactcacg ttaagggatt ttggtcatga    900
gattatcaaa aaggatcttc acctagatcc ttttaaatta aaaatgaagt tttaaatcaa    960
tctaaagtat atatgagtaa acttggtctg acagttacca atgcttaatc agtgaggcac   1020
ctatctcagc gatctgtcta tttcgttcat ccatagttgc ctgactcggc gtaatgctct   1080
gccagtgtta caaccaatta accaattctg attagaaaaa ctcatcgagc atcaaatgaa   1140
actgcaattt attcatatca ggattatcaa taccatattt ttgaaaaagc cgtttctgta   1200
atgaaggaga aaactcaccg aggcagttcc ataggatggc aagatcctgg tatcggtctg   1260
cgattccgac tcgtccaaca tcaatacaac ctattaattt cccctcgtca aaaataaggt   1320
tatcaagtga gaaatcacca tgagtgacga ctgaatccgg tgagaatggc aaaagcttat   1380
gcatttcttt ccagacttgt tcaacaggcc agccattacg ctcgtcatca aaatcactcg   1440
catcaaccaa accgttattc attcgtgatt gcgcctgagc gagacgaaat acgcgatcac   1500
tgttaaaagg acaattacaa acaggaatca aatgcaaccg gcgcaggaac actgccagcg   1560
catcaacaat attttcacct gaatcaggat attcttctaa tacctggaat gctgttttcc   1620
cggggatcgc agtggtgagt aaccatgcat catcaggagt acggataaaa tgcttgatgg   1680
tcggaagagg cataaattcc gtcagccagt ttagtctgac catctcatct gtaacatcat   1740
tggcaacgct acctttgcca tgtttcagaa acaactctgg cgcatcgggc ttcccataca   1800
atcgatagat tgtcgcacct gattgcccga cattatcgcg agcccattta tacccatata   1860
aatcagcatc catgttggaa tttaatcgcg gcctcgagca agacgtttcc cgttgaatat   1920
ggctcataac accccttgta ttactgttta tgtaagcaga caggtcgacg aattcgatta   1980
cgacgtgcta atctagcgtg tgaagacgat aaattaatga tctatggatt accatggatg   2040
acaactcaaa catctgcgtt atcaataaat agtaaaccga tagtgtataa agattgtgca   2100
aagcttttgc gatcaataaa tggatcacaa ccagtatctc ttaacgatgt tcttcgcaga   2160
tgatgattca ttttttaagt atttggctag tcaagatgat gaatcttcat tatctgatat   2220
attgcaaatc actcaatatc tagactttct gttattatta ttgatccaat caaaaaataa   2280
attagaagcc gtgggtcatt gttatgaatc tctttcagag gaatacagac aattgacaaa   2340
attcacagac tctcaagatt ttaaaaaact gtttaacaag gtccctattg ttacagatgg   2400
aagggtcaaa cttaataaag gatatttgtt cgactttgtg attagtttga tgcgattcaa   2460
aaaagaatcc tctctagcta ccaccgcaat agatcctatt agatacatag atcctcgtcg   2520
cgatatcgca ttttctaacg tgatggatat attaaagtcg aataaagtga acaataatta   2580
```

```
attctttatt gtcatcatga acgggcgcgc ctataaaaat tgaaatttta ttttttttt   2640

ttggaatata aatatcccta tcagtgatag agatctccct atcagtgata gagagccacc   2700

atgtacagca tgcagctggc cagctgcgtg acactgaccc tcgtgctgct ggtgaacagc   2760

gctcctacct cctccagcac cagcagcagc accgctgagg cccagcagca gcagcagcaa   2820

cagcaacagc agcaacaaca tttagaacag ctgctgatgg atttacaaga actgctgtct   2880

cgtatggaga actatcgtaa tttaaagctg cctcgtatgc tgaccgccaa gttcgcttta   2940

cccaagcaag ctacagagct gaaggattta cagtgtttag aggacgagct gggccctctg   3000

aggcatgtgc tggacggcac ccagagcaag agcttccagc tggaggacgc cgagaacttt   3060

atcagcaaca ttcgtgtgac cgtggtgaag ctgaagggca gcgacaacac cttcgagtgc   3120

cagttcgacg acgagagcgc cacagtggtg gactttttaa gaaggtggat cgccttctgc   3180

cagtccatca tcagcaccag cccccagtaa tgagcgatcg cgtgtagaaa gtgttacatc   3240

gactcataat attatatttt ttatctaaaa aactaaaaat aaacattgat taaattttaa   3300

tataatactt aaaaatggat gttgtgtcgt tagataaacc gtttatgtat tttgaggaaa   3360

ttgataatga gttagattac gaaccagaaa gtgcaaatga ggtcgcaaaa aaactgccgt   3420

atcaaggaca gttaaaacta ttactaggag aattattttt tcttagtaag ttacagcgac   3480

acggtatatt agatggtgcc accgtagtgt atataggatc ggctcctggt acacatatac   3540

gttatttgag agatcatttc tataatttag gaatgattat caaatggatg ctaattgacg   3600

gacgccatca tgatcctatt ctaaatggat tgcgtgatgt gactctagtg actcggttcg   3660

ttgatgagga atatctacga tccatcaaaa aacaactgca tccttctaag attattttaa   3720

tttctgatgt aagatccaaa cgaggaggaa atgaacctag tacggcggat ttactaagta   3780

attacgctct acaaaatgtc atgattagta ttttaaaccc cgtggcatct agtcttaaat   3840

ggagatgccc gtttccagat caatggatca aggactttta tatcccacac ggtaataaaa   3900

tgttacaacc ttttgctcct tcatattcag ctgaaatgaa ttc                     3943
```

<210> SEQ ID NO 8
<211> LENGTH: 3935
<212> TYPE: DNA
<213> ORGANISM: Artificial Sequence
<220> FEATURE:
<223> OTHER INFORMATION: Synthetic nucleotide

<400> SEQUENCE: 8

```
tgcattaatg aatcggccaa cgcgcgggga gaggcggttt gcgtattggg cgctcttccg     60

cttcctcgct cactgactcg ctgcgctcgg tcgttcggct gcggcgagcg gtatcagctc    120

actcaaaggc ggtaatacgg ttatccacag aatcagggga taacgcagga aagaacatgt    180

gagcaaaagg ccagcaaaag gccaggaacc gtaaaaaggc cgcgttgctg gcgtttttcc    240

ataggctccg cccccctgac gagcatcaca aaaatcgacg ctcaagtcag aggtggcgaa    300

acccgacagg actataaaga taccaggcgt ttccccctgg aagctccctc gtgcgctctc    360

ctgttccgac cctgccgctt accggatacc tgtccgcctt tctcccttcg ggaagcgtgg    420

cgctttctca tagctcacgc tgtaggtatc tcagttcggt gtaggtcgtt cgctccaagc    480

tgggctgtgt gcacgaaccc cccgttcagc ccgaccgctg cgccttatcc ggtaactatc    540

gtcttgagtc caacacggta agacacgact tatcgccact ggcagcagcc actggtaaca    600

ggattagcag agcgaggtat gtaggcggtg ctacagagtt cttgaagtgg tggcctaact    660
```

-continued

```
acggctacac tagaagaaca gtatttggta tctgcgctct gctgaagcca gttaccttcg    720
gaaaaagagt tggtagctct tgatccggca aacaaaccac cgctggtagc ggtggttttt    780
ttgtttgcaa gcagcagatt acgcgcagaa aaaaaggatc tcaagaagat cctttgatct    840
tttctacggg gtctgacgct cagtggaacg aaaactcacg ttaagggatt ttggtcatga    900
gattatcaaa aaggatcttc acctagatcc ttttaaatta aaaatgaagt tttaaatcaa    960
tctaaagtat atatgagtaa acttggtctg acagttacca atgcttaatc agtgaggcac   1020
ctatctcagc gatctgtcta tttcgttcat ccatagttgc ctgactcggc gtaatgctct   1080
gccagtgtta caaccaatta accaattctg attagaaaaa ctcatcgagc atcaaatgaa   1140
actgcaattt attcatatca ggattatcaa taccatattt ttgaaaaagc cgtttctgta   1200
atgaaggaga aaactcaccg aggcagttcc ataggatggc aagatcctgg tatcggtctg   1260
cgattccgac tcgtccaaca tcaatacaac ctattaattt cccctcgtca aaaataaggt   1320
tatcaagtga gaaatcacca tgagtgacga ctgaatccgg tgagaatggc aaaagcttat   1380
gcatttcttt ccagacttgt tcaacaggcc agccattacg ctcgtcatca aaatcactcg   1440
catcaaccaa accgttattc attcgtgatt gcgcctgagc gagacgaaat acgcgatcac   1500
tgttaaaagg acaattacaa acaggaatca aatgcaaccg gcgcaggaac actgccagcg   1560
catcaacaat attttcacct gaatcaggat attcttctaa tacctggaat gctgttttcc   1620
cggggatcgc agtggtgagt aaccatgcat catcaggagt acggataaaa tgcttgatgg   1680
tcggaagagg cataaattcc gtcagccagt ttagtctgac catctcatct gtaacatcat   1740
tggcaacgct acctttgcca tgtttcagaa acaactctgg cgcatcgggc ttcccataca   1800
atcgatagat tgtcgcacct gattgcccga cattatcgcg agcccattta tacccatata   1860
aatcagcatc catgttggaa tttaatcgcg gcctcgagca agacgtttcc cgttgaatat   1920
ggctcataac accccttgta ttactgttta tgtaagcaga caggtcgacg aattcgatta   1980
cgacgtgcta atctagcgtg tgaagacgat aaattaatga tctatggatt accatggatg   2040
acaactcaaa catctgcgtt atcaataaat agtaaaccga tagtgtataa agattgtgca   2100
aagcttttgc gatcaataaa tggatcacaa ccagtatctc ttaacgatgt tcttcgcaga   2160
tgatgattca ttttttaagt atttggctag tcaagatgat gaatcttcat tatctgatat   2220
attgcaaatc actcaatatc tagactttct gttattatta ttgatccaat caaaaaataa   2280
attagaagcc gtgggtcatt gttatgaatc tctttcagag gaatacagac aattgacaaa   2340
attcacagac tttcaagatt ttaaaaaact gtttaacaag gtccctattg ttacagatgg   2400
aagggtcaaa cttaataaag gatatttgtt cgactttgtg attagtttga tgcgattcaa   2460
aaaagaatcc tctctagcta ccaccgcaat agatcctgtt agatacatag atcctcgtcg   2520
caatatcgca ttttctaacg tgatggatat attaaagtcg aataaagtga acaataatta   2580
attctttatt gtcatcatga acgtataaaa attgaaattt tatttttttt ttttggaata   2640
taaatatccc tatcagtgat agagatctcc ctatcagtga tagagagcca ccatgtacag   2700
catgcagctg gccagctgcg tgacactgac cctcgtgctg ctggtgaaca gcgctcctac   2760
ctcctccagc accagcagca gcaccgctga ggcccagcag cagcagcagc aacagcaaca   2820
gcagcaacaa catttagaac agctgctgat ggatttacaa gaactgctgt ctcgtatgga   2880
gaactatcgt aatttaaagc tgcctcgtat gctgaccgcc aagttcgctt tacccaagca   2940
agctacagag ctgaaggatt tacagtgttt agaggacgag ctgggccctc tgaggcatgt   3000
gctggacggc acccagagca agagcttcca gctggaggac gccgagaact ttatcagcaa   3060
```

```
cattcgtgtg accgtggtga agctgaaggg cagcgacaac accttcgagt gccagttcga   3120

cgacgagagc gccacagtgg tggacttttt aagaaggtgg atcgccttct gccagtccat   3180

catcagcacc agcccccagt aatgagcgat cgcgtgtaga aagtgttaca tcgactcata   3240

atattatatt ttttatctaa aaaactaaaa ataaacattg attaaatttt aatataatac   3300

ttaaaaatgg atgttgtgtc gttagataaa ccgtttatgt attttgagga aattgataat   3360

gagttagatt acgaaccaga aagtgcaaat gaggtcgcaa aaaaactgcc gtatcaagga   3420

cagttaaaac tattactagg agaattattt tttcttagta agttacagcg acacggtata   3480

ttagatggtg ccaccgtagt gtatatagga tctgctcccg gtacacatat acgttatttg   3540

agagatcatt tctataattt aggagtgatc atcaaatgga tgctaattga cggccgccat   3600

catgatccta ttttaaatgg attgcgtgat gtgactctag tgactcggtt cgttgatgag   3660

gaatatctac gatccatcaa aaaacaactg catccttcta agattatttt aatttctgat   3720

gtgagatcca aacgaggagg aaatgaacct agtacggcgg atttactaag taattacgct   3780

ctacaaaatg tcatgattag tattttaaac cccgtggcgt ctagtcttaa atggagatgc   3840

ccgtttccag atcaatggat caaggacttt tatatcccac acggtaataa aatgttacaa   3900

ccttttgctc cttcatattc agctgaaatg aattc                             3935
```

```
<210> SEQ ID NO 9
<211> LENGTH: 133
<212> TYPE: PRT
<213> ORGANISM: Artificial Sequence
<220> FEATURE:
<223> OTHER INFORMATION: Synthetic polypeptide

<400> SEQUENCE: 9

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Ala Lys Phe Ala Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Gly Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130


<210> SEQ ID NO 10
<211> LENGTH: 399
<212> TYPE: DNA
<213> ORGANISM: Artificial Sequence
<220> FEATURE:
<223> OTHER INFORMATION: Synthetic nucleotide

<400> SEQUENCE: 10

gcccctacca gctcctccac caagaagacc cagctgcagc tggagcattt actgctggat     60
```

```
ttacagatga ttttaaacgg catcaacaac tacaagaacc ccaagctgac tcgtatgctg    120

accgccaagt tcgctatgcc caagaaggcc accgagctga agcacctcca gtgtttagag    180

gaggagctga agcctttaga ggaggtgctg aatggagccc agagcaagaa tttccattta    240

aggcctcgtg atttaatcag caacatcaac gtgatcgtgc tggagctgaa aggctccgag    300

accaccttca tgtgcgagta cgccgacgag accgccacca tcgtggagtt tttaaatcgt    360

tggatcacct tctgccagag catcatcagc actttaacc                           399
```

<210> SEQ ID NO 11
<211> LENGTH: 399
<212> TYPE: DNA
<213> ORGANISM: Artificial Sequence
<220> FEATURE:
<223> OTHER INFORMATION: Synthetic nucleotide

<400> SEQUENCE: 11

```
gcgccaacat caagttcgac caagaagacg cagttgcagc tagagcattt gcttttggat     60

cttcaaatga tccttaatgg tataaataat tataagaacc ccaaattgac gcgaatgcta    120

acagctaaat tcgcaatgcc aaagaaggca accgagttaa agcacctaca atgcttggaa    180

gaagaactaa aacccccttga ggaggtatta aatggtgctc agtcgaagaa ttttcatctt   240

cgacctcgag acctaatttc aaatattaac gtaattgttt tggaattaaa gggttcggaa    300

actactttta tgtgtgagta cgcagacgag acagctacaa tagtggagtt tcttaaccgt    360

tggataacct tttgtcaatc aatcatttcg actttgacc                           399
```

<210> SEQ ID NO 12
<211> LENGTH: 459
<212> TYPE: DNA
<213> ORGANISM: Artificial Sequence
<220> FEATURE:
<223> OTHER INFORMATION: Synthetic nucleotide

<400> SEQUENCE: 12

```
atgtatcgta tgcagctgct gagctgcatc gctttatctt tagctttagt gaccaacagc     60

gcccctacca gctcctccac caagaagacc cagctgcagc tggagcattt actgctggat    120

ttacagatga ttttaaacgg catcaacaac tacaagaacc ccaagctgac tcgtatgctg    180

accgccaagt tcgctatgcc caagaaggcc accgagctga agcacctcca gtgtttagag    240

gaggagctga agcctttaga ggaggtgctg aatggagccc agagcaagaa tttccattta    300

aggcctcgtg atttaatcag caacatcaac gtgatcgtgc tggagctgaa aggctccgag    360

accaccttca tgtgcgagta cgccgacgag accgccacca tcgtggagtt tttaaatcgt    420

tggatcacct tctgccagag catcatcagc actttaacc                           459
```

<210> SEQ ID NO 13
<211> LENGTH: 459
<212> TYPE: DNA
<213> ORGANISM: Artificial Sequence
<220> FEATURE:
<223> OTHER INFORMATION: Synthetic nucleotide

<400> SEQUENCE: 13

```
atgtatcgaa tgcaattact ttcctgtatc gcactttcat tagcccttgt gaccaactca     60

gcgccaacat caagttcgac caagaagacg cagttgcagc tagagcattt gcttttggat    120

cttcaaatga tccttaatgg tataaataat tataagaacc ccaaattgac gcgaatgcta    180
```

```
acagctaaat tcgcaatgcc aaagaaggca accgagttaa agcacctaca atgcttggaa    240

gaagaactaa aaccccttga ggaggtatta aatggtgctc agtcgaagaa ttttcatctt    300

cgacctcgag acctaatttc aaatattaac gtaattgttt tggaattaaa gggttcggaa    360

actactttta tgtgtgagta cgcagacgag acagctacaa tagtggagtt tcttaaccgt    420

tggataacct tttgtcaatc aatcatttcg actttgacc                           459
```

```
<210> SEQ ID NO 14
<211> LENGTH: 153
<212> TYPE: PRT
<213> ORGANISM: Artificial Sequence
<220> FEATURE:
<223> OTHER INFORMATION: Synthetic polypeptide

<400> SEQUENCE: 14

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Ala Lys Phe
    50                  55                  60

Ala Met Pro Lys Lys Ala Thr Glu Leu Lys His Leu Gln Cys Leu Glu
65                  70                  75                  80

Glu Glu Leu Lys Pro Leu Glu Glu Val Leu Asn Gly Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150
```

```
<210> SEQ ID NO 15
<211> LENGTH: 1914
<212> TYPE: DNA
<213> ORGANISM: Artificial Sequence
<220> FEATURE:
<223> OTHER INFORMATION: Synthetic nucleotide

<400> SEQUENCE: 15

gattacgacg tgctaatcta gcgtgtgaag acgataaatt aatgatctat ggattaccat     60

ggatgacaac tcaaacatct gcgttatcaa taaatagtaa accgatagtg tataaagatt    120

gtgcaaagct tttgcgatca ataaatggat cacaaccagt atctcttaac gatgttcttc    180

gcagatgatg attcattttt taagtatttg gctagtcaag atgatgaatc ttcattatct    240

gatatattgc aaatcactca atatctagac tttctgttat tattattgat ccaatcaaaa    300

aataaattag aagccgtggg tcattgttat gaatctcttt cagaggaata cagacaattg    360

acaaaattca cagactctca agattttaaa aaactgttta acaaggtccc tattgttaca    420

gatggaaggg tcaaacttaa taaaggatat ttgttcgact ttgtgattag tttgatgcga    480

ttcaaaaaag aatcctctct agctaccacc gcaatagatc ctattagata catagatcct    540

cgtcgcgata tcgcattttc taacgtgatg gatatattaa agtcgaataa agtgaacaat    600
```

aattaattct ttattgtcat catgaacggg cgcgcctata aaaattgaaa ttttattttt 660
tttttttgga atataaatat ccctatcagt gatagagatc tccctatcag tgatagagag 720
ccaccatgta tcgtatgcag ctgctgagct gcatcgcttt atctttagct ttagtgacca 780
acagcgcccc taccagctcc tccaccaaga agacccagct gcagctggag catttactgc 840
tggatttaca gatgatttta aacggcatca acaactacaa gaaccccaag ctgactcgta 900
tgctgaccgc caagttcgct atgcccaaga aggccaccga gctgaagcac ctccagtgtt 960
tagaggagga gctgaagcct ttagaggagg tgctgaatgg agcccagagc aagaatttcc 1020
atttaaggcc tcgtgattta atcagcaaca tcaacgtgat cgtgctggag ctgaaaggct 1080
ccgagaccac cttcatgtgc gagtacgccg acgagaccgc caccatcgtg gagtttttaa 1140
atcgttggat caccttctgc cagagcatca tcagcacttt aacctaatga gcgatcgcgt 1200
gtagaaagtg ttacatcgac tcataatatt atatttttta tctaaaaaac taaaaataaa 1260
cattgattaa attttaatat aatacttaaa aatggatgtt gtgtcgttag ataaaccgtt 1320
tatgtatttt gaggaaattg ataatgagtt agattacgaa ccagaaagtg caaatgaggt 1380
cgcaaaaaaa ctgccgtatc aaggacagtt aaaactatta ctaggagaat tatttttttct 1440 tagtaagtta cagcgacacg gtatattaga tggtgccacc gtagtgtata taggatcggc 1500
tcctggtaca catatacgtt atttgagaga tcatttctat aatttaggaa tgattatcaa 1560
atggatgcta attgacggac gccatcatga tcctattcta aatggattgc gtgatgtgac 1620
tctagtgact cggttcgttg atgaggaata tctacgatcc atcaaaaaac aactgcatcc 1680
ttctaagatt attttaattt ctgatgtaag atccaaacga ggaggaaatg aacctagtac 1740
ggcggattta ctaagtaatt acgctctaca aaatgtcatg attagtattt taaaccccgt 1800
ggcatctagt cttaaatgga gatgcccgtt tccagatcaa tggatcaagg acttttatat 1860
cccacacggt aataaaatgt tacaaccttt tgctccttca tattcagctg aaat 1914

<210> SEQ ID NO 16
<211> LENGTH: 3895
<212> TYPE: DNA
<213> ORGANISM: Artificial Sequence
<220> FEATURE:
<223> OTHER INFORMATION: Synthetic nucleotide

<400> SEQUENCE: 16
tgcattaatg aatcggccaa cgcgcgggga gaggcggttt gcgtattggg cgctcttccg 60
cttcctcgct cactgactcg ctgcgctcgg tcgttcggct gcggcgagcg gtatcagctc 120
actcaaaggc ggtaatacgg ttatccacag aatcagggga taacgcagga aagaacatgt 180
gagcaaaagg ccagcaaaag gccaggaacc gtaaaaaggc cgcgttgctg gcgtttttcc 240
ataggctccg cccccctgac gagcatcaca aaaatcgacg ctcaagtcag aggtggcgaa 300
acccgacagg actataaaga taccaggcgt ttccccctgg aagctccctc gtgcgctctc 360
ctgttccgac cctgccgctt accggatacc tgtccgcctt tctcccttcg ggaagcgtgg 420
cgctttctca tagctcacgc tgtaggtatc tcagttcggt gtaggtcgtt cgctccaagc 480
tgggctgtgt gcacgaaccc cccgttcagc ccgaccgctg cgccttatcc ggtaactatc 540
gtcttgagtc caacacggta agacacgact tatcgccact ggcagcagcc actggtaaca 600
ggattagcag agcgaggtat gtaggcggtg ctacagagtt cttgaagtgg tggcctaact 660
acggctacac tagaagaaca gtatttggta tctgcgctct gctgaagcca gttaccttcg 720

```
gaaaaagagt tggtagctct tgatccggca aacaaaccac cgctggtagc ggtggttttt    780
ttgtttgcaa gcagcagatt acgcgcagaa aaaaaggatc tcaagaagat cctttgatct    840
tttctacggg gtctgacgct cagtggaacg aaaactcacg ttaagggatt ttggtcatga    900
gattatcaaa aaggatcttc acctagatcc ttttaaatta aaaatgaagt tttaaatcaa    960
tctaaagtat atatgagtaa acttggtctg acagttacca atgcttaatc agtgaggcac   1020
ctatctcagc gatctgtcta tttcgttcat ccatagttgc ctgactcggc gtaatgctct   1080
gccagtgtta caaccaatta accaattctg attagaaaaa ctcatcgagc atcaaatgaa   1140
actgcaattt attcatatca ggattatcaa taccatattt ttgaaaaagc cgtttctgta   1200
atgaaggaga aaactcaccg aggcagttcc ataggatggc aagatcctgg tatcggtctg   1260
cgattccgac tcgtccaaca tcaatacaac ctattaattt cccctcgtca aaaataaggt   1320
tatcaagtga gaaatcacca tgagtgacga ctgaatccgg tgagaatggc aaaagcttat   1380
gcatttcttt ccagacttgt tcaacaggcc agccattacg ctcgtcatca aaatcactcg   1440
catcaaccaa accgttattc attcgtgatt gcgcctgagc gagacgaaat acgcgatcac   1500
tgttaaaagg acaattacaa acaggaatca aatgcaaccg gcgcaggaac actgccagcg   1560
catcaacaat attttcacct gaatcaggat attcttctaa tacctggaat gctgttttcc   1620
cggggatcgc agtggtgagt aaccatgcat catcaggagt acggataaaa tgcttgatgg   1680
tcggaagagg cataaattcc gtcagccagt ttagtctgac catctcatct gtaacatcat   1740
tggcaacgct acctttgcca tgtttcagaa acaactctgg cgcatcgggc ttcccataca   1800
atcgatagat tgtcgcacct gattgcccga cattatcgcg agcccattta tacccatata   1860
aatcagcatc catgttggaa tttaatcgcg gcctcgagca agacgtttcc cgttgaatat   1920
ggctcataac accccttgta ttactgttta tgtaagcaga caggtcgacg aattcgatta   1980
cgacgtgcta atctagcgtg tgaagacgat aaattaatga tctatggatt accatggatg   2040
acaactcaaa catctgcgtt atcaataaat agtaaaccga tagtgtataa agattgtgca   2100
aagcttttgc gatcaataaa tggatcacaa ccagtatctc ttaacgatgt tcttcgcaga   2160
tgatgattca ttttttaagt atttggctag tcaagatgat gaatcttcat tatctgatat   2220
attgcaaatc actcaatatc tagactttct gttattatta ttgatccaat caaaaaataa   2280
attagaagcc gtgggtcatt gttatgaatc tctttcagag gaatacagac aattgacaaa   2340
attcacagac tctcaagatt ttaaaaaact gtttaacaag gtccctattg ttacagatgg   2400
aagggtcaaa cttaataaag gatatttgtt cgactttgtg attagtttga tgcgattcaa   2460
aaaagaatcc tctctagcta ccaccgcaat agatcctatt agatacatag atcctcgtcg   2520
cgatatcgca ttttctaacg tgatggatat attaaagtcg aataaagtga acaataatta   2580
attctttatt gtcatcatga acgggcgcgc ctataaaaat tgaaatttta tttttttttt   2640
ttggaatata aatatcccta tcagtgatag agatctccct atcagtgata gagagccacc   2700
atgtatcgta tgcagctgct gagctgcatc gctttatctt tagctttagt gaccaacagc   2760
gcccctacca gctcctccac caagaagacc cagctgcagc tggagcattt actgctggat   2820
ttacagatga ttttaaacgg catcaacaac tacaagaacc ccaagctgac tcgtatgctg   2880
accgccaagt tcgctatgcc caagaaggcc accgagctga agcacctcca gtgtttagag   2940
gaggagctga agcctttaga ggaggtgctg aatggagccc agagcaagaa tttccattta   3000
aggcctcgtg atttaatcag caacatcaac gtgatcgtgc tggagctgaa aggctccgag   3060
accaccttca tgtgcgagta cgccgacgag accgccacca tcgtggagtt tttaaatcgt   3120
```

```
tggatcacct tctgccagag catcatcagc actttaacct aatgagcgat cgcgtgtaga   3180

aagtgttaca tcgactcata atattatatt ttttatctaa aaaactaaaa ataaacattg   3240

attaaatttt aatataatac ttaaaaatgg atgttgtgtc gttagataaa ccgtttatgt   3300

attttgagga aattgataat gagttagatt acgaaccaga aagtgcaaat gaggtcgcaa   3360

aaaaactgcc gtatcaagga cagttaaaac tattactagg agaattattt tttcttagta   3420

agttacagcg acacggtata ttagatggtg ccaccgtagt gtatatagga tcggctcctg   3480

gtacacatat acgttatttg agagatcatt tctataattt aggaatgatt atcaaatgga   3540

tgctaattga cggacgccat catgatccta ttctaaatgg attgcgtgat gtgactctag   3600

tgactcggtt cgttgatgag gaatatctac gatccatcaa aaaacaactg catccttcta   3660

agattatttt aatttctgat gtaagatcca aacgaggagg aaatgaacct agtacggcgg   3720

atttactaag taattacgct ctacaaaatg tcatgattag tattttaaac cccgtggcat   3780

ctagtcttaa atggagatgc ccgtttccag atcaatggat caaggacttt tatatcccac   3840

acggtaataa aatgttacaa ccttttgctc cttcatattc agctgaaatg aattc        3895
```

<210> SEQ ID NO 17
<211> LENGTH: 1914
<212> TYPE: DNA
<213> ORGANISM: Artificial Sequence
<220> FEATURE:
<223> OTHER INFORMATION: Synthetic nucleotide

<400> SEQUENCE: 17

```
gattacgacg tgctaatcta gcgtgtgaag acgataaatt aatgatctat ggattaccat     60

ggatgacaac tcaaacatct gcgttatcaa taaatagtaa accgatagtg tataaagatt    120

gtgcaaagct tttgcgatca ataaatggat cacaaccagt atctcttaac gatgttcttc    180

gcagatgatg attcattttt taagtatttg gctagtcaag atgatgaatc ttcattatct    240

gatatattgc aaatcactca atatctagac tttctgttat tattattgat ccaatcaaaa    300

aataaattag aagccgtggg tcattgttat gaatctcttt cagaggaata cagacaattg    360

acaaaattca cagactctca agattttaaa aaactgttta acaaggtccc tattgttaca    420

gatggaaggg tcaaacttaa taaaggatat ttgttcgact ttgtgattag tttgatgcga    480

ttcaaaaaag aatcctctct agctaccacc gcaatagatc ctattagata catagatcct    540

cgtcgcgata tcgcattttc taacgtgatg gatatattaa agtcgaataa agtgaacaat    600

aattaattct ttattgtcat catgaacggg cgcgcctata aaaattgaaa ttttattttt    660

tttttttgga atataaatat ccctatcagt gatagagatc tccctatcag tgatagagag    720

ccaccatgta tcgaatgcaa ttactttcct gtatcgcact ttcattagcc cttgtgacca    780

actcagcgcc aacatcaagt tcgaccaaga agacgcagtt gcagctagag catttgcttt    840

tggatcttca aatgatcctt aatggtataa ataattataa gaaccccaaa ttgacgcgaa    900

tgctaacagc taaattcgca atgccaaaga aggcaaccga gttaaagcac ctacaatgct    960

tggaagaaga actaaaaccc cttgaggagg tattaaatgg tgctcagtcg aagaattttc   1020

atcttcgacc tcgagaccta atttcaaata ttaacgtaat tgttttggaa ttaaagggtt   1080

cggaaactac ttttatgtgt gagtacgcag acgagacagc tacaatagtg gagtttctta   1140

accgttggat aaccttttgt caatcaatca tttcgacttt gacctaatga gcgatcgcgt   1200

gtagaaagtg ttacatcgac tcataatatt atatttttta tctaaaaaac taaaaataaa   1260
```

```
cattgattaa attttaatat aatacttaaa aatggatgtt gtgtcgttag ataaaccgtt   1320
tatgtatttt gaggaaattg ataatgagtt agattacgaa ccagaaagtg caaatgaggt   1380
cgcaaaaaaa ctgccgtatc aaggacagtt aaaactatta ctaggagaat tattttttct   1440
tagtaagtta cagcgacacg gtatattaga tggtgccacc gtagtgtata taggatcggc   1500
tcctggtaca catatacgtt atttgagaga tcatttctat aatttaggaa tgattatcaa   1560
atggatgcta attgacggac gccatcatga tcctattcta aatggattgc gtgatgtgac   1620
tctagtgact cggttcgttg atgaggaata tctacgatcc atcaaaaaac aactgcatcc   1680
ttctaagatt attttaattt ctgatgtaag atccaaacga ggaggaaatg aacctagtac   1740
ggcggattta ctaagtaatt acgctctaca aaatgtcatg attagtattt taaaccccgt   1800
ggcatctagt cttaaatgga gatgcccgtt tccagatcaa tggatcaagg acttttatat   1860
cccacacggt aataaaatgt tacaaccttt tgctccttca tattcagctg aaat         1914
```

<210> SEQ ID NO 18
<211> LENGTH: 3895
<212> TYPE: DNA
<213> ORGANISM: Artificial Sequence
<220> FEATURE:
<223> OTHER INFORMATION: Synthetic nucleotide

<400> SEQUENCE: 18

```
tgcattaatg aatcggccaa cgcgcgggga gaggcggttt gcgtattggg cgctcttccg     60
cttcctcgct cactgactcg ctgcgctcgg tcgttcggct gcggcgagcg gtatcagctc    120
actcaaaggc ggtaatacgg ttatccacag aatcagggga taacgcagga aagaacatgt    180
gagcaaaagg ccagcaaaag gccaggaacc gtaaaaaggc cgcgttgctg gcgtttttcc    240
ataggctccg cccccctgac gagcatcaca aaaatcgacg ctcaagtcag aggtggcgaa    300
acccgacagg actataaaga taccaggcgt ttccccctgg aagctccctc gtgcgctctc    360
ctgttccgac cctgccgctt accggatacc tgtccgcctt tctcccttcg ggaagcgtgg    420
cgctttctca tagctcacgc tgtaggtatc tcagttcggt gtaggtcgtt cgctccaagc    480
tgggctgtgt gcacgaaccc cccgttcagc ccgaccgctg cgccttatcc ggtaactatc    540
gtcttgagtc caacacggta agacacgact tatcgccact ggcagcagcc actggtaaca    600
ggattagcag agcgaggtat gtaggcggtg ctacagagtt cttgaagtgg tggcctaact    660
acggctacac tagaagaaca gtatttggta tctgcgctct gctgaagcca gttaccttcg    720
gaaaaagagt tggtagctct tgatccggca aacaaaccac cgctggtagc ggtggttttt    780
ttgtttgcaa gcagcagatt acgcgcagaa aaaaaggatc tcaagaagat cctttgatct    840
tttctacggg gtctgacgct cagtggaacg aaaactcacg ttaagggatt ttggtcatga    900
gattatcaaa aaggatcttc acctagatcc ttttaaatta aaaatgaagt tttaaatcaa    960
tctaaagtat atatgagtaa acttggtctg acagttacca atgcttaatc agtgaggcac   1020
ctatctcagc gatctgtcta tttcgttcat ccatagttgc ctgactcggc gtaatgctct   1080
gccagtgtta caaccaatta accaattctg attagaaaaa ctcatcgagc atcaaatgaa   1140
actgcaattt attcatatca ggattatcaa taccatattt ttgaaaaagc cgtttctgta   1200
atgaaggaga aaactcaccg aggcagttcc ataggatggc aagatcctgg tatcggtctg   1260
cgattccgac tcgtccaaca tcaatacaac ctattaattt cccctcgtca aaaataaggt   1320
tatcaagtga gaaatcacca tgagtgacga ctgaatccgg tgagaatggc aaaagcttat   1380
gcatttcttt ccagacttgt tcaacaggcc agccattacg ctcgtcatca aaatcactcg   1440
```

```
catcaaccaa accgttattc attcgtgatt gcgcctgagc gagacgaaat acgcgatcac   1500
tgttaaaagg acaattacaa acaggaatca aatgcaaccg gcgcaggaac actgccagcg   1560
catcaacaat attttcacct gaatcaggat attcttctaa tacctggaat gctgttttcc   1620
cggggatcgc agtggtgagt aaccatgcat catcaggagt acggataaaa tgcttgatgg   1680
tcggaagagg cataaattcc gtcagccagt ttagtctgac catctcatct gtaacatcat   1740
tggcaacgct acctttgcca tgtttcagaa acaactctgg cgcatcgggc ttcccataca   1800
atcgatagat tgtcgcacct gattgcccga cattatcgcg agcccattta tacccatata   1860
aatcagcatc catgttggaa tttaatcgcg gcctcgagca agacgtttcc cgttgaatat   1920
ggctcataac accccttgta ttactgttta tgtaagcaga caggtcgacg aattcgatta   1980
cgacgtgcta atctagcgtg tgaagacgat aaattaatga tctatggatt accatggatg   2040
acaactcaaa catctgcgtt atcaataaat agtaaaccga tagtgtataa agattgtgca   2100
aagcttttgc gatcaataaa tggatcacaa ccagtatctc ttaacgatgt tcttcgcaga   2160
tgatgattca tttttaagt atttggctag tcaagatgat gaatcttcat tatctgatat   2220
attgcaaatc actcaatatc tagactttct gttattatta ttgatccaat caaaaaataa   2280
attagaagcc gtgggtcatt gttatgaatc tctttcagag gaatacagac aattgacaaa   2340
attcacagac tctcaagatt ttaaaaaact gtttaacaag gtccctattg ttacagatgg   2400
aagggtcaaa cttaataaag gatatttgtt cgactttgtg attagtttga tgcgattcaa   2460
aaaagaatcc tctctagcta ccaccgcaat agatcctatt agatacatag atcctcgtcg   2520
cgatatcgca ttttctaacg tgatggatat attaaagtcg aataaagtga acaataatta   2580
attctttatt gtcatcatga acgggcgcgc ctataaaaat tgaaatttta ttttttttt   2640
ttggaatata aatatcccta tcagtgatag agatctccct atcagtgata gagagccacc   2700
atgtatcgaa tgcaattact ttcctgtatc gcactttcat tagcccttgt gaccaactca   2760
gcgccaacat caagttcgac caagaagacg cagttgcagc tagagcattt gcttttggat   2820
cttcaaatga tccttaatgg tataaataat tataagaacc ccaaattgac gcgaatgcta   2880
acagctaaat tcgcaatgcc aaagaaggca accgagttaa agcacctaca atgcttggaa   2940
gaagaactaa aacccccttga ggaggtatta aatggtgctc agtcgaagaa ttttcatctt   3000
cgacctcgag acctaatttc aaatattaac gtaattgttt tggaattaaa gggttcggaa   3060
actactttta tgtgtgagta cgcagacgag acagctacaa tagtggagtt tcttaaccgt   3120
tggataacct tttgtcaatc aatcatttcg actttgacct aatgagcgat cgcgtgtaga   3180
aagtgttaca tcgactcata atattatatt ttttatctaa aaaactaaaa ataaacattg   3240
attaaatttt aatataatac ttaaaaatgg atgttgtgtc gttagataaa ccgtttatgt   3300
attttgagga aattgataat gagttagatt acgaaccaga aagtgcaaat gaggtcgcaa   3360
aaaaactgcc gtatcaagga cagttaaaac tattactagg agaattattt tttcttagta   3420
agttacagcg acacggtata ttagatggtg ccaccgtagt gtatatagga tcggctcctg   3480
gtacacatat acgttatttg agagatcatt tctataattt aggaatgatt atcaaatgga   3540
tgctaattga cggacgccat catgatccta ttctaaatgg attgcgtgat gtgactctag   3600
tgactcggtt cgttgatgag gaatatctac gatccatcaa aaaacaactg catccttcta   3660
agattatttt aatttctgat gtaagatcca aacgaggagg aaatgaacct agtacggcgg   3720
atttactaag taattacgct ctacaaaatg tcatgattag tattttaaac cccgtggcat   3780
```

```
ctagtcttaa atggagatgc ccgtttccag atcaatggat caaggacttt tatatcccac   3840

acggtaataa aatgttacaa ccttttgctc cttcatattc agctgaaatg aattc        3895
```

<210> SEQ ID NO 19
<211> LENGTH: 507
<212> TYPE: DNA
<213> ORGANISM: Artificial Sequence
<220> FEATURE:
<223> OTHER INFORMATION: Synthetic nucleotide

<400> SEQUENCE: 19

```
atgtactcga tgcagttagc ttcctgcgtg accctaacct tagtcttgct agtgaattcg     60

gcgcccacct catcctcaac gtcatcttcc acagcggagg ctcaacagca gcagcaacag    120

cagcaacaac aacagcagca tttggaacaa ttgctaatgg acttacagga actactatca    180

agaatggaga attatcgaaa cctaaagtta cctcgaatgt tgacagcaaa atttgcgttg    240

ccaaagcagg ccacagagct aaaggaccta cagtgtcttg aagatgagct aggaccactt    300

cgtcacgttt tagacggaac acagtccaag tcttttcagt tggaagacgc cgagaacttt    360

atatctaaca tacgtgttac tgtcgtaaaa cttaaaggat cggacaatac tttcgaatgc    420

caattcgatg atgaaagtgc aaccgtcgtg gacttcttgc gacgttggat cgccttctgt    480

caaagtataa tttccacttc gccacag                                        507
```

<210> SEQ ID NO 20
<211> LENGTH: 2204
<212> TYPE: DNA
<213> ORGANISM: Artificial Sequence
<220> FEATURE:
<223> OTHER INFORMATION: Synthetic nucleotide

<400> SEQUENCE: 20

```
actttaatcc tgtgtttata gagcccacgt ttaaacattc tttattaagt gtttataaac     60

acagattaat agttttattt gaagtattcg ttgtattcat tctaatatat gtattttta    120

gatctgaatt aaatatgttc ttcatgccta aacgaaaaat acccgatcct attgatagat    180

tacgacgtgc taatctagcg tgtgaagacg ataaattaat gatctatgga ttaccatgga    240

tgacaactca aacatctgcg ttatcaataa atagtaaacc gatagtgtat aaagattgtg    300

caaagctttt gcgatcaata aatggatcac aaccagtatc tcttaacgat gttcttcgca    360

gatgatgatt catttttaa gtatttggct agtcaagatg atgaatcttc attatctgat    420

atattgcaaa tcactcaata tctagacttt ctgttattat tattgatcca atcaaaaaat    480

aaattagaag ccgtgggtca ttgttatgaa tctctttcag aggaatacag acaattgaca    540

aaattcacag actttcaaga ttttaaaaaa ctgtttaaca aggtccctat tgttacagat    600

ggaagggtca aacttaataa aggatatttg ttcgactttg tgattagttt gatgcgattc    660

aaaaaagaat cctctctagc taccaccgca atagatcctg ttagatacat agatcctcgt    720

cgcaatatcg cattttctaa cgtgatggat atattaaagt cgaataaagt gaacaataat    780

taattcttta ttgtcatcgg cgcgcctata aaaattgaaa ttttattttt ttttttgga    840

atataaatat ccctatcagt gatagagatc tccctatcag tgatagagag ccaccatgta    900

ctcgatgcag ttagcttcct gcgtgaccct aaccttagtc ttgctagtga attcggcgcc    960

cacctcatcc tcaacgtcat cttccacagc ggaggctcaa cagcagcagc aacagcagca   1020

acaacaacag cagcatttgg aacaattgct aatggactta caggaactac tatcaagaat   1080

ggagaattat cgaaacctaa agttacctcg aatgttgaca gcaaaatttg cgttgccaaa   1140
```

```
gcaggccaca gagctaaagg acctacagtg tcttgaagat gagctaggac cacttcgtca   1200

cgttttagac ggaacacagt ccaagtcttt tcagttggaa gacgccgaga actttatatc   1260

taacatacgt gttactgtcg taaaacttaa aggatcggac aatactttcg aatgccaatt   1320

cgatgatgaa agtgcaaccg tcgtggactt cttgcgacgt tggatcgcct tctgtcaaag   1380

tataatttcc acttcgccac agtattatat tttttatcta aaaaactaaa aataaacatt   1440

gattaaattt taatataata cttaaaaatg gatgttgtgt cgttagataa accgtttatg   1500

tattttgagg aaattgataa tgagttagat tacgaaccag aaagtgcaaa tgaggtcgca   1560

aaaaaactgc cgtatcaagg acagttaaaa ctattactag gagaattatt ttttcttagt   1620

aagttacagc gacacggtat attagatggt gccaccgtag tgtatatagg atctgctccc   1680

ggtacacata tacgttattt gagagatcat ttctataatt taggagtgat catcaaatgg   1740

atgctaattg acggccgcca tcatgatcct attttaaatg gattgcgtga tgtgactcta   1800

gtgactcggt tcgttgatga ggaatatcta cgatccatca aaaaacaact gcatccttct   1860

aagattattt taatttctga tgtgagatcc aaacgaggag gaaatgaacc tagtacggcg   1920

gatttactaa gtaattacgc tctacaaaat gtcatgatta gtattttaaa ccccgtggcg   1980

tctagtctta aatggagatg cccgtttcca gatcaatgga tcaaggactt ttatatccca   2040

cacggtaata aaatgttaca accttttgct ccttcatatt cagctgaaat gagattatta   2100

agtatttata ccggtgagaa catgagactg actcgagtta ccaaatcaga cgctgtaaat   2160

tatgaaaaaa agatgtacta ccttaataag atcgtccgta acaa                    2204
```

<210> SEQ ID NO 21
<211> LENGTH: 153
<212> TYPE: PRT
<213> ORGANISM: Homo sapiens

<400> SEQUENCE: 21

```
Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150
```

<210> SEQ ID NO 22
<211> LENGTH: 20
<212> TYPE: PRT

```
<213> ORGANISM: Homo sapiens

<400> SEQUENCE: 22

Met Tyr Arg Met Gln Leu Leu Ser Cys Ile Ala Leu Ser Leu Ala Leu
1               5                   10                  15

Val Thr Asn Ser
            20


<210> SEQ ID NO 23
<211> LENGTH: 149
<212> TYPE: PRT
<213> ORGANISM: Mus musculus

<400> SEQUENCE: 23

Ala Pro Thr Ser Ser Ser Thr Ser Ser Ser Thr Ala Glu Ala Gln Gln
1               5                   10                  15

Gln Gln Gln Gln Gln Gln Gln Gln Gln Gln His Leu Glu Gln Leu Leu
            20                  25                  30

Met Asp Leu Gln Glu Leu Leu Ser Arg Met Glu Asn Tyr Arg Asn Leu
        35                  40                  45

Lys Leu Pro Arg Met Leu Thr Phe Lys Phe Tyr Leu Pro Lys Gln Ala
    50                  55                  60

Thr Glu Leu Lys Asp Leu Gln Cys Leu Glu Asp Glu Leu Gly Pro Leu
65                  70                  75                  80

Arg His Val Leu Asp Leu Thr Gln Ser Lys Ser Phe Gln Leu Glu Asp
                85                  90                  95

Ala Glu Asn Phe Ile Ser Asn Ile Arg Val Thr Val Val Lys Leu Lys
            100                 105                 110

Gly Ser Asp Asn Thr Phe Glu Cys Gln Phe Asp Asp Glu Ser Ala Thr
        115                 120                 125

Val Val Asp Phe Leu Arg Arg Trp Ile Ala Phe Cys Gln Ser Ile Ile
    130                 135                 140

Ser Thr Ser Pro Gln
145


<210> SEQ ID NO 24
<211> LENGTH: 169
<212> TYPE: PRT
<213> ORGANISM: Mus musculus

<400> SEQUENCE: 24

Met Tyr Ser Met Gln Leu Ala Ser Cys Val Thr Leu Thr Leu Val Leu
1               5                   10                  15

Leu Val Asn Ser Ala Pro Thr Ser Ser Ser Thr Ser Ser Ser Thr Ala
            20                  25                  30

Glu Ala Gln Gln Gln Gln Gln Gln Gln Gln Gln Gln Gln Gln His Leu
        35                  40                  45

Glu Gln Leu Leu Met Asp Leu Gln Glu Leu Leu Ser Arg Met Glu Asn
    50                  55                  60

Tyr Arg Asn Leu Lys Leu Pro Arg Met Leu Thr Phe Lys Phe Tyr Leu
65                  70                  75                  80

Pro Lys Gln Ala Thr Glu Leu Lys Asp Leu Gln Cys Leu Glu Asp Glu
                85                  90                  95

Leu Gly Pro Leu Arg His Val Leu Asp Leu Thr Gln Ser Lys Ser Phe
            100                 105                 110

Gln Leu Glu Asp Ala Glu Asn Phe Ile Ser Asn Ile Arg Val Thr Val
        115                 120                 125
```

-continued

```
Val Lys Leu Lys Gly Ser Asp Asn Thr Phe Glu Cys Gln Phe Asp Asp
    130                 135                 140

Glu Ser Ala Thr Val Val Asp Phe Leu Arg Arg Trp Ile Ala Phe Cys
145                 150                 155                 160

Gln Ser Ile Ile Ser Thr Ser Pro Gln
                165
```